(12) United States Patent (10) Patent No.: US 7,700,347 B2
Levin (45) Date of Patent: Apr. 20, 2010

(54) METHODS AND APPARATUSES FOR CONDUCTING ASSAYS IN ANIMALS

(75) Inventor: Michael Levin, Swampscott, MA (US)

(73) Assignee: The Forsyth Institute, Boston, MA (US)

( * ) Notice: Subject to any disclaimer, the term of this patent is extended or adjusted under 35 U.S.C. 154(b) by 543 days.

(21) Appl. No.: 11/477,259

(22) Filed: Jun. 29, 2006

(65) Prior Publication Data

US 2007/0031962 A1 Feb. 8, 2007

Related U.S. Application Data

(60) Provisional application No. 60/696,407, filed on Jun. 30, 2005.

(51) Int. Cl.
 *C12M 3/00* (2006.01)
(52) U.S. Cl. .................................................. 435/288.4
(58) Field of Classification Search ........................ None
See application file for complete search history.

(56) References Cited

U.S. PATENT DOCUMENTS 4,022,054 A * 5/1977 Biederman ................. 73/23.34
6,637,372 B2 * 10/2003 Mauderli et al. ............ 119/417

OTHER PUBLICATIONS

Albertson, R. Craig and Kocher, Thomas D., "Assessing Morphological Differences in an Adaptive Trait: A Landmark-Based Morphometric Approach", Journal of Experimental Zoology, vol. 289, pp. 385-403 (2001).
Agata, K. et al., "Intercalary Regeneration in Planarians", Developmental Dynamics, vol. 226, pp. 308-316 (2003).
Agata, Kiyokazu, "Regeneration and Gene Regulation in Planarians", Current Opinion in Genetics & Development, vol. 13, pp. 492-496 (2003).
Agatonovic-Kustrin, et al., "Basic Concepts of Artificial Neural Network (ANN) Modeling and Its Application in Pharmaceutical Research", Journal of Pharmaceutical and Biomedical Analysis, vol. 22, pp. 717-727 (2000).
Brown, Frank A. et al., "Differentation Between Clockwise and Counterclockwise Magnetic Rotation by the Planarian, Dugesia Dorotacephala" Physiological Zoology, vol. 48, pp. 168-176 (1975).
Brown, F.A. et al., "A Persistent Monthly Variation in Responses of Planarians to Light, and Its Annual Modulation", International Journal of Chronobiology, vol. 3, pp. 57-62 (1975).
Brown, F.A. et al., "Seasonal Variations in Sign and Strength of Gamma-Taxis in Planarians", Nature, vol. 202(4931), pp. 469-471 (1964).
Brown, Frank A., "Effects and After-Effects on Planarians of Reversals of the Horizontal Magnetic Vector", Nature, vol. 209(5022), pp. 533-535 (1966).
Brown, H. Mack et al., "Spectral Sensitivity of the Planarian Ocellus", The Journal of General Physiology, vol. 51, pp. 255-260 (1968).
Buhmann, Joachim et al., "Image Recognition: Visual Grouping, Recognition, and Learning." PNAS, vol. 96(25), pp. 14203-14204 (1999).

Cebria, Francesc et al., "FGFR-Related Gene *Nou-Darake* Restricts Brain Tissues to the Head Region of Planarians", Nature, vol. 419, pp. 620-624 (2002).
Dehal, Paramvir et al., "The Draft Genome of *Ciona intestinalis*: Insights Into Chordate and Vertebrate Origins", Science, vol. 298, pp. 2157-2166 (2002).
Eisenstein, E.M., "Selecting a Model System for Neurobiological Studies of Learning and Memory", Behavioral Brain Research, vol. 82, pp. 121-132 (1997).
Frenger, "The Video Camera as an Artificial Retina", Biomedical Sciences Instrumentation, vol. 33, pp. 344-349 (1997).
Gostling, Neil et al., "Protochordate zic Genes Define Primitive Somite Compartments and Highlight Molecular Changes Underlying Neural Crest Evolution"; Evolution and Development, vol. 5(2), pp. 136-144 (2003).
Haycraft, Courtney et al., "The *C. elegans* Homolog of the Murine Cystic Kidney Disease Gene TG737 Functions in a Ciliogenic Pathway and is Disrupted in OSM-5 Mutant Worms", Development, vol. 128, pp. 1493-1505 (2001).
Holland, Linda et al., "The *Ciona intestinalis* Genome: When the Constraints are Off", Bioessays, vol. 25, pp. 529-532 (2003).
Klingenberg, Christian Peter et al., "Morphological Integration Between Developmental Compartments in the *Drosophila* Wing", Evolution, vol. 54(4), pp. 1273-1285 (2000).
Klingenberg, Christian Peter, "Heterochrony and Allometry: The Analysis of Evolutionary Change in Ontogeny", Biology Review, vol. 73, pp. 79-123 (1998).
Kwak, Inn-Sil et al, "Pattern Recognition of the Movement Tracks of Medaka (*Oryzias latipes*) in Response to Sub-Lethal Treatments of an Insecticide by Using Artificial Neural Networks", Environmental Pollution, vol. 120, pp. 671-681 (2002).
Levin, Michael, Abstract, "A Device for Automated Large-Scale Morphological and Behavioral Screening" National Science Foundation Grant No. DBI-0352370, Funding Start Date Jul. 1, 2004.
Levin, Michael, Abstract, "Cellular Learning and Information Outside of the Brain" National Institutes of Health Grant No. 1 R21 GM068483-01A1, Funding Start Date May 1, 2004.
Mason, P.R., "Chemo-Klino-Kinesis in Planarian Food Location", Animal Behavior, vol. 23, pp. 460-469 (1975).
Miyamoto, S. and Shimozawa, A., "Chemotaxis in the Freshwater Planarian, *Dugesia japonica japonica*", Zoological Science, vol. 2, pp. 389-395 (1985).
Offield, Martin et al., "The Development of *Xenopus tropicalis* Transgenic Lines and Their Use in Studying Lens Developmental Timing in Living Embryos", Development, vol. 127, pp. 1789-1797 (2000).
Ogasawara, Michio et al., "Gene Expression Profiles in Young Adult *Ciona intestinalis* ", Dev Genes Evol, vol. 212, pp. 173-185 (2002).

(Continued)

*Primary Examiner*—Ann Y Lam
(74) *Attorney, Agent, or Firm*—Ropes & Gray LLP

(57) ABSTRACT

The invention provides apparatuses, systems, and methods for conducting assays in aquatic animals. The apparatuses, systems, and methods of the invention can be used to identify and/or characterize compounds that modulate morphological, anatomical, or behavioral characteristics. The apparatuses, systems, and methods of the invention can be used to identify and/or characterize compounds that modulate learning or memory.

39 Claims, 17 Drawing Sheets

OTHER PUBLICATIONS

Oviedo, Nestor et al., "Allometric Scaling and Proportion Regulation in the Freshwater Planarian *Schmidtea mediterranea*", Developmental Dynamics, vol. 226, pp. 326-333 (2003).

Patane, Giuseppe et al., "The Enhanced LBG Algorithm", Neural Networks, vol. 14, pp. 1219-1237 (2001).

Pope, Edward C. et al., "The Heart of *Ciona intestinalis*: Eicosanoid-Generating Capacity and the Effects of Precursor Fatty Acids and Eicosanoids on Heart Rate", The Journal of Experimental Biology, vol. 205, pp. 1577-1583 (2002).

Rodenacker Karsten et al., "A Feature Set for Cytometry on Digitized Microscopic Images", Analytical Cellular Pathology, vol. 25, pp. 1-36 (2003).

Sarnat, Harvey B. et al., "The Brain of the Planarian As the Ancestor of the Human Brain", The Canadian Journal of Neurological Sciences, vol. 12(4), pp. 296-302 (1985).

Tagawa, Kuni et al., "Molecular Studies of Hemichordate Development: A Key to Understanding the Evolution of Bilateral Animals and Chordates", Evolution and Development, vol. 3(6), pp. 443-454 (2001).

Wang, F. et al., "A New & Robust Information Theoretic Measure and Its Application to Image Alignment", INF Process Med Imaging, vol. 18, pp. 388-400 (2003).

Zimmer Christophe et al., "Segmentation and Tracking of Migrating Cells in Videomicroscopy With Parametric Active Contours: A Tool for Cell-Based Drug Testing", IEEE Transactions on Medical Imaging, vol. 21(10), pp. 1212-1221 (2002).

* cited by examiner (A)

(B)

METHODS AND APPARATUSES FOR CONDUCTING ASSAYS IN ANIMALS

RELATED APPLICATIONS

This application claims priority to U.S. Provisional Application Ser. No. 60/696,407, filed Jun. 30, 2005, the disclosure of which is hereby incorporated by reference in its entirety.

FUNDING

The invention described herein was supported, in whole or in part, by the National Institute of Health grant no. R21-GM-068483-A1 and the National Science Foundation instrument grant 0352370. The United States government has certain rights in the invention.

BACKGROUND OF THE INVENTION

Many academic and commercial projects have generated combinatorial libraries of small molecules, nucleic acids, or proteins. Screening through these libraries will result in the identification of novel compounds of interest to basic science and medicine. However, automated high-throughput methods currently exist only for very simple systems (e.g., in vitro assays or single cells). Thus, the current state of the art makes it difficult or impossible to conduct high-throughput screens in complex organisms or to conduct screens to identify and/or characterize compounds which affect higher-order behavioral, morphological, or anatomical characteristics in complex organisms.

The current state of the art regarding screening assays in complex organisms is also limited in other respects. Even assays of single candidate compounds or of a small number of candidate compounds can be difficult when conducted in complex organisms. Specifically, assays based on making multiple observations of a complex organism over time are prone to experimenter bias, error, and fatigue. This problem is exacerbated when attempts to scale-up such a screen are made.

The limitations of the current state of the art are perhaps most acutely, although certainly not exclusively, experienced when the observational endpoint of the screening assay is a metric such as learning or memory. Such cases represent perhaps the most complex of animal behavior. Furthermore, assays that chart changes in learning or memory typically require the gathering and analysis of data points over time, thus exacerbating the potential that experimenter bias, error, or fatigue will influence the results.

An important aspect of biology is the discovery of novel genes, proteins, or chemical reagents that have interesting, useful, and/or enlightening effects upon living systems. We appear to be leaving the classical era where these were mainly discovered fortuitously (e.g., most antibiotics and neurotoxins), but are still fairly far from the generalized ability of rational design of drugs or proteins, linking structure to desired function at will (Debouck and Metcalf (2000) Annul Rev Pharmacol Toxicol 40: 193-207; Farber (1999) Pharmacol Ther 84: 327-332). Thus, current efforts are focused on screening approaches: locating interesting reagents by large-scale high-throughput examination of candidate molecules present, for example, in a combinatorial library (Bensing et al. (2001) Infect Immun 69: 1373-1380; Cheung et al. (2002) Nature Cell Biol 4: 83-88; Goodnow (2001) J Cell Biochem Supp 37: 13-21; Katayama et al., 2001; Koide et al. (2001) J Am Chem Soc 123: 398-408; MacNeil et al. (2001) J Mol Microbiol Biotechnol 3: 301-308; Nuttall (2001) Cells Tissues Organs 169: 265-271). A number of academic and commercial pharmaceutical projects have generated large genetic, proteomic, or small-molecule (drug) libraries that must be screened to identify compounds of interest to both biomedicine and basic biology (Stephen et al. (2002) Biochem Biophys Res Comm 296: 1228-1237), or proteins which alter specific patterning events in developing embryos (Caveman (2000) J Cell Sci 113: 3543-3544; Colaiacovo et al. (2002) Genetics 162: 113-128; Cram et al. (2003) J Cell Sci 116: 3871-3878; Gonczy et al. (2000) Nature 408: 331-336; Lee et al. (2003) Nucleic Acid Research 31: 7165-7174; Thatcher et al. (2001) Develop Biol 229: 480-493; Tseng and Hariharan (2002) Genetics 162: 229-243; Vastenhouw et al. (2003) Current Biol 13: 1311-1316).

There is an endless list of potential targets for which screening of libraries would result in medically-valuable reagents, or perturbation of biological processes which then lead to increased basic understanding of endogenous control mechanisms. Generating the libraries is often easy; the crucial and usually most difficult aspect is the choice of screening methods, apparatuses, and systems. This requires a tractable yet relevant model system, a degree of automation (to ensure temporal and financial feasibility), and a test which gives useful answers for each candidate. Some screens have been successfully conducted using cell culture or unicellular organisms (e.g. bacteria or yeast) (Chen and Zhao (2003) Gene 306: 127-134). Large-scale screens in model systems such as mice are not feasible due to cost constraints and the resulting low sample size.

The foregoing illustrate examples of some of the limitations of the prior art. The present invention addresses these and other limitations, and provides apparatuses, systems, and methods for conducting assays in animals.

BRIEF SUMMARY OF THE INVENTION

The present invention provides apparatuses, systems, and methods for conducting assays in animals. The present invention addresses the limitations of prior art apparatuses, systems, and methods by facilitating well controlled experiments where behavioral, morphological, and anatomical changes can be readily observed and analyzed with less experimenter bias or error. The present invention is readily adaptable for use with a wide range of animals of various sizes, shapes, and stages of development. Furthermore, the present invention is readily adaptable for use in a range of experiments and screening assays.

In certain embodiments, the apparatuses, systems, and methods of the present invention are used for conducting assays in aquatic animals. In certain other embodiments, the apparatuses, systems, and methods of the present invention are used for conducting assays in non-aquatic animals. Depending on whether the experimental organism (test animal) is an aquatic or non-aquatic organism, the user can select the culture medium and culture conditions appropriate for maintaining the animal during the course of the experiment. For example, aquatic animals can be maintained in water or other appropriate liquid media. Non-aquatic animals can be maintained substantially in the absence of liquid media, for example, on a layer of agar, wax, plastic, rubber, or other non-liquid surface. By altering the media in which the test organisms are maintained, the apparatuses, methods, and systems of the present invention can be readily adapted for use with a range of experimental (test) organisms.

In a first aspect, the invention provides an apparatus for conducting assays in an aquatic animal. The apparatus comprises a reaction well capable of housing fluid and an aquatic animal and having a transparent viewing surface; an inlet for introducing fluid into the reaction well; an outlet for removing fluid from the reaction well; and a removable lid.

In a second aspect, the invention provides an apparatus for conducting assays in an aquatic animal. The apparatus comprises a reaction well capable of housing fluid and an aquatic animal and having at least one transparent viewing surface; an inlet for introducing fluid into the reaction well; an outlet for removing fluid from the reaction well; an electrical element; and a removable lid.

In one embodiment, the transparent viewing surface is a surface of the reaction well. In another embodiment, the transparent viewing surface is a portion of a surface of the reaction, for example, a transparent port or window within a surface of the reaction well.

In one embodiment, the apparatus includes a plurality of reaction wells and a plurality of removable lids. In another embodiment, the apparatus includes a plurality of reaction wells and a removable lid covering the plurality of reaction wells. The lid may optionally include a transparent viewing surface, such as a surface of the lid or a portion thereof.

In certain embodiments, the apparatus includes a means for reversibly securing the lid to the apparatus or to the reaction well. Exemplary means include, but are not limited to, clips, screws, snaps, or magnetic portions affixed to both the lid and to the reaction well or apparatus.

In certain embodiments, the apparatus further includes an electrical element coupled to the reaction well for delivering an electrical current to the animal in the reaction well. By way of example, the electrical element may include a pair of electrodes. In certain embodiments, the pair of electrodes is affixed to an interior surface of the reaction well. In certain other embodiments, the electrical current can be delivered by a screen affixed to or embedded in an interior surface (e.g., the interior, bottom surface) of the reaction well. In certain other embodiments, the electrical current can be delivered by a screen (e.g, a mesh or wire) affixed to or embedded in an interior surface of the lid. When screens, electrodes, or other means to deliver the electrical current to the animal contact the fluid in which the animal is housed, the screen or electrodes can be constructed of or coated with a material that is non-corrosive and/or does not release harmful by-products into the fluid. By way of example, the screen or electrodes can be constructed of or coated with platinum, titanium, or platinum/iridium. Regardless of the means used for delivering an electrical current to the animal in the reaction well, the invention contemplates that the means can be modulated by an operator or by software installed on a computer to control the magnitude and the timing of the electrical current.

In certain embodiments, the apparatus further includes a light source for providing a light stimulus to the animal in the reaction well. Such a light source may be included within the lid or may be separate from the lid. When the light source is included in the lid, the lid may further include an electrical element for delivering an electrical current to the animal in the reaction well. Alternatively, the electrical element may be separate from the lid, for example, embedded in the reaction well. In any of the foregoing, the apparatus may further include an additional light source for providing background light. Such background light may be useful, for example, for supplying sufficient light for the capture of good images by the camera or photo-element.

In certain embodiments, the apparatus further includes a shield for excluding external stimuli. The shield may be separate from the lid, and such separate shield may include a light source for providing a light stimulus and/or a light source for providing background light. Alternatively, the shield may be incorporated into the lid. By way of example, one or more of the surfaces of the lid may be opaque. Such a substantially opaque lid would effectively shield the aquatic animal from external stimuli when the reaction well was covered by the lid. By way of further example, a separate shield may be affixed to the lid.

In any of the foregoing, the lid or shield may include a circuit board for interconnection to the light source and/or to the electrical element.

In a third aspect, the invention provides an apparatus for conducting assays in an aquatic animal. The apparatus comprises a reaction well capable of housing fluid and an aquatic animal and having at least one transparent viewing surface; a removable lid; an electrical element coupled to the reaction well for delivering an electrical current to the animal in the reaction well; at least one light source for providing a light stimulus to the animal in the reaction well; and at least one light source for providing background light to the reaction well.

In one embodiment, the transparent viewing surface is one surface of the reaction well. In another embodiment, the transparent viewing surface is a portion of a surface of the reaction well, for example, a transparent port or window within a surface of the reaction well.

In one embodiment, the apparatus includes a plurality of reaction wells and a plurality of removable lids. In another embodiment, the apparatus includes a plurality of reaction wells and a removable lid covering the plurality of reaction wells. The lid may optionally include a transparent viewing surface, such as a surface of the lid or a portion thereof.

In certain embodiments, the apparatus includes a means for reversibly securing the lid to the apparatus or to the reaction well. Exemplary means include, but are not limited to, clips, screws, snaps, tape, or magnetic element affixed to both the lid and to the reaction well or apparatus.

In certain embodiments, the apparatus further includes an electrical element for delivering an electrical current to the animal in the reaction well. By way of example, the electrical element may include a pair of electrodes. In certain embodiments, the pair of electrodes is affixed to an interior surface of the reaction well. In certain other embodiments, the electrical current can be delivered by a screen affixed to or embedded in an interior surface (e.g., the interior, bottom surface) of the reaction well. In certain other embodiments, the electrical current can be delivered by a screen affixed to or embedded in an interior surface of the lid. In still other embodiments, the electrical current can be delivered by electrodes placed in the vicinity of the inlet and the outlet. When screens, electrodes, or other means to deliver the electrical current to the animal contact the fluid in which the animal is housed, the screen or electrodes can be constructed of or coated with a material that is non-corrosive, substantially inert and/or does not release harmful by-products into the fluid. By way of example, the screen or electrodes can be constructed of or coated with platinum, titanium, or platinum/iridium. Regardless of the means used for delivering an electrical current to the animal in the reaction well, the invention contemplates that the means can be modulated by an operator or by software installed on a computer to control the magnitude and the timing of the electrical current.

In certain embodiments, the apparatus further includes a light source for providing a light stimulus to the animal in the reaction well. Such a light source may be included within the lid or may be separate from the lid. When the light source is included in the lid, the lid may further include an electrical element for delivering an electrical current to the animal in the reaction well. Alternatively, the electrical element may be separate from the lid, for example, embedded in the reaction well. In any of the foregoing, the apparatus may further include an additional light source for providing background light. Such background light may be useful, for example, for providing light sufficient for the capture of good images by the camera or photo-element.

In certain embodiments, the apparatus further includes a shield for excluding external stimuli. The shield may be separate from the lid, and such separate shield may include a light source for providing a light stimulus and/or a light source for providing background light. Alternatively, the shield may be incorporated into the lid. By way of example, one or more of the surfaces of the lid may be opaque. Such a substantially opaque lid would effectively shield the aquatic animal from external stimuli when the reaction well was covered by the lid. By way of further example, a separate shield may be affixed to the lid.

In certain embodiments, apparatus includes a circuit board for interconnection to one or more of a light source and an electrical element. In certain embodiments, the lid includes a circuit board. In certain other embodiments, the shield includes the circuit board.

In certain embodiments, the reaction well includes an inlet for introducing fluid into the reaction well. In certain other embodiments, the reaction well includes an outlet for removing fluid from the reaction well. In certain other embodiments, the reaction well includes both an inlet for introducing fluid into the reaction well and an outlet for removing fluid from the reaction well.

In a fourth aspect, the invention provides an apparatus for conducting assays in aquatic animals. The apparatus comprises a reaction well capable of housing fluid and an animal and having at least one transparent viewing surface; a removable lid; an inlet for introducing fluid into the reaction well; at least one light source for providing a light stimulus to the animal in the reaction well and/or for providing background light to the reaction well.

In one embodiment, the transparent viewing surface is one surface of the reaction well. In another embodiment, the transparent viewing surface is a portion of a surface of the reaction well, for example, a transparent port or window within a surface of the reaction well.

In one embodiment, the apparatus includes a plurality of reaction wells and a plurality of removable lids. In another embodiment, the apparatus includes a plurality of reaction wells and a removable lid covering the plurality of reaction wells. The lid may optionally include a transparent viewing surface, such as a surface of the lid or a portion thereof.

In certain embodiments, the apparatus includes a means for reversibly securing the lid to the apparatus or to the reaction well. Exemplary means include, but are not limited to, clips, screws, snaps, or magnetic portions affixed to both the lid and to the reaction well or apparatus.

In certain embodiments, the apparatus further includes an electrical element coupled to the reaction well for delivering an electrical current to the animal in the reaction well. By way of example, the electrical element may include a pair of electrodes. In certain embodiments, the pair of electrodes is affixed to an interior surface of the reaction well. In certain other embodiments, the electrical current can be delivered by a mesh affixed to or embedded in an interior surface (e.g., the interior, bottom surface) of the reaction well. In certain other embodiments, the electrical current can be delivered by a mesh affixed to or embedded in an interior surface of the lid. When screens, electrodes, or other means to deliver the electrical current to the animal contact the fluid in which the animal is housed, the screen or electrodes can be constructed of or coated with a material that is non-corrosive, substantially inert, and/or does not release harmful by-products into the fluid. By way of example, the screen or electrodes can be constructed of or coated with platinum, titanium, or platinum/iridium. Regardless of the means used for delivering an electrical current to the animal in the reaction well, the invention contemplates that the means can be modulated by an operator or by software installed on a computer to control the magnitude and the timing of the electrical current.

In certain embodiments, the apparatus further includes a light source for providing a light stimulus to the animal in the reaction well. Such a light source may be included within the lid or may be separate from the lid. When the light source is included in the lid, the lid may further include an electrical element for delivering an electrical current to the animal in the reaction well. Alternatively, the electrical element may be separate from the lid, for example, embedded in the reaction well. In any of the foregoing, the apparatus may further include an additional light source for providing background light. Such background light may be useful, for example, for providing sufficient light for the capture of good images by the camera or photo-element.

In certain embodiments, the apparatus further includes a shield for excluding external stimuli. The shield may be separate from the lid, and such separate shield may include a light source for providing a light stimulus and/or a light source for providing background light. Alternatively, the shield may be incorporated into the lid. By way of example, one or more of the surfaces of the lid may be opaque. Such a substantially opaque lid would effectively shield the aquatic animal from external stimuli when the reaction well was covered by the lid. By way of further example, a separate shield may be affixed to the lid.

In certain embodiments, the apparatus includes a circuit board for interconnection to one or more of a light source and an electrical element for delivering an electrical current. In certain embodiments, the lid includes a circuit board. In certain other embodiments, the shield includes the circuit board.

In certain embodiments, the reaction well includes both an inlet for introducing fluid into the reaction well and an outlet for removing fluid from the reaction well.

Any of the foregoing apparatuses can be used, for example, in conducting assays that measure changes in behavioral, anatomical, or morphological characteristics of an aquatic animal. Further assays include screening assays to identify or characterize compounds or stimuli that affect a behavioral, morphological, or anatomical characteristic of an animal. By way of further example, the apparatus can be used for assays or screens related to memory or learning. Additionally, the apparatus can be used for conducting a mutagenesis screen or to analyze the phenotype of putative mutants obtained from a mutagenesis screen.

For any of the foregoing aspects of the invention, the reaction well may be made, for example, of plastic, glass, or lucite. In certain embodiments, the apparatus is made of plastic, glass, or lucite, and one or more reaction wells (e.g., a single reaction well or a plurality of reaction wells) of the appropriate size and shape are molded or machined into the plastic, glass, or lucite apparatus.

Regardless of the particular materials from which the reaction well is constructed, the surface of the reaction well that contacts the fluid and the aquatic animal should be substantially non-reactive and non-corrosive. In certain embodiments, the interior surface of the reaction well is lined with a substantially non-reactive substance (e.g., a layer of teflon, polypropylene). In certain other embodiments, the interior surface of the reaction well is coated with one or more advantageous substances that inhibit degradation of compounds that may be added to the reaction well. Exemplary coatings include, without limitations, anti-bacterial agents, anti-viral agents, protease inhibitors, RNase inhibitors, and DNase inhibitors. In other embodiments, such agents are not supplied as a coating on the interior surface of the reaction well but are instead supplied in solution as part of the fluid used to house the aquatic animal.

For any of the foregoing aspects of the invention, the apparatus and/or the reaction wells may be sized and shaped to accommodate various aquatic animals, as well as fluids appropriate for maintaining the aquatic animals. Exemplary aquatic animals are relatively small such that they can be maintained in the amount of space typically available in a traditional laboratory setting. Small aquatic animals include animals of virtually any developmental stage including, but not limited to, embryonic, adult, juvenile, tadpole, larval, and fetal aquatic animals.

In certain embodiments, the aquatic animal is a chordate, hemichordate or protochordate. In certain embodiments, the aquatic animal is an invertebrate. In certain embodiments, the aquatic animal is a flatworm. In certain other embodiments, the flatworm is a planarian of the class Turbellaria. Other exemplary aquatic animals that may be housed in these apparatuses include Xenopus embryos and tadpoles, zebrafish, nematodes, amphioxous, sea squirt, and sea urchin embryos and larvae.

In a fifth aspect, the invention provides a system for conducting assays in an aquatic animal. The system comprises a reaction well capable of housing fluid and an aquatic animal and having at least one transparent viewing surface; a removable lid that reversibly covers the reaction well; at least one camera; an interface box for interconnection between the camera, the circuit board, and a computer; and image analysis software for installation on a computer which can be interconnected to the interface box.

In a sixth aspect, the invention provides a system for conducting assays in an aquatic animal. The system comprises an apparatus according to any of the aspects of the invention; an interface box for interconnection between a camera, a circuit board, and a computer; and image analysis software for installation on a computer interconnected to the interface box.

In one embodiment, the removable lid includes an electrical element for delivering an electrical current to the reaction well, at least one light source for providing a light stimulus to the animal in the reaction well, at least one light source for providing background light to the reaction well, and a circuit board. In another embodiment, the circuit board is for interconnection to one or more of the light source for providing a light stimulus, the light source for providing background light, and the electrical element for delivering an electrical current to the reaction well.

In one embodiment, the transparent viewing surface is one surface of the reaction well. In another embodiment, the transparent viewing surface is a portion of a surface of the reaction well, for example, a transparent port or window within a surface of the reaction well.

In one embodiment, the apparatus includes a plurality of reaction wells and a plurality of removable lids. In another embodiment, the apparatus includes a plurality of reaction wells and a removable lid covering the plurality of reaction wells. The lid may optionally include a transparent viewing surface, such as a surface of the lid or a portion thereof.

In certain embodiments, the apparatus includes a means for reversibly securing the lid to the apparatus or to the reaction well. Exemplary means include, but are not limited to, clips, screws, snaps, or magnetic portions affixed to both the lid and to the reaction well or apparatus.

In certain embodiments, the apparatus further includes a an electrical element coupled to the reaction well for delivering an electrical current to the animal in the reaction well. By way of example, the electrical element may include a pair of electrodes. In certain embodiments, the pair of electrodes is affixed to an interior surface of the reaction well. In certain other embodiments, the electrical current can be delivered by a screen affixed to or embedded in an interior surface (e.g., the interior, bottom surface) of the reaction well. In certain other embodiments, the electrical current can be delivered by a screen affixed to or embedded in an interior surface of the lid. When screens, electrodes, or other means to deliver the electrical current to the animal contact the fluid in which the animal is housed, the screen or electrodes can be constructed of or coated with a material that is non-corrosive, substantially inert, and/or does not release harmful by-products into the fluid. By way of example, the screen or electrodes can be constructed of or coated with platinum, titanium, or platinum/iridium. Regardless of the means used for delivering an electrical current to the animal in the reaction well, the invention contemplates that the means can be modulated by an operator or by software installed on a computer to control the magnitude and the timing of the electrical current.

In certain embodiments, the apparatus further includes a light source for providing a light stimulus to the animal in the reaction well. Such a light source may be included within the lid or may be separate from the lid. When the light source is included in the lid, the lid may further include an electrical element for delivering an electrical current to the animal in the reaction well. Alternatively, the electrical element may be separate from the lid, for example, embedded in the reaction well. In any of the foregoing, the apparatus may further include an additional light source for providing background light. Such background light may be useful, for example, for providing sufficient light for the capture of good images by the camera or photo-element.

In certain embodiments, the apparatus further includes a shield for excluding external stimuli. The shield may be separate from the lid, and such separate shield may include a light source for providing a light stimulus and/or a light source for providing background light. Alternatively, the shield may be incorporated into the lid. By way of example, one or more of the surfaces of the lid may be opaque. Such a substantially opaque lid would effectively shield the aquatic animal from external stimuli when the reaction well was covered by the lid. By way of further example, a separate shield may be affixed to the lid.

In certain embodiments, apparatus includes a circuit board for interconnection to one or more of a light source and an electrical element for delivering an electrical current. In certain embodiments, the lid includes a circuit board. In certain other embodiments, the shield includes the circuit board.

In certain embodiments, the reaction well includes an inlet for introducing fluid into the reaction well. In certain other embodiments, the reaction well includes an outlet for removing fluid from the reaction well. In certain other embodiments, the reaction well includes both an inlet for introducing fluid into the reaction well and an outlet for removing fluid from the reaction well.

In one embodiment, the system includes a plurality of reaction wells. In another embodiment, the plurality of reaction wells are aligned in a tray containing slots sized and shaped for the reaction wells. Exemplary trays containing slots sized and shaped for the reaction wells may comprise a surface of a plexiglass box.

In certain embodiments, the system includes a camera or photo-element. For example, the system may include a single camera capable of capturing images from a single reaction well or from multiple reaction wells. Alternatively, the system may include a plurality of cameras. Each of the plurality of cameras may be used to capture images from a single reaction well, or each of the plurality of cameras may be used to capture images from multiple reaction wells.

Any of the foregoing systems can be used, for example, in conducting assays that measure changes in behavioral, anatomical, or morphological characteristics of an aquatic animal. Further assays include screening assays to identify or characterize compounds or stimuli that affect a behavioral, morphological, or anatomical characteristic of an animal. By way of further example, the apparatus can be used for assays or screens related to memory or learning. Additionally, the apparatus can be used for conducting a mutagenesis screen or to analyze the phenotype of putative mutants obtained from a mutagenesis screen.

For any of the foregoing, the apparatus or system may include a thermocouple to regulate the temperature of the fluid in the reaction well during the experiment.

For any of the foregoing systems of the invention, the reaction well may be made, for example, of plastic, glass, or lucite. In certain embodiments, the apparatus is made of plastic, glass, or lucite, and one or more reaction wells (e.g., a single reaction well or a plurality of reaction wells) of the appropriate size and shape are molded or machined into the plastic, glass, or lucite apparatus.

Regardless of the particular materials from which the reaction well is constructed, the surface of the reaction well that contacts the fluid and the aquatic animal should be substantially non-reactive and non-corrosive. In certain embodiments, the interior surface of the reaction well is lined with a substantially non-reactive substance (e.g., a layer of teflon, polypropylene, etc.). In certain other embodiments, the interior surface of the reaction well is coated with one or more advantageous substances that inhibit degradation of compounds that may be added to the reaction well. Exemplary coatings include, without limitations, anti-bacterial agents, anti-viral agents, protease inhibitors, RNase inhibitors, DNase inhibitors, and the like. In other embodiments, such agents are not supplied as a coating on the interior surface of the reaction well but are instead supplied in solution as part of the fluid used to house the aquatic animal.

For any of the foregoing systems of the invention, the apparatus and/or the reaction wells may be sized and shaped to accommodate various aquatic animals, as well as fluids appropriate for maintaining the aquatic animals. Exemplary aquatic animals are relatively small such that they can be maintained in a reasonable amount of space available in a traditional laboratory setting. Small aquatic animals include animals of virtually any developmental stage including, but not limited to, embryonic, adult, juvenile, tadpole, larval, and fetal aquatic animals.

In certain embodiments, the aquatic animal is a chordate, hemichordate or protochordate. In certain embodiments, the aquatic animal is an invertebrate. In certain embodiments, the aquatic animal is a flatworm. In certain other embodiments, the flatworm is a planarian of the class Turbellaria. Other exemplary aquatic animals that may be housed in these apparatuses include Xenopus embryos and tadpoles, zebrafish, nematodes, amphioxous, sea squirt, and sea urchin embryos and larvae.

In a seventh aspect, the invention provides a method for screening for compounds that alter learning or memory in an aquatic animal. The method comprises culturing an aquatic animal in a reaction well capable of housing fluid and an aquatic animal and having a transparent viewing surface; training said aquatic animal to react to a stimuli; exposing said trained animal to a compound; and observing changes in the reaction of the trained animal to the stimuli in the presence of the compound versus absence of the compound. The comparison can be made in the same animal (e.g., behavior in the presence versus the absence of compound in the same animal) or in a separate control animal (e.g., behavior in the presence of the compound in a test animal versus behavior in the absence of the compound in a control animal). One or more compounds that alter the reaction of the trained animal to the stimuli is identified as a compound that alters learning or memory, wherein the reactions and changes in the reactions of the aquatic animal are measured using image analysis software installed on a computer.

In one embodiment, the stimuli are light and/or an electrical current.

In another embodiment, the compound is selected from a nucleic acid, a peptide, a protein, or a small molecule. Compounds can be supplied individually, or in pools of multiple compounds. Exemplary compounds include, but are not limited to, RNAi constructs, antibodies, antisense oligonucleotides, sense oligonucleotides, peptides, peptidomimetics, small organic molecules, small inorganic molecules, and the like.

In another embodiment, the method comprises a high-throughput method for screening a plurality of compounds in a plurality of reaction wells.

In another embodiment, the reactions and/or changes in the reactions of the aquatic animal are observed using a camera. In another embodiment, the reactions and changes in the reactions of the aquatic animal are observed using a camera and measured using image analysis software installed on a computer. Images and information related to the reactions and changes in the reactions of the animals can be saved on a computer, machine readable medium, or server, and stored for later analysis.

In another embodiment, the timing and/or magnitude of the stimuli is modulated using software installed on a computer.

In one embodiment, fluid and/or compound is introduced, removed, added, or changed directly to the reaction well by removing the lid. In another embodiment, the reaction well in which the animals are housed includes an inlet, and fluid and/or compound can be added, introduced, or changed via the inlet. In another embodiment, the reaction well in which the animals are housed includes an outlet, and fluid and/or compound can be removed or changed via the outlet. In yet another embodiment, the reaction well contains both and inlet and an outlet, and fluid and/or compound can be introduced and removed using any combination of the inlet, outlet, or directly by removing the lid of the reaction well.

In an eighth aspect, the invention provides a method for screening for compounds that alter morphological, anatomical, or behavioral characteristics of an aquatic animal. The method comprises culturing an aquatic animal in a reaction well capable of housing fluid and an animal and having a transparent viewing surface; exposing said animal to a compound; and observing changes in the morphological, anatomical, or behavioral characteristics of the animal in the presence of the compound versus the absence of the compound, thereby identifying a compound that alters the morphological, anatomical, or behavioral characteristics of the animal. Changes in the morphological, anatomical, or behavioral characteristics of the aquatic animal in the presence versus the absence of compound are observed using a camera and measured using image analysis software installed on a computer. The comparison can be made in the same animal (e.g., morphological, anatomical, or behavioral characteristics in the presence versus the absence of compound in the same animal) or in a separate control animal (e.g., morphological, anatomical, or behavioral characteristics in the presence of the compound in a test animal versus behavior in the absence of the compound in a control animal). One or more compounds that alter the morphological, anatomical, or behavioral characteristics of an aquatic animal are identified as a compound that alters a morphological, anatomical, or behavioral characteristic.

In another embodiment, the compound is selected from a nucleic acid, a peptide, a protein, or a small molecule. Compounds can be supplied individually, or in pools of multiple compounds. Exemplary compounds include, but are not limited to, RNAi constructs, antibodies, antisense oligonucleotides, sense oligonucleotides, peptides, peptidomimetics, small organic molecules, small inorganic molecules, and the like.

In another embodiment, the method comprises a high-throughput method for screening a plurality of compounds in a plurality of reaction wells.

In another embodiment, the behavioral, morphological, or anatomical characteristics of the aquatic animal are observed using a camera. In another embodiment, the behavioral, morphological, or anatomical characteristics of the aquatic animal are observed using a camera and measured using image analysis software installed on a computer. Images and information related to the reactions and changes in the reactions of the animals can be saved on a computer, machine readable medium, or server, and stored for later analysis.

In one embodiment, fluid and/or compound is introduced, removed, added, or changed directly to the reaction well by removing the lid. In another embodiment, the reaction well in which the animals are housed includes an inlet, and fluid and/or compound can be added, introduced, or changed via the inlet. In another embodiment, the reaction well in which the animals are housed includes an outlet, and fluid and/or compound can be removed or changed via the outlet. In yet another embodiment, the reaction well contains both and inlet and an outlet, and fluid and/or compound can be introduced and removed using any combination of the inlet, outlet, or directly by removing the lid of the reaction well.

In one embodiment, the morphological or anatomical characteristic is a change in the rate or extent of regeneration. In another embodiment, the morphological or anatomical characteristic is a change in gene or protein expression. In another embodiment, the morphological or anatomical characteristic is a change in life-span, cell death, cell proliferation, cell differentiation, or cell polarity.

In any of the foregoing methods, an aquatic animal may be labeled to facilitate visualization of the animal and/or visualization or detection of a change in the behavior morphological or anatomical characteristics of the animal. In one embodiment, the label is a fluorescent label. In another embodiment, the label detects gene or protein expression.

In any of the foregoing methods, the compound may be formulated in a pharmaceutically acceptable carrier either prior to administration to test aquatic animals or after identification as a compound that modulates or otherwise affects behavioral, morphological, or anatomical characteristics.

In any of the foregoing methods, experiments may be conducted using one aquatic animal (or fraction thereof) per reaction well. Alternatively, more than one aquatic animal (or fraction thereof) may be housed and screened in a single reaction well. When multiple aquatic animals are housed and assayed in a single reaction well, the invention contemplates that the animals may be labeled, marked, or tagged so that the image analysis software can distinguish between the animals.

Any of the foregoing methods of the invention can be conducted using any of a number of aquatic animals maintained in appropriate fluid. Exemplary aquatic animals are relatively small such that they can be maintained in the amount of space typically available in a traditional laboratory setting. Small aquatic animals include animals of virtually any developmental stage including, but not limited to, embryonic, adult, juvenile, tadpole, larval, and fetal aquatic animals.

In certain embodiments, the aquatic animal is a chordate, hemichordate or protochordate. In one embodiment, the aquatic animal is an invertebrate. In certain embodiments, the aquatic animal is a flatworm. In certain other embodiments, the flatworm is a planarian of the class Turbellaria. Other exemplary aquatic animals that may be housed in these apparatuses include Xenopus embryos and tadpoles, zebrafish, nematodes, amphioxous, sea squirt, and sea urchin embryos and larvae. In certain embodiments, the aquatic animal is an animal fragment. Exemplary fragments can be generated by fission, or by exogenously cutting the animal into one or more fragments (e.g., bisected, trisected, etc). When animal fragments are used, the method comprises assaying for changes in the behavior, morphology, or anatomy of the fragments in the presence versus the absence of one or more compounds.

In a ninth aspect, the invention provides a method for conducting mutagenesis screens or for analyzing putative mutants produced from a mutagenesis screen.

In a tenth aspect, the invention provides compositions comprising one or more compounds identified by any of the methods of the invention. By way of example, the invention provides compositions comprising one or more compounds identified by the methods of the invention as useful in modulating a behavioral, morphological, or anatomical characteristic of an aquatic animal. By way of further example, the invention provides compositions comprising one or more compounds identified by the methods of the invention as useful in modulating learning or memory.

In one embodiment, the composition is a pharmaceutical composition including one or more compounds identified by the methods of the invention and a pharmaceutically acceptable carrier or excipient.

In an eleventh aspect, the invention provides kits. Exemplary kits include any of the apparatuses or systems of the invention, an aquatic animal or a plurality of aquatic animals, and fluid appropriate for housing the particular aquatic animal.

In certain embodiments, the aquatic animal is a planarian of the class Turbellaria. In certain other embodiments, the aquatic animal is a clonal population of planaria.

In certain other embodiments, the kit further includes instructions for use of the apparatus, the system, or the accompanying computer software. In another embodiment, the kit further includes instructions on the care or use of the particular aquatic animal.

In a twelfth aspect, the invention provides a method for training an aquatic animal. The method includes the steps of providing an apparatus for conducting assays in an aquatic animal. The apparatus may include a reaction well capable of housing fluid and the aquatic animal and having at least one, substantially transparent, viewing surface. The apparatus may also include a stimulating element capable of providing a stimulus to the animal in the reaction well and a light source for providing background light to the reaction well. The method also includes the steps of acquiring an image showing the aquatic animal at a first instance in time and measuring based on the image at least one characteristic feature of the aquatic animal. In one embodiment, the step of acquiring an image includes capturing an electronic image using a camera. In one embodiment, the characteristic feature includes at least one of a centroid, a size, a shape, a position, an axis, orientation, a velocity and an acceleration of the aquatic animal. The method further includes the steps of determining a stimulus characteristic of the stimulus based at least on the image and a similar image for another instance in time and controlling the stimulating element to provide a stimulus having the stimulus characteristic to the aquatic animal.

In one embodiment, the method further comprises the step of initializing experimental parameters. The experimental parameters may include at least one of duration of experiment, intensity of background lighting, behaviors of the aquatic animal to be studied.

In one embodiment, the stimulating element includes at least one of a light source, an electrical element, an acoustic element and a chemical releasing element. The stimulus characteristic may include at least one of an intensity, a frequency and a duration of the stimulus. In another embodiment, the step of determining a stimulus characteristic is based at least on the geometric characteristic of the aquatic animal.

The foregoing aspects and embodiments of the invention are equally and generally applicable to screens in any test organism, including a non-aquatic animal or embryo. Thus, in another aspect, the invention provides that any of the foregoing apparatuses, methods, and systems can be used in the context of either aquatic or non-aquatic animals.

The invention contemplates combinations of any of the foregoing aspects and embodiments of the invention.

BRIEF DESCRIPTION OF THE DRAWINGS

The invention may be better understood by referring to the following description of illustrative embodiments, taken in conjunction with the accompanying drawings, in which like reference designations refer to like components and depicted components are not necessarily drawn to scale.

DETAILED DESCRIPTION OF THE INVENTION

(i) Overview

Figure 1:
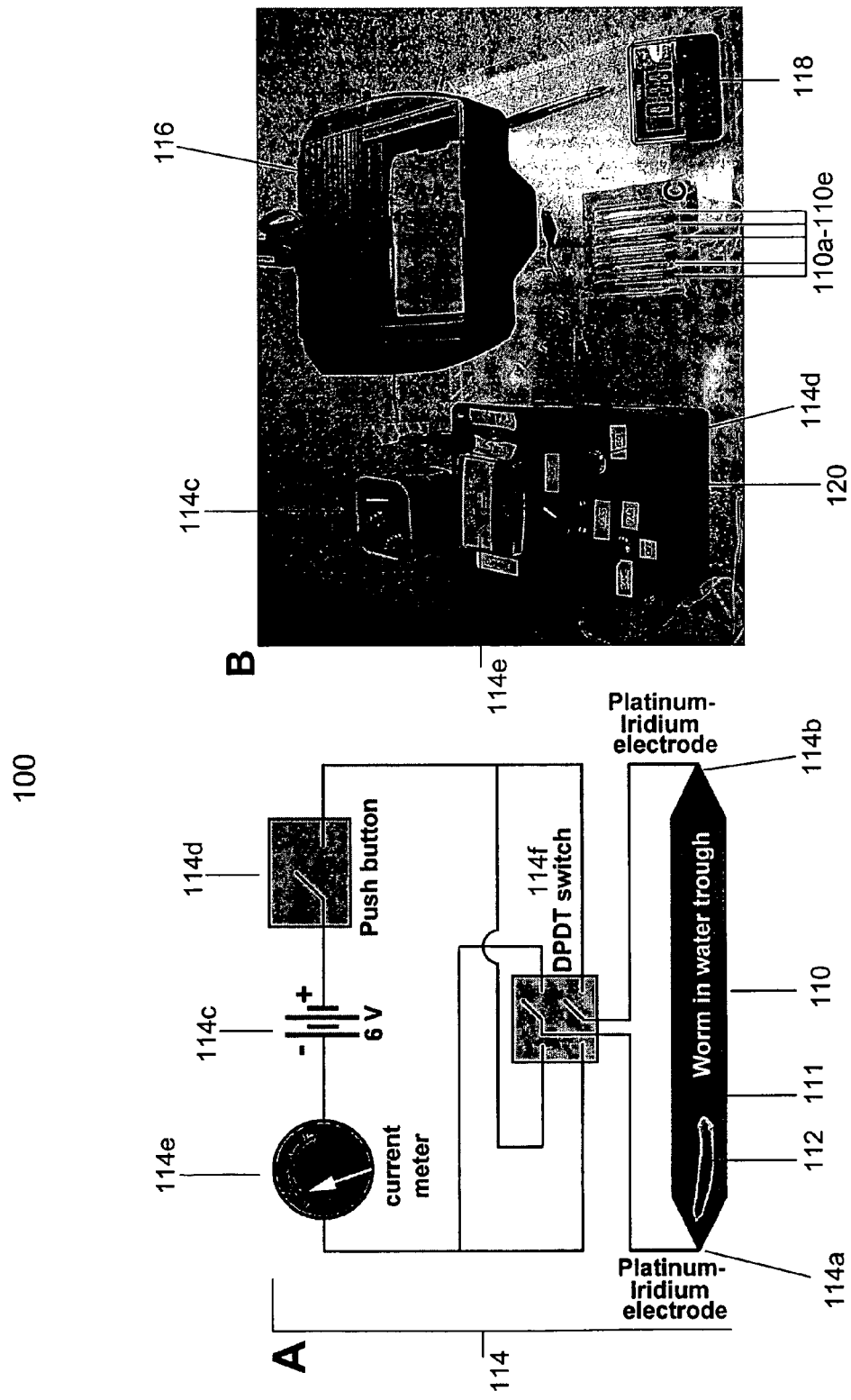
FIGS. 1A and 1B depict an apparatus for delivering a current to an aquatic animal, according to one aspect of the invention.

The present invention provides apparatuses, systems, and methods for conducting assays in test animals. The present invention addresses the limitations of prior art apparatuses, systems, and methods by facilitating well controlled experiments where behavioral, morphological, and anatomical changes can be readily observed and analyzed in an automated fashion with less experimenter bias or error.

(ii) Definitions

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The term "wild type" refers to the naturally-occurring polynucleotide sequence encoding a protein, or a portion thereof, or protein sequence, or portion thereof, respectively, as it normally exists in vivo. The term "wild type" also refers to a phenotypically and genotypically normal organism.

The term "mutant" refers to any change in the genetic material of an organism, in particular a change (i.e., deletion, substitution, addition, or alteration) in a wildtype polynucleotide sequence or any change in a wildtype protein sequence. The term "variant" is used interchangeably with "mutant". Although it is often assumed that a change in the genetic material results in a change of the function of the protein, the terms "mutant" and "variant" refer to a change in the sequence of a wildtype protein regardless of whether that change alters the function of the protein (e.g., increases, decreases, imparts a new function), or whether that change has no effect on the function of the protein (e.g., the mutation or variation is silent). The term "mutant" also refers to an organism with one or more phenotypic or genotypic alterations in comparison to a wild type organism of the same species.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein.

The terms "compound" and "agent" are used interchangeably to refer to the nucleic acids, peptides, polypeptides, or small molecules that can be screened, identified, or characterized for efficacy in modulating cell and/or organismal behavior, anatomy, or morphology using the methods and devices of the invention. Exemplary nucleic acid agents include, but are not limited to, sense or antisense nucleic acids, sense or antisense oligonucleotides, ribozymes, and RNAi constructs. Exemplary peptide and polypeptide agents include growth factors, transcription factors, peptidomimetics, and antibodies. Exemplary small molecules include small organic or inorganic molecules, e.g., with molecular weights less than 7500 amu, preferably less than 5000 amu, and even more preferably less than 2000, 1500, 1000, or 500 amu. One class of small organic or inorganic molecules is non-peptidyl, e.g., containing 2, 1, or no peptide and/or saccharide linkages.

The phrase "conducting assays in aquatic animals" is used to refer to any assays in which an aquatic animal is used as a model system. The term includes assays regardless of whether they are conducted internally to the aquatic animal or externally to the aquatic animal. Additionally, the term includes assays whether the observed readout of the assay is an internal characteristic of the aquatic animal, an external characteristic of the aquatic animal, or both.

The phrases "test animal" and "test organism" are used interchangeably to refer to any animal, regardless of developmental stage, that can be used as a model organism in the present assay system. Suitable test organisms include aquatic animals and non-aquatic animals. Suitable test organisms include adult, embryonic, fetal, tadpole, and juvenile state animals. Suitable test organisms include wildtype and mutant animals.

For purposes of this invention, the chemical elements are identified in accordance with the Periodic Table of the Elements, CAS version, Handbook of Chemistry and Physics, 67th Ed., 1986-87, inside cover.

As used herein, the term "effective amount" means the total amount of the active component(s) of a composition or compound that is sufficient to cause a statistically significant change on a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

Detailed Description of Illustrative Embodiments (i) Detailed Description of Methods and Apparatuses As described above in summary, the invention provides apparatuses, systems, methods, and kits for conducting assays in test animals. The apparatuses, systems, methods, and kits can be used, for example, (i) to conduct screens to identify and/or characterize compounds that modulate behavioral, anatomical, or morphological characteristics of a test animal; (ii) to screen for compounds that alter learning or memory; (iii) to screen for compounds that modulate regenerative capacity of a test animal; (iv) to conduct mutagenesis experiments; and/or (v) to analyze the phenotypes of putative mutants generated by a chemical or radiation-based mutagenesis experiment.

FIG. 1 depicts an apparatus 100 for conducting assays in aquatic animals. FIG. 1A provides a schematic representation, and FIG. 1B shows an apparatus according to one embodiment of the invention. As shown schematically in FIG. 1A, the apparatus 100 includes a reaction well 110. The reaction well 110 houses an aquatic animal 112 and fluid 111 appropriate for maintaining the aquatic animal 112. The apparatus 100 includes an electrical element 114 for delivering an electrical current to the animal 112 in the reaction well 110. As depicted, the electrical element 114 in the reaction well 110 includes two electrodes 114a and 114b that are affixed to the reaction well 110. The electrical element 114 further includes a power source 114c in electrical interconnection with the electrodes 114a and 114b; a control button or switch 114d for starting and stopping the current flowing from the power source 114c to the electrodes 114a and 114b; and a meter 114e for measuring the current supplied to the reaction well 110 via the electrodes 114a and 114b. As shown, the electrical element 114 to the animal 112 in the reaction well 110 includes a double-pole/double-throw switch 114f.

FIG. 1B provides another view of the apparatus 100. Apparatus 100 includes a plurality of reaction wells 110a-110e. The apparatus 100 includes a light source 116 for providing a light stimulus to an aquatic animal 112 in the reaction well 110. The apparatus 100 includes a timer 118 for controlling/measuring various aspects of an experiment. The apparatus 100 includes an electrical element 114 to the animal 112 in the reaction well 110. As depicted in FIG. 1B, the electrical element 114 includes a power supply 114c, a meter 114e, a button or switch 114d. Electrodes 114a and 114b are not visible in the view provided in FIG. 1B. The controller 120 provides a housing for the various components of the electrical element 114. As depicted, the controller 120 includes the button/switch 114d and the meter 114e. The controller 120 also includes circuitry necessary for the electrical interconnection of, for example, the power supply 114c, the meter 114e, the electrode 114a and 114b, and the switch 114d.

The apparatus 100, as depicted in FIG. 1A, includes a reaction well 110 or, as depicted in FIG. 1B, a plurality of reaction wells 110a-10e. The reaction well 110 can be readily sized and shaped to house the particular aquatic animal 112 and fluid 111 required for the particular experiment. As shown, the reaction well 110 is rectangular (e.g., trough-shaped). However, in certain embodiments, the reaction well 110 can be circular or square. Certain circular-shaped reaction wells comprise standard petri-plates, for example, 3 or 6 cm diameter dishes. In certain embodiments of apparatuses including a plurality of reaction wells, the reaction wells comprise standard multi-well plates (e.g., 4-well plates, 6-well plates, 12-well plates, 24-well plates, 48-well plates, 96-well plates).

The size of the reaction well 110 and the aquatic animal 112 being housed will influence the volume of fluid 111 included in the reaction well 110. One of skill in the art can readily determine the appropriate volume of fluid 111 needed to house a particular aquatic animal 112 in a particular reaction well 110. By way of example, an aquatic animal may be housed in approximately 1 ml, 2, 3, 5, 7, 8, 9, or 10 ml of fluid 111. Although in certain embodiments, an aquatic animal may be housed in less than 1 ml (e.g., ½ ml, ¾ ml) of fluid 111 or in greater than 10 ml of fluid 111. Depending on the length of the experiment, the fluid 111 may begin to evaporate. One may optionally add fluid 111 during the experiment, if necessary, to replace fluid 111 lost to evaporation.

Regardless of the size and shape of the reaction well 110 or the plurality of reaction wells 110a-110e, the reaction well(s) may comprise or consist of any of a number of materials. Exemplary materials are substantially inert (e.g., non-reactive) such that they are not harmful to the aquatic animal 112 housed within the reaction well 110. In certain embodiments, the reaction well 110 comprises or consists of glass, lucite, plastic, polypropylene, or polystyrene. In certain embodiments, the interior surface of the reaction well 110 is coated or lined with an inert material or a layer of inert/substantially non-reactive material. By way of example, the interior surface of the reaction well 110 may be lined with or coated with teflon to decrease or prevent any reactivity between the reaction well 110 and the aquatic animal 112.

The reaction well 110 has at least one transparent surface. As depicted in FIG. 1B, the reaction wells 110a-110e are molded or machined from a block of lucite and each reaction well 110 has more than one transparent surfaces, or portions thereof. By transparent surface is meant a substantially transparent surface (e.g., a surface of the reaction well 110 that is sufficiently transparent or translucent such that the aquatic animal 112 may be viewed through that surface using either a camera or the unaided eye).

Although not shown in FIG. 1, the apparatus 100 may include a lid for covering the reaction well 110. The apparatus may contain a single lid or a plurality of lids. Furthermore, the apparatus may contain a means for reversibly securing the lid or lids to the apparatus. Exemplary means for securing a lid include, but are not limited to, one or more clips, snaps, screws, nails, or magnetic portions attached to both the lid and the apparatus. Additionally, the lid may have a transparent viewing surface to allowing observation of the animal through the lid. The transparent viewing surface may be an entire surface of the lid. Alternatively, the transparent viewing surface may be a portion of a surface of the lid.

The reaction well 110 is sized and shaped to house (e.g., to contain during the course of the experiment) an aquatic animal 112. As depicted, the aquatic animal 112 is a single flatworm (e.g., one aquatic animal/reaction well). However, the invention contemplates that the reaction well 110 can be used to house any of a variety of aquatic animals 112 of any of a variety of developmental stages. Additionally, the reaction well 110 can be used to house whole organisms, substantially whole organisms, or animal fragments. In certain embodiments, multiple aquatic animals are housed in a single reaction well. When multiple animals are housed in a single reaction well, the animals may be optionally tagged, marked, or otherwise labeled to help unambiguously identify them.

Regardless of the particular aquatic animal 112, the reaction well 110 houses both the aquatic animal 112 and fluid 111. The fluid 111 is appropriately chosen to maintain the particular animal 112 under study. Exemplary fluids 111 include, but are not limited to, spring water, salt water, deionized water, and culture medium.

The apparatus 100 includes an electrical element 114 for delivering an electrical current to an aquatic animal 112 in the reaction well 110. As depicted in FIG. 1A, the means for delivering an electrical current 114 includes a pair of electrodes 114a and 114b. The electrodes 114a and 114b are in electrical interconnection with a power source 114c. As depicted, the power source 114c is a 6V battery. The supply of power between the power source 114c and the electrodes 114a and 114b is modulated by a button or switch 114d, and a meter 114e displays the current flowing through the circuit. As depicted in FIG. 1B, the electrical element 114 includes a controller 120. The controller 120 houses various aspects of the electrical element 114.

As depicted, the electrodes 114a and 114b are platinum-iridium electrodes. Platinum-iridium electrodes are useful because they do not produce electrolysis products that may interfere with the experiment or otherwise harm the aquatic animal 112. However, and in other embodiments, the electrodes 114a and 114b may be composed of or coated with other materials having similar properties. Exemplary electrodes may be made of or coated with platinum, platinum-iridium, or titanium.

As depicted, the electrical element 114 includes a pair of electrodes 114a and 114b. However, in other embodiments, the means for delivering an electrical current 114 includes a wire mesh affixed to an interior surface of the reaction well 110 or the interior surface of the lid. All that is necessary is that the means for delivering an electrical current 114 includes an element that is (i) in electrical interconnection with a power source and (ii) extends into the reaction well, for example, into the fluid in the reaction well. Numerous possible configurations exist and are contemplated The apparatus 100 also includes a light source 116. As depicted, the light source 116 comprises a magnifier lamp. The light source 116 can be used to provide a light stimulus to the aquatic animal 112 in the reaction well 110. In other embodiments, the light source 116 is provided by, for example, one or more light bulbs of a selected wattage or an LED light. As depicted in FIG. 1B, the light source 116 is separate from a lid, shield, or other element of the apparatus 100. However, in certain embodiments, the lid or shield includes the light source 116. Additionally, although not shown in FIG. 1, the apparatus 100 may also include a light source for providing background light.

Although not shown in FIG. 1, the reaction well 110 may include an inlet and/or an outlet extending from the exterior into the reaction well 110. When present, an inlet can be used to introduce or add fluid and/or compounds to the reaction well 110. When present, an outlet can be used to remove or change fluid, waste products, and/or compounds from the reaction well. Regardless of whether the reaction well 110 includes an inlet and/or an outlet, fluids and compounds can be introduced, added, removed, or changed directly by removing the lid (when present) from the reaction well 110. When present, as inlet and/or outlet may include a valve or stopper to prevent inadvertent leakage of fluid Although not depicted in FIG. 1, the apparatus may optionally include a shield. The term shield refers to any covering designed and used to exclude external (e.g., not related to the experiment) light, sound, and/or vibration from the reaction well 110. In certain embodiments, the shield may form a portion of the lid. Furthermore, the shield may include one or more light sources (e.g., for delivering a light stimulus or for providing background light). The term shield applies to a covering intended to decrease external light, sound, and/or vibration. Although certain shields and shield configurations may exclude substantially all external light, sound, and/or vibration, other shields and shield configurations may exclude only a portion of the external light, sound, and/or vibration. The term applies equally to any of these shields.

An exemplary use of the apparatus 100 in a learning experiment is provided in Example 1. However, the apparatus 100 can similarly be used in screening assays, for example, screens to identify compounds that alter memory, learning, behavior, morphology, regeneration, or anatomy.

As depicted, apparatus 100 is used for containing an aquatic animal during the course of an experiment. However, in certain embodiments, apparatus 100 can be readily adapted for use with any test organism, including a non-aquatic animal. When used in the context of a test animal that is not an aquatic animal, the animal is not maintained in a fluid within the reaction well. In certain embodiments, the animal may be maintained on a solid or semi-solid surface within the reaction well. For example, the animal may be maintained on a layer of agar, wax, mesh, soil, grass, or other suitable non-liquid surface. The other features and uses of the apparatus described herein similarly apply regardless of whether the test organism is an aquatic or a non-aquatic animal.

FIG. 2A depicts an apparatus 200 and FIG. 2B depicts a system 201 according to another embodiment of the invention. The apparatus 200 includes a reaction well 110 which is largely as described above for apparatus 100. The reaction well 110, which in this embodiment is made from glass, houses an aquatic animal 112 in an appropriate fluid 111. The reaction well 110 includes an electrical element, and the electrical element includes a pair of electrodes 114a and 114b. As depicted, the reaction well 110 includes a pair of electrodes 114a and 114b affixed to opposite ends of the reaction well 110. Although not shown, the pair of electrodes 114a and 114b can be in electrical interconnection with, for example, a circuit board, power supply, battery, or the like. As outlined above, all that is necessary is that the electrical element is (i) in electrical interconnection with a power source and (ii) extends into the reaction well, for example, into the fluid in the reaction well. Exemplary alternative configurations of the means for delivering an electrical current 114 are described for FIG. 1.

The apparatus 200 further includes a lid 222. The lid 222 can reversibly cover the reaction well 110. In certain embodiments, the lid 222 may include any of a circuit board, light sources, an electrical element, and the like. As depicted, the lid 222 includes a transparent surface. However, this need not be the case. The utility of the transparent surface of the lid 222, according to this embodiment, is discussed below.

The apparatus 200 further includes a shield 224. As depicted, the shield 224 comprises an opaque cone that sits atop the lid 222 and helps shield the aquatic animal 112 in the reaction well 110 from external light, sound, and/or vibration. The shield 224 includes a light source 116 affixed to the top, interior edge of the shield 224. As depicted, the light source 116 is a light source for providing a light stimulus. The specific light source 116 is a white LED light. However, other light sources 116 of various intensities can be readily selected. In this configuration, the light source 116 is affixed to the shield 224, and thus the use of a lid 222 with a transparent surface is desirable. In alternative configurations, the light source 116 is affixed to the interior of the lid 222, and thus the lid need not contain a transparent surface. In still other embodiments, the light source 116 is separate from both the lid 222 and the shield 224.

Although not shown, the light source 116 can be interconnected to, for example, a circuit board, power supply, and the like. Other features and configurations of light sources 116 are as described above and throughout the application.

Although not shown, the apparatus may further include a light source for providing background light. Such a light source can, for example, be affixed to the lid 222 or the shield 224.

Although not shown, in certain embodiments the reaction well 110 may contain an inlet and/or an outlet; the features of which are described in detail above.

FIG. 2B provides a system 201. The system 201 includes a plurality of apparatuses 200. Specifically, the system 201 includes a plurality of reaction wells 110a-d. Each of the plurality of reaction wells 110a-d includes an aquatic animal 112a-d housed in the appropriate fluid 111a-d. Each of the plurality of reaction wells includes an electrical element, light sources 116a-d, lids 222a-d, and shields 224a-d. The system 201 further includes a box 226 and a camera 228. As shown, the system 201 sits on the top surface of a table 230.

As depicted, the apparatuses sit on the top surface of a plexiglass box 226 so that the bottom surfaces of the reaction wells 110a-d rest on the top surface of the plexiglass box 226. In certain embodiments, each reaction well 110 is aligned in a tray containing slots sized and shaped to accommodate the reaction wells 110a-d. When such a tray is used, the tray can be placed on the top surface of the plexiglass box 226. In either configuration, the bottom surface of the reaction well 110 or wells 110a-d can be viewed from within the plexiglass box 226. In other embodiments, the box 226 is made from other materials of similar strength. An exemplary box 226 must have at least one transparent surface to facilitate capturing of images by a camera 228 contained with the box 226.

As depicted, a single camera 228 is placed within the plexiglass box 226. The camera is configured with its lens facing the bottom surfaces of the reaction wells 110a-d, thereby allowing the camera to capture images by viewing through the bottom surface of the reaction wells 110a-d. As shown, a single camera 228 is used to capture images from multiple reaction wells 110a-d. Alternatively, multiple cameras or photoelements can be used. Multiple cameras or photoelements can be used to each capture images from a single reaction well 110. Multiple cameras or photoelements can also be used to each capture images from multiple reaction wells. Furthermore, and depending on the configuration of other elements of the apparatus and system, the camera or photoelement may be oriented to capture images through the top surface of the reaction well 110 or through a lateral surface of the reaction well. Note that to capture images through a particular surface of a reaction well 110, that surface of the reaction well 110 must be or contain a transparent surface or portion.

For any of the foregoing, the camera 228 may be, for example, a digital USB2 camera. In certain preferred embodiments, the camera 228 or photoelement includes a far-red filter and an infrared light source. This long-wavelength light is out of the range of, for example, the vision of flatworms. Alternatively filters can be chosen, if necessary, depending on vision characteristics of the selected aquatic animal 112. Thus, the camera 228 can take continuous images without inadvertently providing a light stimulus to the aquatic animal 112. The use of a digital camera is desirable because such digital images can be immediately stored and evaluated using software installed on a computer.

Figure 2:
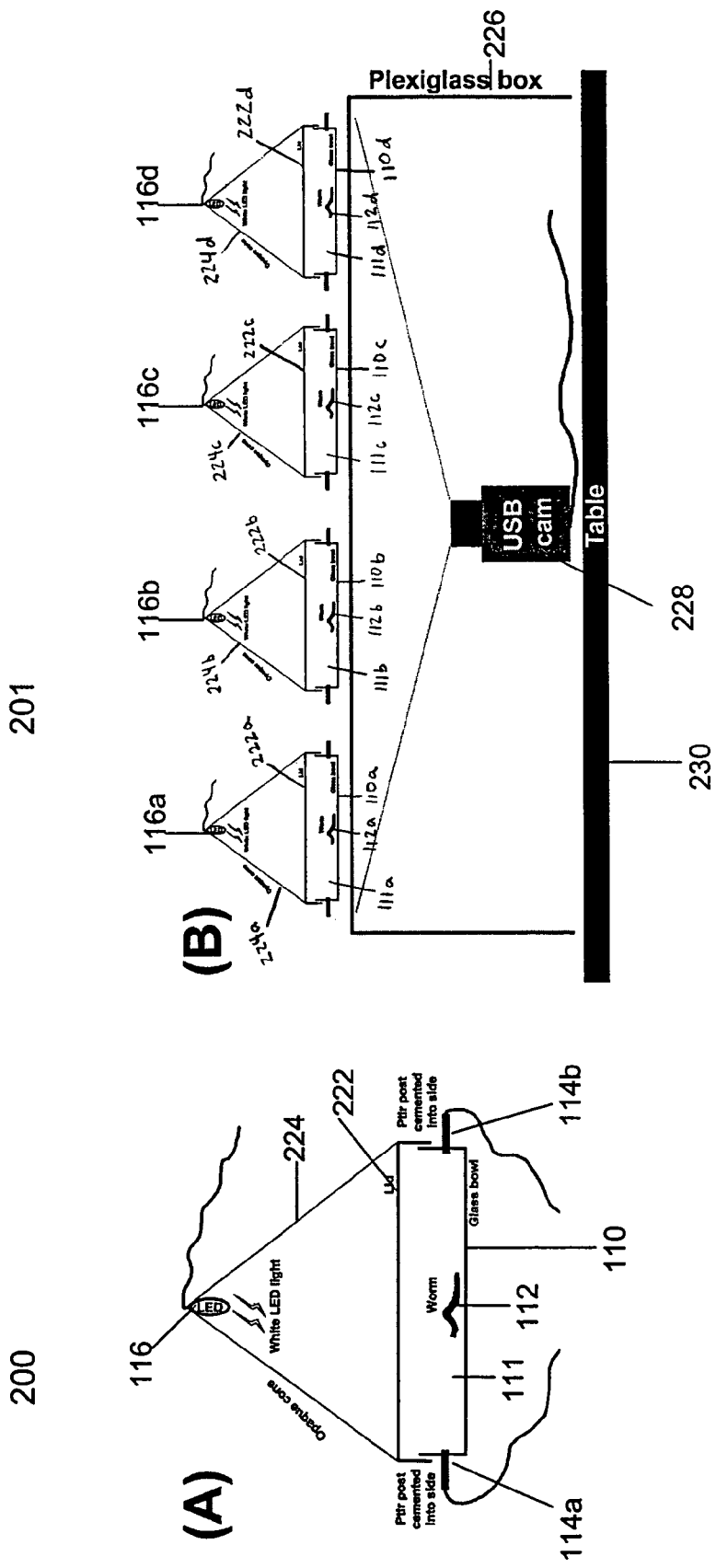
FIGS. 2A and 2B depict schematic representations of an apparatus and system, according to another embodiment of the invention.

Although not depicted in FIG. 2, the system 201 may also include an interface box. The interface box is, for example, an addressable digital-analog converter. The interface box can be interconnected to a computer (e.g., a PC-based computer), as well as to the light source, the electrical element, circuit board, etc. The interface box allows interconnection between the computer, which is installed with appropriate software for image recognition and control of experimental parameters, and the various means used to control experimental parameter (e.g., electrodes, light sources, etc). This feature will be illustrated in more detail below.

Apparatus 200 and system 201 can be readily adapted for use with any test organism, including a non-aquatic animal. When used in the context of a test animal that is not an aquatic animal, the animal is not maintained in a fluid within the reaction well. In certain embodiments, the animal may be maintained on a solid or semi-solid surface within the reaction well. For example, the animal may be maintained on a layer of agar, wax, mesh, soil, grass, or other suitable non-liquid surface. The other features of the apparatus and system similarly apply regardless of whether the test organism is an aquatic or a non-aquatic animal.

FIG. 3A depicts an apparatus 300, according to another embodiment of the invention. The apparatus 300 includes a reaction well 110 and a lid 222. In this view, only a single electrode 114a is visible. However, an exemplary reaction well 110 includes a pair of electrodes for delivering an electrical current. The apparatus includes an inlet 332 and an outlet 334. The inlet 332 and the outlet 334 can extend into the reaction well 110. The inlet 332 can be used to add or introduce fluid and/or compound to the reaction well, and the outlet 334 can be used to remove or change fluid and/or compound. However, even when the apparatus 300 includes an inlet 332 and/or an outlet 334, fluid and/or compound can be added, introduced, removed, or changed directly by removing the lid 222 covering the reaction well 110. In certain embodiments, the inlet and/or outlet includes a stopper or valve to prevent inadvertent leakage of fluid.

Figure 3:
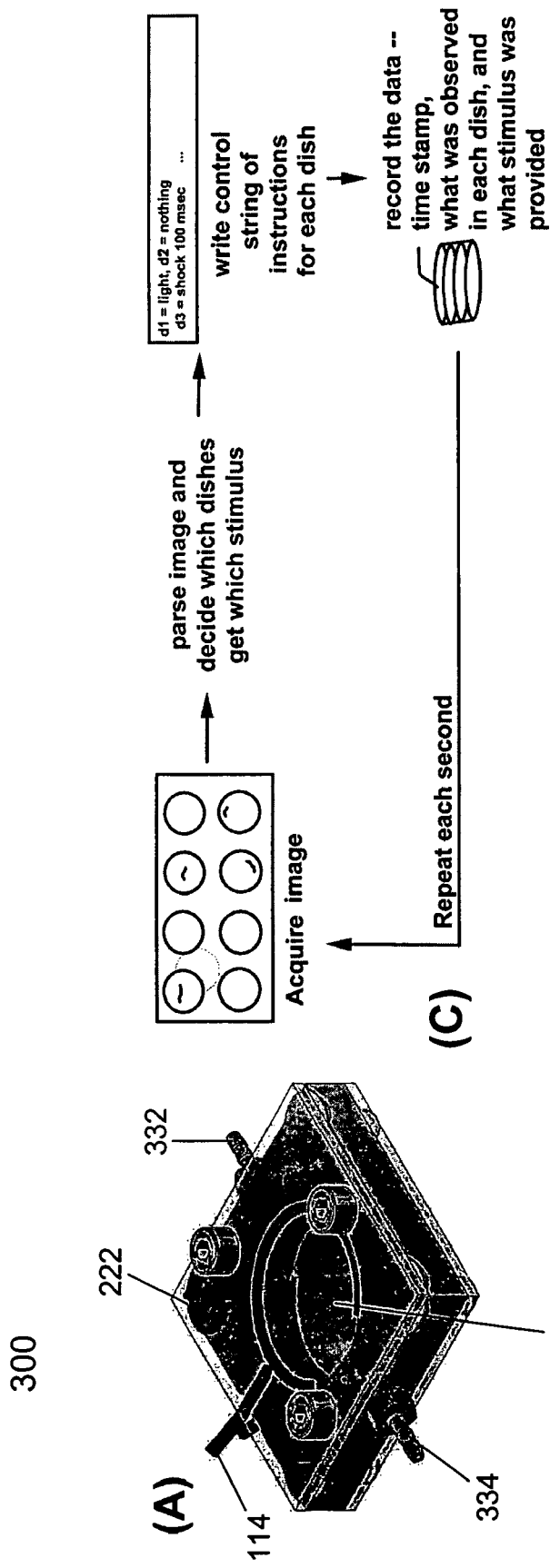
FIG. 3A depicts an apparatus including a single reaction well, according to one embodiment of the invention.
FIG. 3B provides a flow diagram depicting a method for studying an aquatic animal.
FIG. 3C represents an algorithm for conducting a behavioral experiment in an aquatic animal. When used in conjunction with image recognition software, the algorithm allows the investigator to observe behavior, supply various stimuli to particular reaction wells, and stamp the captured images for later identification.
Figure 3B:
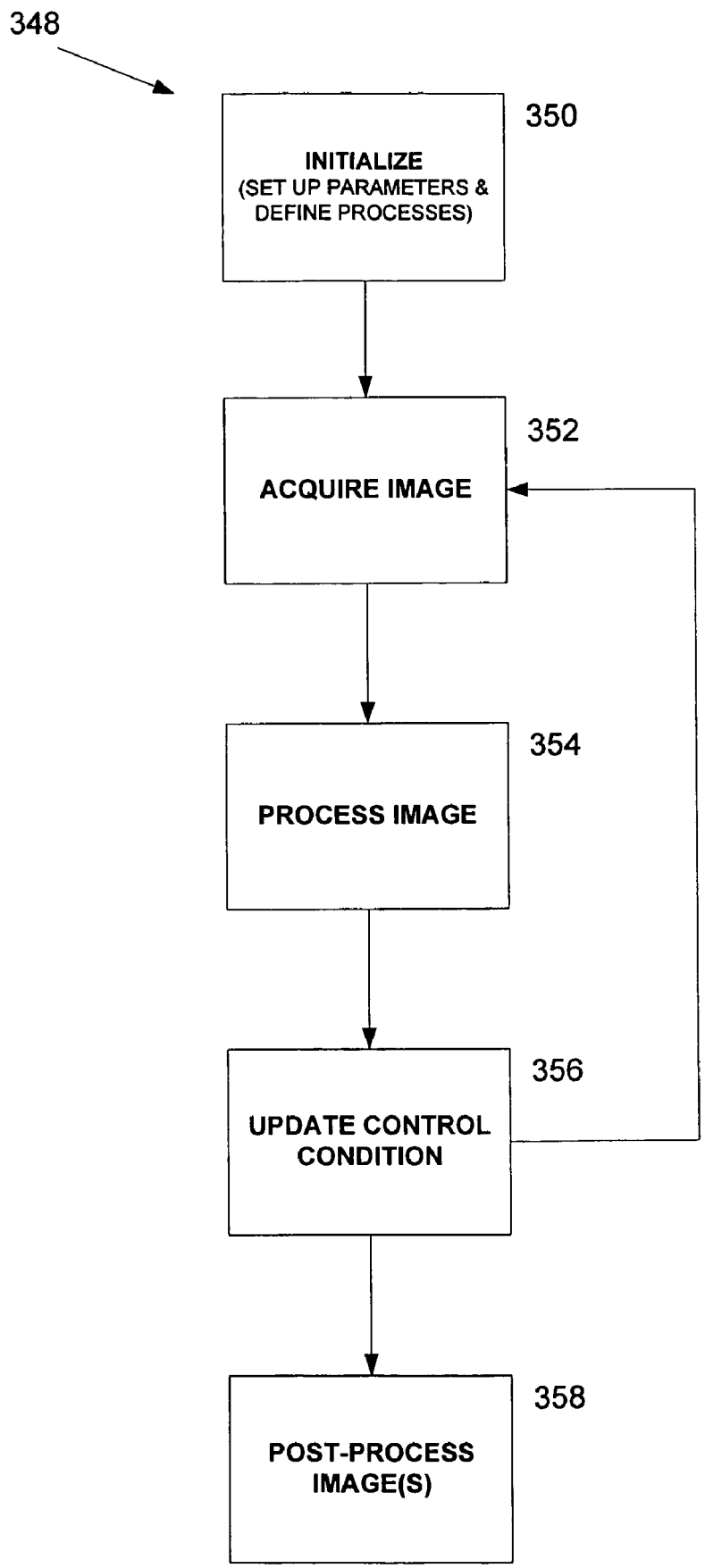

FIG. 3B is a flow diagram depicting a method 348 for studying an aquatic animal using systems 200, 201 and 300 of FIGS. 2 and 3. The method begins with the step of initializing one or more experimental parameters and processes (step 350). An imaging system having a camera then acquires an image of the aquatic animal in the system (step 352). A computer, having suitable software, connected to the imaging system processes the acquired image to filter out certain features and to extract certain other characteristic features of the aquatic animal (step 354). The software makes a decision as to whether a stimulus is to be applied to the aquatic animal based, at least in part, on any changes in the aquatic animal's behavior or lack thereof (step 356). Steps 352, 354 and 356 correspond to a particular instance in time and are repeated a suitable number of times depending on the duration of the experiment and the desired frequency of measurement. The computer may then post-process the image(s) obtained from one or more instances in time (step 358). Post-processing includes performing statistical analysis.

Generally prior to the beginning of experimentation and sometimes during experimentation, certain parameters and processes are initialized. In certain embodiments, the parameters include experimental parameters such as rate of fluid flow within the reaction well and into and out of the reaction well, desired background lighting in the reaction well and timing of the experiment. Other experimental parameters include a stimulus characteristic such as the intensity of a light source or voltage generated by an electrical element such as an electrode. In addition certain threshold parameters may be initialized. For example, an expected behavior of the aquatic animal may be initialized such that it serves as a threshold parameter. During the experiment, if such an initialized behavior is observed, the software may recommend a change in certain experimental parameters. As an example, if the aquatic animal is behaving in a undesired manner, then an electrical shock may be delivered under the command of the computer software to the aquatic animal to train it.

The imaging system typically includes an excitation source and a camera connected to a computer terminal. During operation, radiation from the excitation source may impinge on the aquatic animal in the reaction well. Reflected and/or refracted light from the animal may be captured digitally by the camera. The image so obtained may be sent to a computer having suitable software for further analysis and display.

In one embodiment, the camera captures an image (step 352) of a portion of the reaction well containing the aquatic animal. The camera may be configured to capture a series of images that may be combined to produce a video. In one embodiment, the camera is configured to capture 30 images (frames) per second (such a frame rate may be suitable for smooth video streaming). The captured image is then sent to a computer for processing and analysis. In certain embodiments, the reaction well may include a plurality of aquatic animals. In such an embodiment, the characteristic features from each of the plurality of aquatic animals are extracted. The plurality of aquatic animals may be distributed throughout the reaction well and consequently appear as a set of shapes distributed throughout each acquired image. The acquired image typically comprise a two dimensional plot having one or more aquatic animal that forms (may be approximated with geometric shapes such as rectangles and triangles to represent the aquatic animal) points (centroids) at different locations on the diagram. The aquatic animals may keep moving from one location in the reaction well to another. Each image may be acquired at a different instance in time and therefore, each acquired image may have a different distribution of aquatic animals.

The acquired/captured image is then processed using the computer software (step 354). The captured image may be divided into smaller regions based on the locations of aquatic animal and certain other desired locations as required by the application. Desired characteristics of the acquired images including characteristic features of the aquatic animal such as the location of the center of gravity of the aquatic animal, the size, shape, axes, orientation, velocity and acceleration of the aquatic animal may be extracted. In certain embodiments, characteristic features are extracted from a portion of aquatic animals in the reaction well. Processing an acquired image may include other techniques in image enhancement and image processing such as background subtraction, binary conversion, filtering, compression and coding without departing from the scope of the invention. In certain embodiments, during an experiment, the aquatic animal may be positioned along the walls of the reaction well and thus not easily discernable. In such embodiments, the software is programmed to identify the presence of an aquatic animal along the reaction walls as well as determine on which wall the aquatic animal is positioned and in what orientation.

The computer system is also connected to a stimulating element for imparting a stimulus on the aquatic animal in the reaction well (step 356). The stimulating element may include a light source, an electromagnetic radiation source, an electrical element capable of generating an electric field or an acoustic element capable of generating an acoustic wave. Further stimulating elements may include a mechanism for imparting vibration to an animal in a reaction well, for example, using a piezo-electric element. In one embodiment, the computer software controls the operation of the stimulating element. The software makes a decision for an aquatic animal based at least in part on the parameters and processes defined earlier in step 350. In one embodiment, the computer software writes a command-string to an external device such as a stimulating element. The command string includes instructions for either taking an action and imparting a stimulus, or taking no action. In certain embodiments, the command string includes instructions for controlling the duration of the stimulus, the intensity of the stimulus and location of the stimulus. In certain embodiments, the system includes a plurality of stimulating elements. In such embodiments, the command string includes instructions for controlling one or more of the plurality of stimulating elements independently.

In one illustrated embodiment, the image is further processed after the completion of the experiment (step 358). In such an embodiment, the processed images from one or more instances in time are combined in a computer or by a user to generate continuously playing movies. The computer or user may also combine images from different reaction cells or from different experiments. A computer or user may perform point statistical analysis of either the processed images or the acquired images or both. Other techniques in image processing and statistical analysis may be implemented during the experiment or after without departing from the scope of the invention.

FIG. 3C depicts an example of the method 348 of FIG. 3B. In particular, FIG. 3B provides a training algorithm. As depicted, the training algorithm consists of a reiterative loop performing the following steps. An image is obtained of the aquatic animal in their reaction well. The system of FIG. 3C shows eight reaction wells, some having an aquatic animal therein. In other embodiments, the system includes a plurality of reaction wells greater than or less than eight. A plurality of images may be obtained from the plurality of cells depicted in FIG. 3C. In certain embodiments, a single image is obtained from the plurality of cells. The image is parsed, for example, using fairly simple image analysis tools present in the Matlab software package. Each animal's position is estimated. The software then makes a decision (based on the details of the experiment as defined by the user before the start of the run) for each animal, as to whether the animal is to be rewarded (e.g., by lowering a light stimulus), punished (e.g., by receiving an electrical shock/current), or receive no action (e.g., a control condition). The position of each animal along with the action taken is recorded as a time-stamped record in a database. The process continues until the experiment is terminated (e.g., hours, days, weeks).

In certain embodiments, the stimulating element and/or the excitation source includes a pulsed light source. In other embodiments, the stimulating element and/or the excitation source includes an arc lamp, an incandescent bulb which also may be colored, filtered or painted, a lens end bulb, a line light, a halogen lamp, a light emitting diode (LED), a chip from an LED, a neon bulb, a fluorescent tube, a fiber optic light pipe transmitting from a remote source, a laser or laser diode, or any other suitable light source. Additionally, the, the stimulating element and/or the excitation source may be a multiple colored LED, or a combination of multiple colored radiation sources in order to provide a desired colored or white light output distribution. For example, a plurality of colored lights such as LEDs of different colors (red, blue, green) or a single LED with multiple colored chips may be employed to create white light or any other colored light output distribution by varying the intensities of each individual colored light. The stimulating element and/or the excitation source may include a ring of LEDs to generate a circular source of light.

The light from the reaction well is collected by a camera. The camera includes Charge-coupled devices (CCD) video sensor chip. The CCD converts the image into an electrical signal and sends it to a computer where it can be processed.

The computer may include an image processor. The image processor may include a microprocessor or microcontroller that is programmed to process digital information from the CCD camera video sensor chip. The image processor includes software algorithms for performing other functions such as identification of the aquatic animal in the reaction well, and keeping track of the aquatic animal.

The computer may also include any computer system having a microprocessor, a memory and a microcontroller. The memory typically includes a main memory and a read only memory. The memory may also include mass storage components having, for example, various disk drives, tape drives, etc. The mass storage may include one or more magnetic disk or tape drives or optical disk drives, for storing data and instructions for use by the microprocessor. The memory may also include one or more drives for various portable media, such as a floppy disk, a compact disc read only memory (CD-ROM), or an integrated circuit non-volatile memory adapter (i.e. PC-MCIA adapter) to input and output data and code to and from microprocessor. The memory may also include dynamic random access memory (DRAM) and high-speed cache memory.

As noted earlier, the image of the aquatic animal in the reaction well is acquired using a camera. The camera typically captures a portion of the reaction well that may define an observation window. Aquatic animals within the bounds of the observation window may be observed by the imaging system including the camera. During imaging of the reaction well, a plurality of aquatic animals may move in and out of the observation window. Therefore, in addition to observing the paths of organisms already within the observation window, the imaging system may identify and observe organisms just entering the window.

In one embodiment, based on the information obtained and processed, the software can automatically analyze the data collected for each animal or for each group of experimental animals. By way of example, the software can process the data and generate any of the following: the percentage of the time test animals spend in the proper place following a training regimen (e.g., a measure of learning); the number of punishments delivered as a function of time; the percentage of the time test animals spend in light versus dark; the percentage of time test animals spend in various sections of the reaction well (e.g., bottom of well versus edge of well); the latency period; the time before the test animals achieves a given number (N) correct responses. By way of further example, the software can generate measurements of average animal speed or activity level.

The software and computer system can be readily adapted for use with any test organism, including non-aquatic animals.

Figure 4:
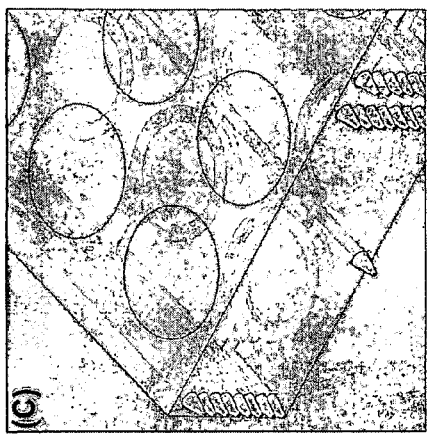
FIGS. 4A-4C depict various configurations of apparatuses that include a plurality of reaction wells, according to another embodiment of the invention.
Figure 4:
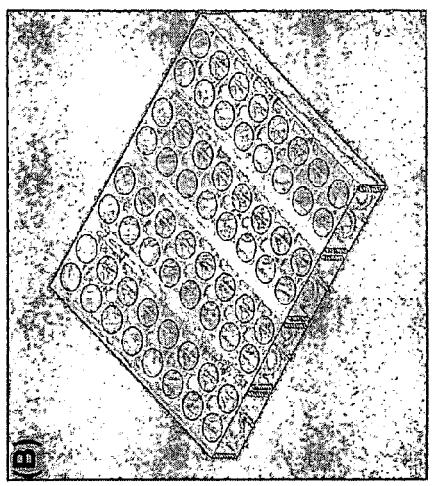
Figure 4:
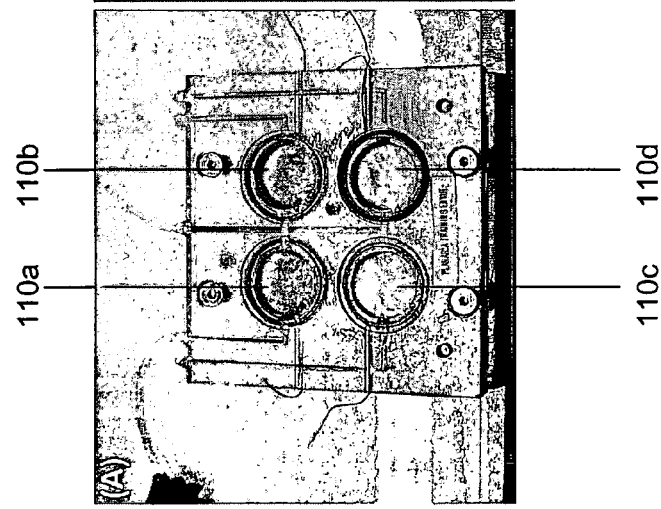

FIGS. 4A-4C depict various multi-well configurations for apparatuses of the invention. FIG. 4A depicts an apparatus 400. The apparatus 400 includes four reaction wells 110a-110d. The reaction wells 110a-110d are circular-shaped reaction wells. FIG. 4B depicts an apparatus 401. The apparatus 401 includes 64 reaction wells arrayed in an 8 reaction well X 8 reaction well configuration. As shown, each of the reaction wells of the apparatus 401 is smaller that each of the reaction wells 110a-110d of the apparatus 400. FIG. 4C provides a close-up view of an apparatus 402.

Apparatuses 400, 401, and 402 illustrate that the size, shape, and configuration of the reaction wells and apparatuses of the invention can be readily selected or modified depending on the needs of the particular experiment or investigator.

Figure 5:
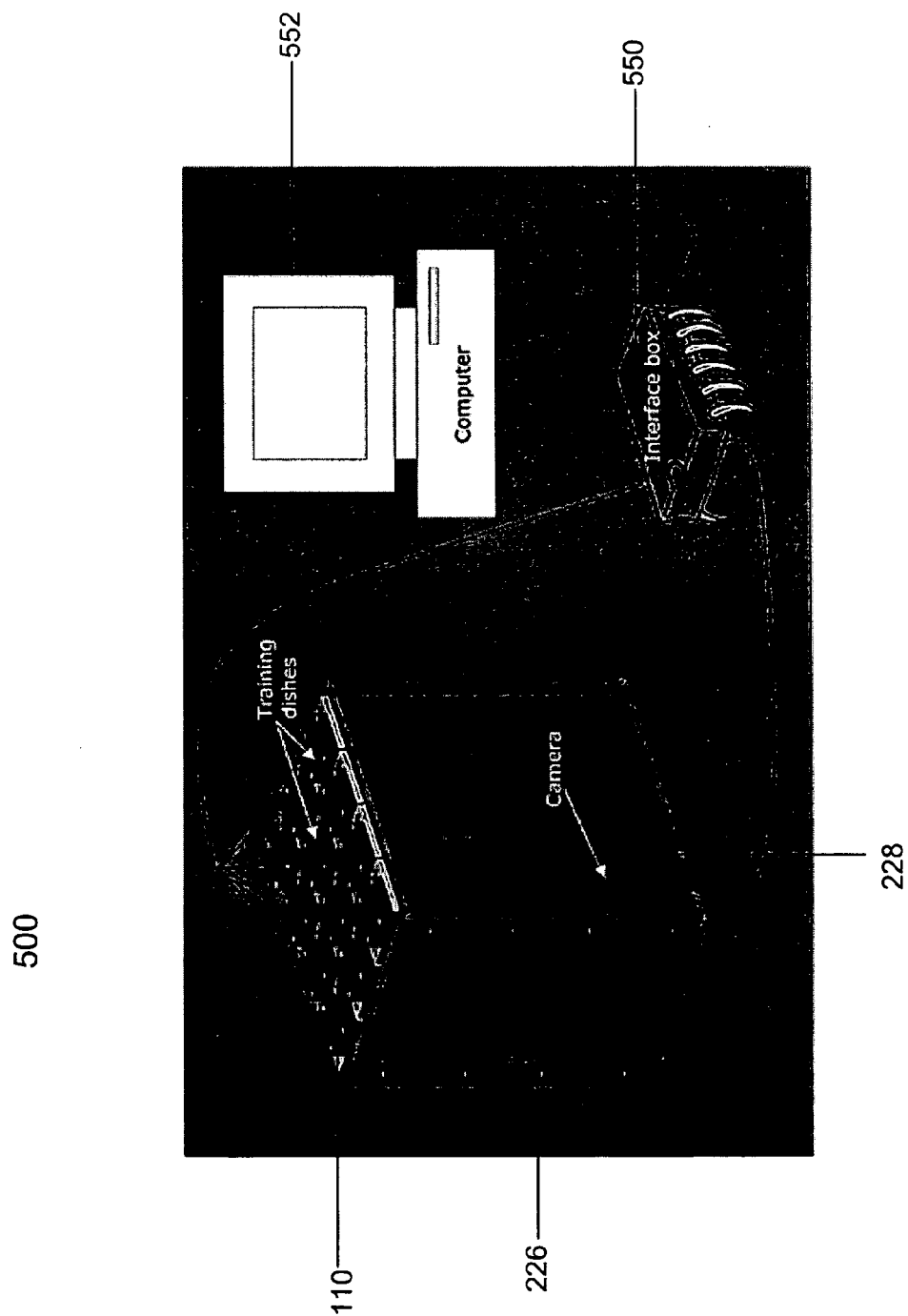
FIG. 5 depicts a system, according to another embodiment of the invention.

FIG. 5 depicts a system 500, according to another embodiment of the invention. The system 500 includes an array of 12 reaction wells; each of which is equivalent to a reaction well 110. Each reaction well 110 can house an aquatic animal and fluid. The reaction wells sit atop a plexiglass box (e.g., or other similarly stable and substantially transparent material) 226. The bottom surface of each reaction well 110 sits atop the top surface of the box 226. The reaction wells can be placed atop the box 226. Alternatively, the reaction wells can be aligned in a tray containing slots sized and shaped to accommodate the reaction wells. Although not shown in detail in FIG. 5 each reaction well 110 is covered with a lid.

The system 500 further includes a camera 228 contained within the box 226. As depicted, the system includes a single camera 228, and the single camera 228 can be used to capture images from each of the reaction wells 110. Alternatively, the systems can include multiple cameras. The camera 228 is oriented so that the lens of the camera 228 can readily capture images of the animal in the reaction wells.

The system 500 also includes an interface box 550. As described above, the interface box 550 is a converter to facilitate communication between the computer 552 and the other elements of the system 500. As illustrated in FIG. 5, the computer 552 and the camera 228 are in operable interconnection with the interface box 550, and the interface box 550 is in operable interconnection with elements of the apparatus that control parameters administered to the reaction well 110. For example, the interface box 550 can be in interconnection with a circuit board, and thereby be in interconnection with one or more light sources and/or electrical elements.

Figure 6:
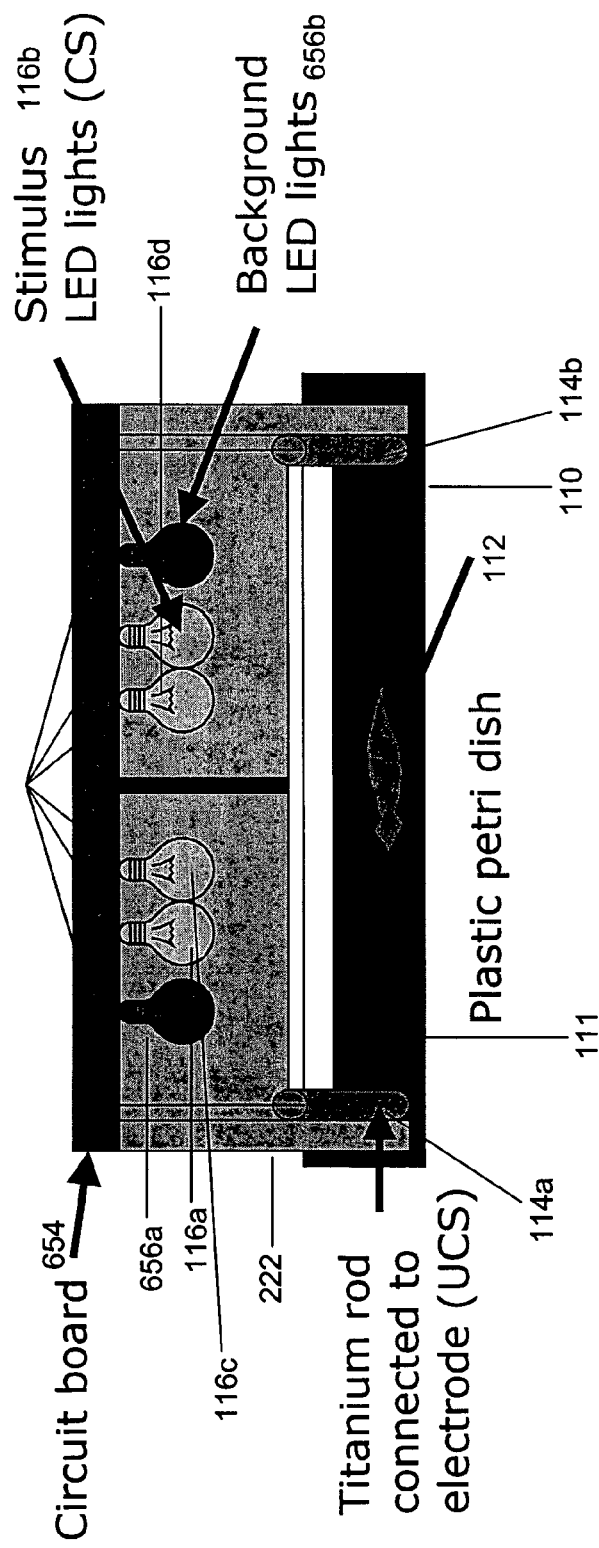
FIG. 6 provides a schematic representation of an apparatus, according to one embodiment of the invention.

FIG. 6 depicts a schematic representation of an apparatus 600. The apparatus 600 includes a reaction well 110. The reaction well 110 can house an aquatic animal 112 and an appropriate fluid 111. The reaction well 110 can be reversibly covered with a lid 222. As shown, many of the features of the apparatus 600 are included in the lid 222. In other embodiments, all or some of these features can be included, for example, in a shield. Alternatively, all or some of these features can be separate from the lid or the shield.

The apparatus 600 includes light sources for supplying a light stimulus 116a-d. As depicted, the light sources for supplying a light stimulus 116a-d are included in an interior surface of the lid 222. The apparatus 600 also includes multiple lights sources for providing background light 656a-b. As depicted, lights sources 656a-b are included in an interior surface of the lid 222.

The apparatus 600 also includes electrical element 114 for delivering electrical current to the reaction well 110. As depicted, the electrical element includes a pair of electrodes 114a and 114b. In this embodiment, the pair of electrodes are affixed to the lid 222 so that the electrodes 114a and 114b are brought into contact with the fluid 111 in the reaction well 110 when the lid 222 covers the reaction well 110. In other embodiments, the electrical element 114 can be affixed to, for example, the lateral interior surfaces of the reaction well 110 or the bottom interior surface of the reaction well 110.

As depicted, each of the lights sources 116a-d, and 656a-b, and the pair of electrodes 114a and 114b are in operable interconnection with a circuit board 654. As shown, the circuit board 654 comprises the top surface of the lid 222.

In the embodiment represented in FIG. 6, the lid 222 further serves as a shield for decreasing external light, sound, or vibration. Note that the lateral surfaces of the lid 222 are substantially opaque, and the top surface of the lid 222 includes the circuit board 654. Thus, in certain embodiments, the apparatus need not include a separate shield, but rather the lid 222 can possess shield-like properties. Note that although in certain embodiments, a shield can be used to decrease external vibration, in other embodiments external vibrations are used as a stimulus and are specifically generated for use as a stimulus to the test organism.

Figure 7:
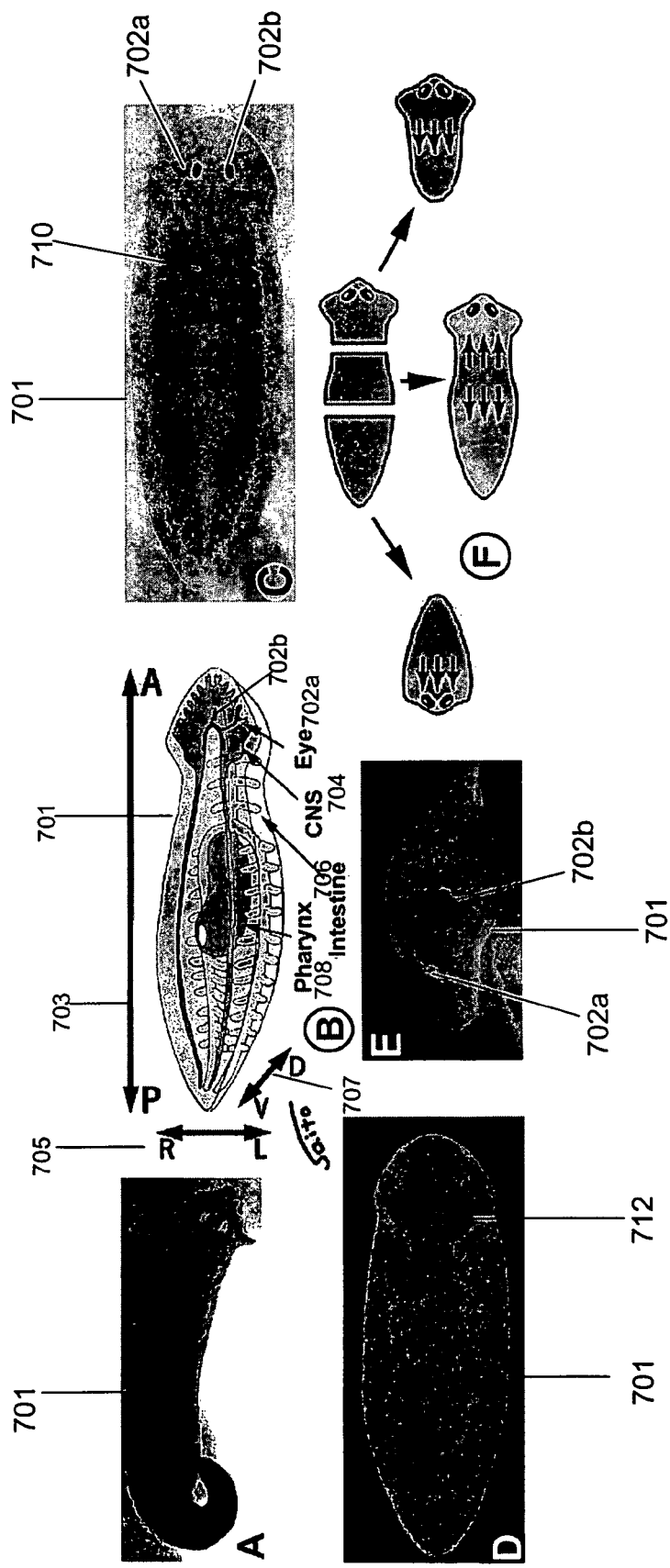
FIGS. 7A-7F show an aquatic animal suitable for use, according to any of the methods, apparatuses, and systems of the invention.

FIGS. 7A-7F depict an example of an aquatic animal that can be housed in the apparatuses and systems of the invention, and that can be screened according to the methods of the invention. FIGS. 7A-7F depict the free-living flatworm planaria 701. FIG. 7B provides a schematic representation of a planaria 701. Planaria 701 has an anterior-posterior axis 703, a dorsal-ventral axis 707, and a left-right axis 705. Exemplary structures are also depicted including two eyes 702a and 702b, the central nervous system (CNS) 704, the intestine 706, and the pharynx 708. FIG. 7E provides a close-up view of the face of the planaria 701. In this view, the eyes 702a and 702b can be clearly seen. In certain embodiments, changes in one or more of these structures or in the orientation of one or more of these axes can be assessed. For example, changes in one or more of these structures or in the orientation of one or more of these axes can be assessed in response to compounds and/or to stimuli. Stated another way, when the methods of the present invention comprise assessing a change in behavioral, morphological, or anatomical characteristics, such changes may be assessed by evaluating a change in one or more of these structures or in one or more of these axes.

Like many model aquatic animal systems, cell biological and molecular tools are available to facilitate analysis of planaria. Such cell and molecular biological tools include, but are not limited to, reagents for detecting gene expression and changes in gene expression, reagents for detecting protein expression and changes in protein expression, and fluorescent dyes. FIGS. 7C and 7D depict planaria processed for in situ hybridization with RNA probes. FIG. 7C depicts a planaria 701 processed for in situ hybridization using a probe that recognizes a marker 710 of the intestine 706. FIG. 7D depicts a planaria 701 processed for in situ hybridization using a probe that recognizes a marker 712 of central nervous system tissue 704.

Planaria are only one example of aquatic animals suitable for use in the present invention. Planaria are small, inexpensive, and easy to rear in large numbers. Numerous cell and molecular biological reagents exist to facilitate analysis of planaria anatomy and morphology. Planaria are capable of classical conditioning and learning, thus making them a tractable model system for conducting experiments of learning and memory. Planaria regenerate, thus making them particularly well suited for experiments exploring regeneration. FIG. 7F illustrates regeneration of a planaria 701. As depicted, FIG. 7F illustrates regeneration of a trisected planaria 701.

The apparatuses and systems of the present invention can be used in any of a number of methods. Test animals, including both aquatic and non-aquatic animals, can be screened to identify and/or characterize compounds that alter behavioral, anatomical, or morphological characteristics. Test animals can be screened to identify and/or characterize compounds that alter (e.g., enhance or diminish) memory or learning. Test animals can be screened to identify and/or characterize compounds that alter the rate or extent of regeneration. Compounds can be screened in combination with each other or with known agents or stimuli to identify and/or characterize compounds that alter (e.g., augment or reverse) responsiveness to a known agent. Compounds can be screened in phenotypically or genotypically mutant animals to investigate gene expression, protein expression, or signal transduction. Mutant animals include naturally occur mutants, as well as mutants generated by chemical mutagenesis, radiation, and genetic manipulation.

Compounds can be screened in a high-throughput fashion, for example, by screening libraries of compounds either individually or in pools of compounds. Alternatively, a candidate compound or a small number of candidate compounds can be screened. In certain embodiments, compounds can be delivered to the test animals after they have been placed into a reaction well. For example, compounds can be added to the liquid media in which an aquatic test animal is maintained. In certain other embodiments, compounds can be delivered to the test animals prior to placement into a reaction well. For example, compounds can be directly fed or injected into a test organism. Whether compounds are administered prior to or after a test organism is placed into a reaction well, the subsequent effects of the compounds on the organisms can be observed using the methods and systems of the invention.

In addition to assays involving the screening of candidate compounds, the apparatuses and systems of the invention can be used to study the effects of other types of stimuli on behavior, learning, memory, anatomy, and morphology. Exemplary stimuli include, but are not limited to, changes in temperature or pressure, vibration, pH, light, electrical currents, magnetic fields, stress, and the like.

The apparatuses and systems can be further used in observing and analyzing information from mutant screens and other mutagenesis experiments. Briefly, mutagenesis is commonly used to generate a large number of mutant embryos or organisms. Zebrafish, *C. elegans, Drosophila*, and amphioxous are four species often used to conduct chemical or radiation-induced mutagenesis experiments. Currently, screens involve the generation of large numbers of potentially mutant embryos or organisms that must be individually examined by an investigator to identify phenotypically interesting embryos or organisms. Such embryos or organisms can then be further examined. The process is time consuming and laborious, as individual embryos or organisms are viewed by the unaided eye or using a microscope. Additionally, the process has large potential for error or investigator bias.

These and other limitations plague most screening assays conducted using currently available technology. In addition to the limitations described above, every screen is vulnerable to missing interesting phenotype because (i) it is impossible for an investigator to observe, with the unaided eye, every structural or behavioral characteristic and (ii) insights into characteristics worth noting may emerge during the screen, and thus may not be applied to all of the embryos or organisms being evaluated. The present invention overcomes these shortcomings.

These shortcomings impact other screening assays or experiments that rely upon detection and observation of potentially small behavioral, morphological, or anatomical changes. The present invention provides systems that integrate one or more cameras, as well as software and hardware that automates the collection of data and the identification of relevant changes. Furthermore, the present invention allows the data capture and storage. This facilitates sharing of data among investigators at the same or a distant research location, as well as allows data mining (e.g., where the same dataset is re-analyzed using the same or differing parameters to extract additional information). Furthermore, because the data can be captured and stored, the systems and methods of the invention help reduce the number of times that the same experiment must be conducted.

Any of the foregoing methods can be conducted using any of a number of aquatic animals of any of a number of developmental stages including embryonic, adult, tadpole, juvenile, larval, and fetal stages. The skilled investigator can readily select the appropriate aquatic animal and developmental stage based on cost considerations, size/space consideration, the particular process being examined, the expertise of the investigator, and the like. The apparatuses and systems, for example the reaction wells and trays, can readily be sized and shaped to accommodate aquatic animals of varying sizes. For example, a reaction well may be the approximate size and shape of a standard petri-dish (e.g., approximately 3-6 cm diameter). However, smaller reaction wells (e.g., approximately 1-3 cm diameter) and larger reaction wells (e.g., approximately 6-10 cm in diameter) may also be used.

Preferred aquatic animals, regardless of developmental stage, are relatively small such that the apparatuses and systems of the invention are amenable to table top use in a standard laboratory.

In certain embodiment, the apparatuses and systems can be used in any of a number of experimental methods and screening assays. Depending on the particular method, a skilled investigator can readily select the appropriate aquatic animal, the appropriate apparatus size and configuration, the appropriate camera(s) or photo elements, and the appropriate computer hardware and software.

Non-limiting examples of particular methods are described in detail below. In any of these or other screening or experimental methods, the invention contemplates that the aquatic animals may be observed directly using one or more camera or photo-elements. Alternatively, observation of the aquatic animals may be further aided using microscopy (e.g., a microscope fitted with a camera or photo-element). Furthermore, visualization of aquatic animals can, in certain embodiments, be augmented with one or more vital dyes, fluorescent dyes, or markers. In certain other embodiments, visualization of particular characteristics (e.g., gene expression, protein expression, cell proliferation, cell differentiation, pH, cell death, etc.) can be augmented by assaying treated and control aquatic animals using known cell or molecular biological techniques. Exemplary techniques can be selected for examining either live or dead animals, as the experiment warrants. Exemplary techniques for examining gene expression include, but are not limited to, in situ hybridization, Northern blot analysis, and RT-PCR. Exemplary techniques for examining protein expression include, but are not limited to, immunohistochemistry and Western blot analysis. When vital dyes, fluorescent markers or other aids to visualization are used, the invention contemplates that the photoelement may be specifically modified to capture the enhanced images. For example, when fluorescent markers are used, the photoelement may be a fluorescence-sensitive camera or a camera fitted with a fluorescence-sensitive filter.

The following are exemplary assays that can be conducted using the apparatuses and systems of the invention. One of skill in the art can readily adapt parameters, for example the size and shape of reaction wells or the fluid used for culture, to accommodate virtually any aquatic animal of virtually any developmental stage. Furthermore, one can readily adapt parameter to perform similar assays using other test organisms including non-aquatic test organisms.

Use in Learning Experiments

Classical learning experiments have been conducted in, for example, a traditional Skinner box. However, rigorously controlled learning experiments, large scale learning experiments, and screening assays using changes in learning or memory as a read-out have been difficult or impossible to do given the limitations of current methods and devices. The following exemplary learning assay using planaria, a tractable model system for studying learning and memory, demonstrates how the apparatuses and systems of the present invention address the limitations of the prior art. Note that this assay can be used to study learning in any test organism, including aquatic and non-aquatic animals of any developmental stage. The description below using planaria is merely exemplary of the learning and memory experiments that can be performed.

For experiments on the basis of learning in planaria, and for screens of drugs or genes which affect memory, the device may use the following basic paradigm. Although currently developed using flatworms, the following methodology can be applied to other aquatic animals. Worms are trained on an instrumental learning task within a reaction well. For example, one worm or worm fragment per reaction well is trained. The training algorithm consists of a reiterative loop performing the following steps (FIG. 3B). An image is obtained of a worm in its reaction well. The image is parsed (using fairly simple image analysis tools present in, for example, the Matlab software package), and the worm's position is estimated. Note that some worms will be sitting on the vertical walls of the dish, and thus not visible (they are very flat). The software will then decides (based on the details of the experiment as defined by the user before the start of the run) for each worm, as to whether the worm is rewarded (by, for example, lowering the level of a stimulating light—the worms do not like bright light), punished (via a brief electric shock to the fluid in which the worm is housed), or receives no action (a control condition).

The position of each worm along with the action taken is recorded as a time-stamped record in a database. The process continues until the experiment is terminated (minutes, hours, day, or weeks). In certain embodiments, the experiment provides electric shock kept at constant current. This is a potentially important control because it keeps the strength of the shock constant even if the resistance in the reaction well changes. In the case of a mucus secreting animal like planaria, changes in resistance in the reaction well may occur over time. Thus, it is important to have a mechanism to account for this and to supply a constant electrical current to the animal.

The foregoing provides a system for training flatworms in an environment that consistently rewards certain behaviors and punishes others. In a simple training exercise, a worm is rewarded, for example, for staying in the center of the dish and punished, for example, for crawling on the vertical edges (or vice versa—see controls below). However, this basic paradigm can be readily modified to include more complex behaviors or to examine different stimuli (e.g., vibration, temperature changes, pressure changes, etc.). Regardless of the particular paradigm, changes in worm behavior are recorded by a camera or photo-element, analyzed with image acquisition software, and stored. The data is maintained, for example, on an internet accessible database or a local server. Thus, without any interference with the experiment by the operator, each worm's learning curve is immediately ascertained by plotting the data (# of punishments, for example) as a function of time. The experimenter can decide when to stop the experiment (or to simply know how it is going) without having to interrupt it, or perturb the worms (e.g., thereby interfering with the training of the worms—the "home" learning condition).

At the end of the experiment, the database serves as a convenient record of the experimental data for further analysis, independent verification, or publication. Furthermore, because the data is recorded and stored without any experimenter bias, it can be maintained and re-analyzed at another time to examine the same or different parameters without having to re-conduct the experiment. In this way, the method provides a unique opportunity for data mining. Furthermore, the software and database can be made available on-line to facilitate remote access and/or distribution.

Examples 5-8 provided below show that this scheme was successfully used to conduct two distinct types of learning experiments in planaria. Furthermore, example 9 indicated that other experimental animals, including frog and fish embryos, are amenable for use in this system.

In any of the foregoing, the apparatus or system may include a thermocouple to regulate the temperature of the fluid in the reaction well during the experiment. Since temperature changes may alter the development, metabolism, or behavior of aquatic animals, this is important to help insure that mucus secretion, metabolic waste products, or the electrical current do not significantly alter the temperature of the fluid during the experiment.

In any of the foregoing, the apparatus or system may include a vibration mechanism or element for delivering a vibration stimulus to the test animal in the reaction well. For example, the system may include a piezo-electric element oriented adjacent to one or more reaction well. In certain embodiments, the system may include a piezo-electric element oriented adjacent to each reaction well.

In a consistent environment, worms quickly learn the desired behaviors. This device has a number of crucial advantages over older manual paradigms. First and foremost, it removes experimenter bias. Because the procedure is fully automated, no user involvement is needed during the experiment. This prevents confounding or false results due to experimenter error, bias, or fatigue. Using this system and methodology, no blind (or double-blind) protocols are required. In embodiments in which the data is maintained in an accessible database, interested independent observers can view the progress of the experiments or can analyze the data in the same or different ways.

The extensive data logging also allows other scientists to analyze all of the primary data, increasing the likelihood that others will discover novel trends via data-mining the original dataset; this is an important, cost-effective benefit as it allows maximal analysis to be extracted from each physical experiment performed. The automation also removes any issues of operator tedium, allowing large numbers of worms to be trained simultaneously. This, together with the extremely consistent timing of the feedback to the aquatic animals, is expected to result in data of high statistical power.

The following additional benefits are also realized. The paradigm does not suffer from the slime trail problem. The systems includes mechanisms to control temperature changes in the fluid during the experiment, and for regulating (e.g., keeping consistent) the magnitude of the electrical current administered to the animals. Furthermore, the fact that the animals are not handled during the experiment avoids all issues of sensitization to handling or other confounding stimuli (e.g., worms appear not to like new environments and act differently when they are moved from their "home" environment).

In certain embodiments, a single animal or animal fragment is maintained in each reaction well. In such embodiments, the isolation of, for example, individual worms avoids complexities of worm:worm interaction during training.

In certain embodiments, the reaction wells are shielded to limit or prevent exposure to extraneous stimuli such as temperature, chemical cues, vibration, or ambient light. Exemplary shields can be separate from or incorporated into the apparatus lid.

An additional benefit is that the system makes it easy to include and monitor appropriate controls. This is another substantial improvement over the prior art. For example, the automated nature by which reward and punishment stimuli are supplied to individual reaction wells makes it easy to simply shut off all outputs, or swap the reward/punishment conditions in half of the dishes.

As described for this method of conducting learning and memory experiments and screens, this paradigm is incentive-based. Thus, it produces very robust learning because the worms have the ability to avoid punishment by noticing the pattern in their environment. Moreover, it avoids the extinction problem of classical conditioning. Specifically, one of the limits of prior classical conditioning methods is that traditional methods of testing for the existence of learning after a specified training period, required the presentation of, for example, the light stimulus without the shock. However, each such test represents to the worm a counterexample to the very association one is hoping to achieve. Thus, in traditionally used approaches, the testing phase slowly counteracts whatever learning took place previously.

In contrast to the classical methods, in the present paradigm each instance of observation/response in the training environment reinforces the basic pattern the worms must learn. Moreover, data is gathered continuously and allows gauging of learning throughout the experiment. Thus, our protocol avoids extinction effects which can confound analysis.

Use in Behavioral Screens

In addition to revolutionizing the methods of inquiry into basic mechanisms of animal learning, the apparatuses and systems can be used to screen for compounds that alter behavior. In one embodiment of this paradigm, each reaction well containing an aquatic animal, or fragment thereof, receives a compound to be tested. Exemplary compounds include nucleic acids, peptides, and small molecules. In certain embodiments, the compound can be dissolved in water or other acceptable carrier and added to the fluid in which the aquatic animal is housed. Alternatively, the compound can be added to food and delivered to the aquatic animal via feeding. To further illustrate such an embodiment, bacteria expressing an RNAi construct can be used to infect liver pellets or other suitable food source. (Ji et al. (2002) Sheng Wu Gong Cheng Xue Bao 18: 117-120; Lee et al. (2003) Science 300: 644-647; Schmid et al. (2002) Trends in Neurosci 25: 71-74).

In other embodiments, the test organism (whether an aquatic or non-aquatic animal) can be administered compound prior to being placed into the reaction well. In this embodiment, the effect of the compound on the organism is analyzed after the organism in placed into the reaction well, but the organism is contacted with the compound beforehand.

The animal is imaged by computer as described above; image analysis algorithms are used to continuously track the animal and quantify estimates of movement speed, mean path traveled before turning, deviations from the usual flat glide (i.e., tendency to raise head or assume odd positions), etc. The software thus provides an estimate of the degree to which a test compound affects behavior, and the timeline with which this effect appeared. As described herein, images can be captured by a camera or photo-element, and image recognition software can be used to analyze the images. Compounds that cause a change in a behavioral characteristic in comparison to behavioral characteristics observed in the absence of the compound are identified. Such compounds can be further studied in the same or in different animals.

When used on control (untreated) animals in a constant environment, some potential screens include screens to identify or characterize compounds which alter animal activity (e.g., stimulants or depressants), decrease movement (paralytic agents), or alter normal behavior in other well-defined ways (e.g., reduce or increase sensitivity to environmental stimuli such as light or weak electric shock).

In one embodiment, when combined with the learning experiments described above, screens can be carried out for compounds which augment (or genes which participate in) learning rate, memory retention, intelligence (ability to abstract more complex patterns from their environments), etc. Identification of compounds that increase learning speed or retention ability would represent obvious basic and pharmaceutical progress.

Compound screens may also be combinatorial. In other words, screens involving combinatorial application of multiple compounds can be used to investigate the interaction of more than one substance. For example, an aquatic animal can be treated with a first substance known to have particular effects. Screens can then be conducted to identify or characterize compounds that augment, counteract, or otherwise interact with the first known substance. For example, an aquatic animal can be treated (e.g., cultured in or otherwise exposed) to a known stimulant such as caffeine or cocaine. A screen using such treated animals can identify compounds that counteract, augment, or otherwise affect the response of the animal to these stimulating substances. This approach may be useful for identifying genes or molecular pathways involved in an animal's response to such substances. We note that combinatorial screens may be used to in virtually any context. For example, combinatorial screens can be used in methods where the read-out is a change in one or more behavioral, morphological, or anatomical characteristic.

To further illustrate, an example of a combinatorial screen may include misexpressing a gene or protein in an animal and then using such an animal to screen for compounds that alter a behavioral, morphological, or anatomical characteristic of the animal. This approach may be useful in designing screens for drugs that may be used in the treatments of diseases or conditions that result from misexpression of a particular protein or misregulation of a particular gene or signaling pathway. Combinatorial screens may be used in virtually any context. For example, combinatorial screens can be used in methods where the read-out is a change in one or more behavioral, morphological, or anatomical characteristic.

Use in Morphological/Physiological Screens

In addition to behavioral and learning screens, analysis of animal morphology or anatomy can reveal endogenous processes and identify drugs (e.g., novel or known) which affect basic patterning mechanisms or processes. For illustrative purposes, we describe a particular screen using planaria. However, screens using other test organisms, including aquatic and non-aquatic test organisms, are similarly contemplated.

Planaria have amazing powers of regeneration which can be leveraged into screens designed to provide control to identify compounds that regulate regeneration and/or tissue growth or proliferation. Furthermore, planaria regeneration can be used in screens to identify genes, proteins, and signaling pathway implicated in regeneration.

The simplest screen involves computerized analysis of the growth and morphogenesis of small worms exposed (as they grow) to a compound. Each reaction well contains a planaria of a specific stage (e.g., to control initial pre-treatment size). For example, each well may contain a newly-hatched worm and one compound (e.g., an element of a small molecule or nucleic acid library dissolved in the liquid medium). At regular intervals, for example every 30 minutes for 1-2 weeks, a camera takes an image and a computer records the image of each worm in each dish. By way of example, the images are processed by first centering the image on the centroid of the worm's image and rotationally aligning along the major axes (to subtract out the fact that the worm will be in a different position in each snapshot), and then applying a simple morphometric analysis (Albertson and Kocher (2001) J Exp Zool 289: 385-403; Klingenberg et al. (1998) Biol Rev Camb Philos Soc. 73: 79-123; Klingenberg and Zaklan (2000) Evolution Int J Org Evolution 54: 1273-1285) based on pre-defined key "landmarks" (tip of tail, auricles, eyes, anterior tip of head). If the worm happens to be moving in a way which is not "flat" (head-raising behavior for example), the picture is retaken as soon as the animal regains a flat orientation (worms occasionally "corkscrew" and raise their heads, and this brief phenomenon can easily be detected by the software as a very sudden change in overall worm area). Significant deviations from allometric scaling, which represents the normal growth pattern of planaria (Oviedo et al. (2003) Dev Dyn 226: 326-333), are flagged by the computer, as would significant temporal deviations from control (untreated) planaria in some of the cells. Each affected worm's images are then assembled into a compressed multi-frame "movie" of its growth. This scheme is readily adaptable to any aquatic animal of any developmental stage.

At the end of the run, the user is informed of the compounds that affected growth. The user has access to various aspects of the data, for example, an MPEG timelapse movie containing side-by-side development of control worms and those in the identified reaction wells.

Using a similar scheme, other questions can be readily asked. For example, bisected or trisected worms can be contacted with compounds, and the ability of the compounds to alter the regeneration of the worm fragments can be assessed.

Worm life-span or activity level can be evaluated in whole worms or worm fragments. By monitoring activity levels (easily tracked as microns traveled per unit time) compounds that prolong lifespan and/or extend youthful vigor during life can be identified.

By way of further example, this paradigm can be used to identify compounds that alter endogenous genes/protein/signaling pathways participating in growth rate, differentiation, morphological control, regenerative ability, and polarity during regeneration. Such screens can be used to identify compounds that slow or accelerate growth, promote or inhibit head formation, cause runaway growth (tumor promoting agents which uncouple growth from pattern control), or alter the shape of the animal. It is also possible to screen for compounds which counteract the effects of known developmental toxins (when such a teratogen is supplied as a "background condition" or "first known substance or agent" to each reaction well).

Testing/Training

Screens or studies of certain behaviors, for example learning behaviors, require a training stage involving control conditions. By way of example using behavioral screens, training involves exposing the animal to specific stimulus/response parameters under which the animal demonstrates robust learning. There is literature on planaria reporting particular training parameters for planaria, and these can be a starting point for training planaria or other aquatic animals. The basic learning paradigm is defined by a number of orthogonal parameters (strength of punishment, waveform of electric shock, duration of stimulus, number of repetitions, delay between repetitions, latency between behavior and reward/punishment, total experiment length, etc).

Although the literature contains clues regarding planaria learning experiments, prior art methods have greatly hindered the ability to rigorously study the above parameters in various training/learning paradigms. Because manual experimentation is time-consuming, only small portions of the phase space defined by the independent parameters have been explored in the scientific literature. The automation (and scaleability) of the apparatuses and systems of the invention allow the rigorous testing of large numbers of combinations of learning conditions. This allows identification and use of parameters that result in the clearest demonstration of learning (highest % of correct responses which are retained for the longest possible time period).

The identification of these learning parameters will in itself be of value. Additionally, these learning parameters provide a background (e.g., a training phase) upon which screens for compounds which affect behavior can be conducted. The computerized control system makes it extremely easy to vary each parameter, to eventually understand what kind of protocol is most easily learned and retained by the worms. One can modify the behaviors which are rewarded/punished, alter the time-scale of each response (observe and punish the worms every second, or once every 10 minutes), use of rewards, punishments, or both (carrot vs. stick), strength of the light and/or electric shock, etc. Graded responses can also be tried (for example, strong shock for being on the sides, weak shock for being on the bottom but near the edge, reward for being close to the center).

In certain embodiments, the optimal length of training for a given aquatic animal, as well as the optimal length of the experiment is determined. Using prior art methods and devices, this was difficult and time consuming. However, this can be readily done using the automated systems of the invention because various parameters can be rapidly assessed. The ability to determine optimal training and experiment lengths is important because prior studies indicate that learning diminishes if the length of training exceeds an optimal level.

The foregoing provides certain exemplary methods that can be conducted using the apparatuses and systems of the invention. In certain embodiments of any of the methods of the invention described herein, behavioral screens can be conducted on animals who previously received a known substance. By way of example, animal behavior such as learning or memory can be altered by administering a known stimulant, depressant, or psychoanalytic drug, and compounds can be screened for their ability to augment or counteract the effect of the known agent.

In certain other embodiments of any of the methods of the invention, screens (e.g., behavioral, morphological, or anatomical) can be conducted on animals previously manipulated to alter gene expression, protein expression, or cell signaling. Such animals may appear mutant or otherwise altered, or such animals may appear wild type. Screens can then be conducted to identify compounds that interact with the particularly signaling pathway previously altered or to identify compounds that augment or decrease the effect of the initial manipulation on the particular behavioral, morphological, or anatomical characteristic.

As outlined throughout, any of the methods of the invention can be used to screen or assay in virtually any aquatic animal. Furthermore, any of the assays or screens (e.g., learning, behavioral, morphological, etc.) can be performed on whole organisms or on fragments of organisms. Exemplary fragments include a fragment of a bisected or trisected animal, or a fragment generated by fission. Further exemplary fragments include substantially whole organisms missing certain distinct structures. To illustrate, substantially whole organisms include organisms cut to remove a tail, an eye, an ear, one or two limbs (e.g., forelimb or hindlimb), a portion of heart, a portion of kidney, a portion of liver, and the like.

In addition to studies and screens of whole animals, animal fragments, and substantially whole animals, the invention contemplates studies and screens using animals with alternative morphologies. For example, animals with ectopic heads, ectopic eyes, ectopic limbs, left-right asymmetries, secondary axes, and the like. Any of these are specific examples of methods using phenotypically or genotypically mutant animals for study, screening, or further analysis.

(ii) Software and Hardware

Exemplary software and hardware components of the system are depicted throughout. Software described herein can run on a data processing system that can be a conventional data processing platform such as an IBM PC-compatible computer running the Windows operating systems, or a SUN workstation running a Unix operating system. Alternatively, the data processing system can comprise a dedicated processing system that includes an embedded programmable data processing system. For example, the data processing system can comprise a single board computer system that has been integrated into the system of the invention. The single board computer (SBC) system can be any suitable SBC, which include microprocessors, data memory and program memory, as well as expandable bus configurations and an on-board operating system.

Software can be written in any of a number of computer programming languages. The imagine acquisition and analysis algorithm can be realized as a software component operating on a conventional data processing system such as a PC or Unix workstation. In that embodiment, image acquisition and analysis can be implemented as a computer program written in any language including, but not limited to, Matlab, C, C++, Java, or Fortran. Additionally, the computer program can be written in microcode or written in a high-level language and compiled down to microcode that can be executed on the platform employed. The development of such systems is known to those of skill in the art. Other hardware architectures and their corresponding operating system infrastructures, including, but not limited to, parallel computer architectures, are noted as applicable platforms for the present invention.

An illustrative example of an algorithm for acquiring and analyzing changes in the behavior, anatomy, or morphology of an aquatic animal is provided herein. Images are acquired, for example, by one or more camera or photo-elements that collect images at specified intervals. One of skill can select the appropriate interval depending on the particular changes one expects to observe, the animal, and the duration of the experiment. For examples, images may be captured every 2, 4, 5, 6, 7, 8, 9, or 10 seconds. Alternatively, images may be captured less frequently, for example, every 30 seconds, or every 1, 5, 10, 15, or 30 minutes. In certain embodiments, images may be captured 1, 2, 4, or 6 times per day (e.g., approximately every 4, 6, 12, or 24 hours).

In addition to algorithms that modulate the frequency with which images are captured, the invention provides algorithms that modulate the delivery of stimuli (e.g., light, electrical current) to particular reaction wells, and stamp each collected image so that it can be readily correlated with the particular reaction well and experimental condition. (See, for example FIG. 3B).

Other image recognition methodologies are known and can be readily adapted and applied in the present system (Agatonovic-Kustrin and Beresford (2000) J Pharm Biomed Anal. 22(5):717-27; Buhmann et al. (1999) PNAS 96(25):14203-4; Patane and Russo (2001) Neural Netw. 14(9): 1219-37; Rodenacker and Bengtsson (2003) Anal Cell Pathol. 25(1):1-36; Wang et al. (2003) Inf Process Med Imaging. 18: 388-400; Zimmer et al. (2002) IEEE Trans Med Imaging. 21(10): 1212-21). Additionally, artificial neural net-based image recognition methods (ANN algorithms) may be useful and can be adapted (Agatonovic-Kustrin and Beresford (2000) J Pharm Biomed Anal. 22(5):717-27; Frenger (1997) Biomed Sci Instrum. 33: 344-9; Kwak et al. (2002) Environ Pollut. 120(3): 671-81; Yi et al. (1998) Medinfo. 9 Pt 2:1071-4). Depending on the particular aquatic animals, size and shape of the reaction vessels, stimuli used (or not used), length of the experiment, and observational output, algorithms for controlling experimental conditions and/or for capturing and analyzing changes in animal behavior, morphology, and anatomy can be readily adapted and employed.

The apparatuses and systems of the invention can be readily scaled up for high-throughput experiments and screening assays. Computer control of such a system may necessitate migration to a multi-CPU server, which may also work in a distributed, parallel, and/or networked fashion using many CPUs to divide processing load. An alternative design may utilize a central high-capacity supercomputer (such as the massively-parallel Connection Machine center which is funded by NSF in Pittsburgh) to handle several screens in different locations throughout the country. Such a system would allow comparison of experiments across remote location, as well as data mining of experiments conducted across remote locations.

Another aspect of the next generation of the apparatuses and systems of the invention will involve a robot for the delivery of individual aquatic animals into reaction wells and/or for the delivery of individual compounds or pools of compounds into reaction wells. Such automation is currently used in a variety of pharmaceutical and molecular biological contexts and can be readily modified and adapted for use with the disclosed systems.

In any of the foregoing, images can be captured using a single camera or photoelement that collects images from one reaction well or from multiple reaction wells. Alternatively, images can be captured using multiple cameras or photoelements, each of which collects images from a single reaction well or from multiple reaction wells. In either case, cameras or photo-elements of appropriate resolution can be selected based on the particular phenotypes or changes that one wishes to observes, as well as based on the number of reaction wells the camera will observes.

In certain embodiments, the images are obtained in grayscale (e.g., no color information is needed). However, in other embodiments, the images are obtained in color. Although the animals move, the reaction wells themselves are stationary during the experiment. Thus, the regions of interest (e.g., the area surveyed and captured by a camera) is static, thereby reducing the need for extensive image processing. Any image processing is minimal and can easily be performed in real time using <3 GHz CPUs in a standard PC.

In any of the foregoing, movies or still images summarizing the changes in animal behavioral, morphology, or anatomy over all or a portion of the experiment can be generated. Generated movies or still images can be saved, for example, as one or more MPEG, JPEG, or TIFF files.

(iii) Compounds

The present invention provides apparatuses, systems, and methods for conducting assays. In certain embodiments, conducting an assay includes screening compounds to identify and/or characterize a compound (e.g., a single compound or more than one compound) that modulates a behavioral, morphological, or anatomical characteristic of an aquatic animal. In certain other embodiments, conducting an assay includes screening compounds to identify and/or characterize a compound (e.g., a single compound or more than one compound) that modulates a behavioral, morphological, or anatomical characteristic of a test animal. Exemplary behavioral characteristics include, but are not limited to, memory and learning. Exemplary anatomical or morphological characteristics include regeneration. Additional anatomical or morphological characteristics include, but are not limited to, changes in pH in an animal, changes in gene or protein expression, changes in swimming behavior, changes in cell growth, changes in cell proliferation, changes in cell death, changes in differentiation, changes in development or morphology of a tissue or organ.

Compounds that have a particular effect on the animal can be further studied. For example, an identified compound can be studied in other model organisms including, but not limited to, *Drosophila*, zebrafish, frogs, chickens, mice, rats, pigs, cats, dogs, non-human primates, and humans. Alternatively, identified compounds can be studied in one or more cell-free or cell-based in vitro assays.

Any of a wide range of compounds can be readily screened using the apparatuses, systems, and/or methods of the invention. Exemplary classes of compounds include, but are not limited to, nucleic acids, peptides, polypeptides, small organic molecules, small inorganic molecules, peptidomimetics, antisense oligonucleotides, RNAi constructs, ribozymes, and antibodies. Compounds can be screened as single agents, multiple candidate agents, or libraries of agents. Exemplary classes of compounds are described in detail below.

Polypeptides and peptide fragments: In certain embodiments, the compounds are polypeptides or peptide fragments. Exemplary polypeptides or peptide fragments include wild-type, as well as variant sequences. Variant polypeptides include amino acid sequences at least 60%, 70%, 75%, 80%, 85%, 90%, 95%, 98% or 99% identical to a particular wild type polypeptide.

In addition to polypeptides and peptide fragments, the present invention also contemplates isolated nucleic acids comprising nucleotide sequences that encode said polypeptides and fragments. The term nucleic acid as used herein is intended to include fragments as equivalents, wherein such fragments have substantially the same function as the full length nucleic acid sequence from which it is derived. Equivalent nucleotide sequences will include sequences that differ by one or more nucleotide substitutions, additions or deletions, such as allelic variants; and will, therefore, include sequences that differ from the nucleotide sequence of, for example, the native nucleotide sequence. Equivalent sequences include those that vary from a known wildtype or variant sequence due to the degeneracy of the genetic code. Equivalent sequences may also include nucleotide sequences that hybridize under stringent conditions (i.e., equivalent to about 20-27° C. below the melting temperature ($T_m$) of the DNA duplex formed in about 1M salt) to the native nucleotide sequence. Further examples of stringent hybridization conditions include a wash step of 0.2×SSC at 65° C. Equivalent nucleotide sequences will be understood to encode polypeptides which retain the activity of the polypeptide encoded by the native nucleotide sequence.

Equivalent nucleotide sequences for use in the methods described herein also include sequences which are at least 60% identical to a given nucleotide sequence. In another embodiment, the nucleotide sequence is at least 70%, 75%, 80%, 85%, 90%, 95%, 98%, 99%, or 100% identical to the nucleotide sequence of a native sequence.

Nucleic acids having a sequence that differs from nucleotide sequences which encode a particular polypeptide due to degeneracy in the genetic code are also within the scope of the invention. Such nucleic acids encode functionally equivalent peptides but differ in sequence from wildtype sequences known in the art due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist. One skilled in the art will appreciate that these variations in one or more nucleotides (up to about 3-5% of the nucleotides) of the nucleic acids encoding polypeptides may exist among individuals of a given species due to natural allelic variation.

Antibodies: Exemplary compounds also include antibodies. Antibodies can have extraordinary affinity and specificity for particular epitopes. Without being bound by theory, antibodies can inhibit or potentiate the activity of proteins and signaling pathways in cells, thereby exerting or inducing a particular affect on cells, tissues, or organisms.

Monoclonal or polyclonal antibodies can be made using standard protocols (See, for example, Antibodies: A laboratory manual ed. by Harlow and Lane (Cold Spring Harbor Press: 1988)). A mammal, such as a mouse, a hamster or rabbit can be immunized with an immunogenic form of a peptide. Techniques for conferring immunogenicity on a protein or peptide include conjugation to carriers or other techniques well known in the art. An immunogenic portion of a protein can be administered in the presence of adjuvant. The progress of immunization can be monitored by detection of antibody titers in plasma or serum. Standard ELISA or other immunoassays can be used with the immunogen as antigen to assess the levels of antibodies. We note that antibodies may be immunospecific for a particular protein, may be immunospecific for a particular family of proteins, or may by less immunospecific and cross-react with multiple protein from related families of proteins. Antibodies which are immunospecific do not substantially cross-react with non-homologous protein.

By not substantially cross react is meant that the antibody has a binding affinity for a non-homologous proteins which is at least one order of magnitude, more preferably at least 2 orders of magnitude, and even more preferably at least 3 orders of magnitude less than the binding affinity of the antibody for the protein or proteins for which the antibody is immunospecific.

The term antibody as used herein is intended to include fragments thereof which are also specifically reactive with a polypeptide or family of polypeptides. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibodies of the present invention are further intended to include bispecific and chimeric molecules having affinity for a protein conferred by at least one CDR region of the antibody.

In one variation, antibodies of the invention can be single chain antibodies (scFv), comprising variable antigen binding domains linked by a polypeptide linker. Single chain antibodies are expressed as a single polypeptide chain and can be expressed in bacteria and as part of a phage display library. The nucleic acid encoding the single chain antibody can then be recovered from the phage and used to produce large quantities of the scFv. Construction and screening of scFv libraries is extensively described in various publications (U.S. Pat. Nos. 5,258,498; 5,482,858; 5,091,513; 4,946,778; 5,969,108; 5,871,907; 5,223,409; 5,225,539).

The technology for producing monoclonal antibodies is well known. The preferred antibody homologs contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including *E. coli*, or eukaryotes including yeast, *Saccharomyces*, insect cells, or mammalian cells, such as CHO, COS or BSC cells. One of ordinary skill in the art will appreciate that other host cells can be used to advantage.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, arninopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants.

To produce antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Fully human monoclonal antibody homologs are another compound that can be used. In their intact form these may be prepared using in vitro-primed human splenocytes, as described by Boerner et al., 1991, J. Immunol., 147, 86-95. Alternatively, they may be prepared by repertoire cloning as described by Persson et al., 1991, Proc. Nat. Acad. Sci. USA, 88: 2432-2436 or by Huang and Stollar, 1991, J. Immunol. Methods 141, 227-236. U.S. Pat. No. 5,798,230 describes preparation of human monoclonal antibodies from human B cells.

In yet another method for producing fully human antibodies, U.S. Pat. No. 5,789,650 describes transgenic non-human animals capable of producing heterologous antibodies and transgenic non-human animals having inactivated endogenous immunoglobulin genes.

Large nonimmunized human phage display libraries may also be used to isolate high affinity antibodies that can be developed as human therapeutics using standard phage technology (Vaughan et al, 1996).

Yet another preferred binding agent is a humanized recombinant antibody homolog. Following the early methods for the preparation of true "chimeric antibodies" (where the entire constant and entire variable regions are derived from different sources), a new approach was described in EP 0239400 (Winter et al.) whereby antibodies are altered by substitution (within a given variable region) of their complementarity determining regions (CDRs) for one species with those from another. The process for humanizing monoclonal antibodies via CDR "grafting" has been termed "reshaping". (Riechmann et al., 1988, Nature 332, 323-327; Verhoeyen et al., 1988, Science 239, 1534-1536).

Antisense, ribozyme and triplex techniques: Nucleic acid-based compounds include, but are not limited to, antisense oligonucleotides and ribozymes. Antisense oligonucleotides and ribozymes inhibit the expression of a protein, e.g., by inhibiting transcription and/or translation.

Binding of the oligonucleotide or ribozyme to the nucleic acid encoding the particular protein may be by conventional base pair complementarity, or, for example, in the case of binding to DNA duplexes, through specific interactions in the major groove of the double helix. In general, "antisense" therapy refers to the range of techniques generally employed in the art, and includes any therapy that relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a particular protein. Alternatively, the antisense construct is an oligonucleotide probe that is generated ex vivo and which, when introduced into the cell causes inhibition of expression by hybridizing with the mRNA and/or genomic sequences encoding a particular protein. Such oligonucleotide probes are preferably modified oligonucleotides that are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996;

5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668. With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to mRNA encoding a particular protein. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of mRNA, antisense nucleic acids should be at least six nucleotides in length, and are preferably less that about 100 and more preferably less than about 50, 25, 17 or 10 nucleotides in length.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-metllylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an anomeric oligonucleotide. An -anomeric oligonucleotide forms specific double-stranded hybrids with complementary RNA in which, contrary to the usual -units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451).

While antisense nucleotides complementary to the coding region of an mRNA sequence can be used, those complementary to the transcribed untranslated region and to the region comprising the initiating methionine are most preferred.

The antisense molecules can be delivered to cells or animals in vitro or in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically. We note that these and other methods are have been used to deliver single antisense oligonucleotides, as well as libraries of oligonucleotides.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts and thereby prevent translation. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

Ribozyme molecules designed to catalytically cleave an mRNA transcript can also be used to prevent translation of mRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered in vivo or in vitro. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes, unlike antisense molecules, are catalytic, a lower intracellular concentration is required for efficiency.

Alternatively, endogenous gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C. 1991, Anticancer Drug Des., 6(6):569-84; Helene, C., et al., 1992, Ann. N.Y. Acad. Sci., 660:27-36; and Maher, L. J., 1992, Bioassays 14(12):807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

RNAi: In other embodiments, the compound is an RNAi construct. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res,* 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) *Proc Natl Acad Sci USA*, 98:9742-9747; Elbashir, et al. (2001) *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev*, 2002, 16:948-58; McCaffrey et al., *Nature*, 2002, 418:38-9; McManus et al., *RNA*, 2002, 8:842-50; Yu et al., *Proc Natl Acad Sci USA*, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

Peptidomimetics: In other embodiments, the invention contemplates that the agent is a peptidomimetic. Peptidomimetics are compounds based on, or derived from, peptides and proteins. Peptidomimetics can be obtained by structural modification of the amino acid sequence of a known protein using unnatural amino acids, conformational restraints, isosteric replacement, and the like. The subject peptidomimetics constitute the continuum of structural space between peptides and non-peptide synthetic structures.

Exemplary peptidomimetics can have such attributes as being non-hydrolyzable (e.g., increased stability against proteases or other physiological conditions which degrade the corresponding peptide), having increased specificity and/or potency, and having increased cell permeability for intracellular localization. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in *Peptides. Chemistry and Biology*, G. R. Marshall ed., ESCOM Publisher: Leiden, Netherlands, 1988, p 123), C-7 mimics (Huffinan et al. in *Peptides. Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides. Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988)

In addition to a variety of sidechain replacements which can be carried out to generate the subject peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Additionally, peptidomimietics based on more substantial modifications of the backbone of a peptide can be used. Peptidomimetics which fall in this category include (i) retro-inverso analogs, and (ii) N-alkyl glycine analogs (so-called peptoids).

Furthermore, the methods of combinatorial chemistry are being brought to bear, e.g., PCT publication WO99/48897, on the development of new peptidomimetics. For example, one embodiment of a so-called "peptide morphing" strategy focuses on the random generation of a library of peptide analogs that comprise a wide range of peptide bond substitutes.

In an exemplary embodiment, the peptidomimetic can be derived as a retro-inverso analog of the peptide. Retro-inverso analogs can be made according to the methods known in the art, such as that described by the Sisto et al. U.S. Pat. No. 4,522,752. As a general guide, sites which are most susceptible to proteolysis are typically altered, with less susceptible amide linkages being optional for mimetic switching. The final product, or intermediates thereof, can be purified by HPLC.

In another illustrative embodiment, the peptidomimetic can be derived as a retro-enatio analog of a peptide. Retro-enantio analogs such as this can be synthesized using commercially available D-amino acids (or analogs thereof) and standard solid- or solution-phase peptide-synthesis techniques. For example, in a preferred solid-phase synthesis method, a suitably amino-protected (t-butyloxycarbonyl, Boc) residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid is introduced by coupling with diisopropylcarbodiimide. The resin is again washed, and the cycle repeated for each of the remaining amino acids in turn. When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

In still another illustrative embodiment, trans-olefin derivatives can be made for any of the subject polypeptides. A trans olefin analog can be synthesized according to the method of Y. K. Shue et al. (1987) *Tetrahedron Letters* 28:3225 and also according to other methods known in the art. It will be appreciated that variations in the cited procedure, or other procedures available, may be necessary according to the nature of the reagent used.

It is further possible to couple the pseudodipeptides synthesized by the above method to other pseudodipeptides, to make peptide analogs with several olefinic functionalities in place of amide functionalities.

Still another classes of peptidomimetic derivatives include phosphonate derivatives. The synthesis of such phosphonate derivatives can be adapted from known synthesis schemes. See, for example, Loots et al. in *Peptides. Chemistry and Biology*, (Escom Science Publishers, Leiden, 1988, p. 118); Petrillo et al. in *Peptides. Structure and Function* (Proceedings of the 9th American Peptide Symposium, Pierce Chemical Co. Rockland, Ill., 1985).

Many other peptidomimetic structures are known in the art and can be readily adapted for use in designing peptidomimetics. To illustrate, the peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345-1348). In still other embodiments, certain amino acid residues can be replaced with aryl and bi-aryl moieties, e.g., monocyclic or bicyclic aromatic or heteroaromatic nucleus, or a biaromatic, aromatic, heteroaromatic, or biheteroaromatic nucleus.

Small organic or inorganic molecules: In certain embodiments, the compound is a small organic or inorganic molecule. Small organic or inorganic molecules can agonize or antagonize the function of a particular protein. By small organic or inorganic molecule is meant a carbon contain molecule having a molecular weight less than 5000 amu, preferably less than 2500 amu, more preferably less than 1500 amu, and even more preferably less than 750, 500, or 250 amu.

Small organic or inorganic molecules can be readily identified by screening libraries of organic molecules and/or chemical compounds to identify those compounds that have a desired function. Alternatively, single compounds or small numbers of candidate compounds can be screened individual or in combination. In certain embodiments, the small molecule (e.g., an inorganic or organic molecule) is a non-peptidyl compound containing two or fewer, one or fewer, or no peptide and/or saccharide linkages.

The foregoing are illustrative examples of classes of compounds that can be screened to identify and/or characterize compounds that have a particular affect on an animal. One of skill in the art can select amongst available delivery methods to deliver the compound to the particular animal in the particular fluid. By way of example, many compounds readily transit epidermal barriers and other biological membranes. To administer such compounds to an aquatic animal, the compound can simply be added to the fluid in which the animal is cultured. Other compounds do not as readily transit epidermal barriers and biological membranes, and thus additional techniques have been adapted to administer such compounds to cells, tissues, and organisms. For example, RNAi constructs are often administered to animals by addition to their food or drinking water. Numerous types of nucleic acids are delivered via viral or plasmid-based expression vectors. Polypeptide-based compounds that do not readily transit membrane or that are not actively transported into cells via receptor-mediated mechanisms can be administered along with carriers that facilitate transit into cells and tissues. The foregoing exemplary administration methods are well known in the art and can be selected based on the compounds and aquatic animals being employed in the particular screening assays.

Compounds can be administered alone or as pharmaceutical formulations. Exemplary pharmaceutical compositions are formulated for administration to an animal. In certain embodiments, the compound included in the pharmaceutical preparation may be active itself, or may be a prodrug, e.g., capable of being converted to an active compound in a physiological setting. In certain embodiments the subject compounds may be simply dissolved or suspended water, for example, in sterile water. In certain embodiments, the pharmaceutical preparation is non-pyrogenic, i.e., does not elevate the body temperature of an animal.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a subject compound. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, in certain embodiments the agents may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The present invention provides apparatuses, systems, and methods for conducting assays. In certain embodiments, the assays are screening assays to identify and/or characterize one or more compounds that have a particular affect on an animal. Once identified compound can be further studied in other animals or in cell-based or cell-free assays in vitro. Such further studies can make use of the apparatuses, systems, and methods of the invention. However, further studies are not limited to those employing the technology of the present invention.

The present invention provides systems for screening assays to identify and/or characterize compounds, for example, compounds that affect behavioral, anatomical, or morphological characteristics of an animal. Identified compounds may be further characterized. Identified compounds may be useful for research directed to the further study of a particular behavioral, anatomical, or morphological process. Furthermore, identified compounds may be useful in the development of a pharmaceutical, or even as a pharmaceutical product. Accordingly, the present invention provides for compounds and pharmaceutical compounds identified and/or characterized by any of the methods of the invention.

In certain embodiments, the identified compounds may be useful in the development of a pharmaceutical product. Further testing of a possible pharmaceutical product may involve administration to animals and may additionally involve study of the preferable route of administration. Thus, another aspect of the present invention provides pharmaceutically acceptable compositions comprising an effective amount of one or more of the compounds described above, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) opthalamic administration, for example, for administration following injury or damage to the retina. However, in certain embodiments the subject compounds may be simply dissolved or suspended in sterile water. In certain embodiments, the pharmaceutical preparation is non-pyrogenic, i.e., does not elevate the body temperature of a human or animal patient.

(iv) Animals

The apparatuses, systems, and methods of the invention can be used to observe and conduct assays in any of a number of aquatic animals. The exemplary reaction wells and trays described herein are readily scaleable and the size and/or shape of the reaction wells and trays can be readily adapted to accommodate any of a number of aquatic animals of any of a number of developmental stages (e.g., embryonic, juvenile, tadpole, larval, adult, etc.). Similarly, the apparatuses, systems, and methods of the invention can be used to observe and conduct assays in any of a number of test organisms, including non-aquatic animals. The exemplary reaction wells and trays described herein are readily scaleable and the size and/or shape of the reaction wells and trays can be readily adapted to accommodate any of a number of test animals of any of a number of developmental stages (e.g., embryonic, juvenile, tadpole, larval, adult, etc.).

Exemplary test animals that can be observed and assayed using the apparatuses, systems, and methods of the invention include, but are not limited to, chordates, hemichordates, and protochordates. Further, exemplary test animals include invertebrates. For any of these animals, the invention contemplates the use of animals of any developmental stage. For example, the invention contemplates the use of embryonic organisms, larval stage organisms, tadpoles, fetal stage organisms, juveniles, and adults. One of skill in the art can select the proper animal and developmental stage depending on the particular assay being conducted, the particular compounds being assessed, and the particular developmental or behavioral process being investigated. Furthermore, one of skill in the art can select the appropriate animal and developmental stage based on the research interests of the investigator, time, and cost considerations, as well as the availability of other complementary research reagents. In certain embodiments of any of the foregoing, the aquatic animals used in a particular experiment may be, for example, genetically unrelated animals, sibling animals, or a clonal population of animals.

As used herein, the term "aquatic animal" is used to refer to any animal at any developmental stage that can be maintained for a period of time in fluid or a fluid containing environment. The term applies regardless of whether the animal lives in a fluid environment in nature. The term applies to both wildtype and mutant animals of any developmental stage.

As used herein, the term "non-aquatic animal" is used operationally to refer to any animal at any developmental stage that is not, during the course of the experiment, maintained in fluid or a fluid containing environment. The term applies regardless of whether the animal lives in a fluid or non-fluid environment in nature. The term applies to both wildtype and mutant animals of any developmental stage.

In one embodiment, the aquatic animal is a protochordate. Protochordates possess a hollow dorsal nerve cord, gill slits, and a notochord. Exemplary protochordates include tunicata (e.g., sea squirts, etc.) and cephalochordate (e.g., amphioxus). Exemplary amphioxus include, but are not limited to *Ciona intestinalis* and *Branchiostoma floridae* (Holland and Gibson-Brown (2003) BioEssays 25: 528-532; Gostling and Shimeld (2003) Evolution and Development 5: 136; Dehal et al. (2002) Science 298: 2157-2167; Nishiyama et al. (1972) Tohoku J Exp Med 107: 95-96; Ogasawara et al. (2002) Develop Genes Evol 212: 173-185; Pope and Rowley (2002) J Exp Biology 205: 1577-1583).

In one embodiment, the animal is an invertebrate. In one embodiment, the test animal is a non-aquatic invertebrate animal. Exemplary non-aquatic, invertebrate animals include *Drosophila*.

In another embodiment, the aquatic animal is a hemichordate. Exemplary hemichordates include acorn worms (Tagawa et al. (2001) Evol and Develop 3: 443).

In another embodiment, the aquatic animal is a nematode. There are over 10,000 known nematode species. These include parasitic nematodes (e.g., nematodes that are parasitic to humans, non-human animals, or plants). Exemplary parasitic nematodes include, but are not limited to, whipworms, Ascaris, hookworms, filarial worms, and root knot nematodes.

*C. elegans* is perhaps the most well known and thoroughly studied nematode, and the invention contemplates using *C. elegans* or other nematodes. Although *C. elegans* is considered a soil nematode, methods for culturing *C. elegans* in various quantities of liquid media (e.g., in a fluid) are well developed. See, http://elegans.swmed.edu/. Accordingly, the methods and apparatuses of the invention for conducting assays in aquatic animals can be readily used to conduct assays in *C. elegans*. Additionally or alternatively, *C. elegans* and other nematodes can be used experimentally in the absence of liquid (the animals are not maintained in liquid during the experiment). When used experimentally in the absence of liquid, these animals are exemplary of non-aquatic animals that can be used in the methods of the present invention.

In another embodiment, the aquatic animal is a chordate (e.g., a vertebrate). Exemplary aquatic animals include fish and frogs. Zebrafish (e.g., adult zebrafish and developing, e.g., embryonic, fish) are a particular example of a fish well suited for study. Zebrafish are an extensively used developmental system, and genetic, cell biological, and molecular biological reagents and methods are well known and available. Additionally, numerous chemical and radiation-based screens have produced large numbers of mutant zebrafish that can also be used for study.

*Xenopus laevis* and *Xenopus tropicalis* (e.g., adult, embryonic, tadpole, etc. stage animals) are particular examples of frogs well suited for study. Both species are used extensively, and well developed reagents exist. Additionally, *Xenopus tropicalis* is a genetically tractable model organism, and mutants have been and continue to be generated and characterized.

Figure 8:
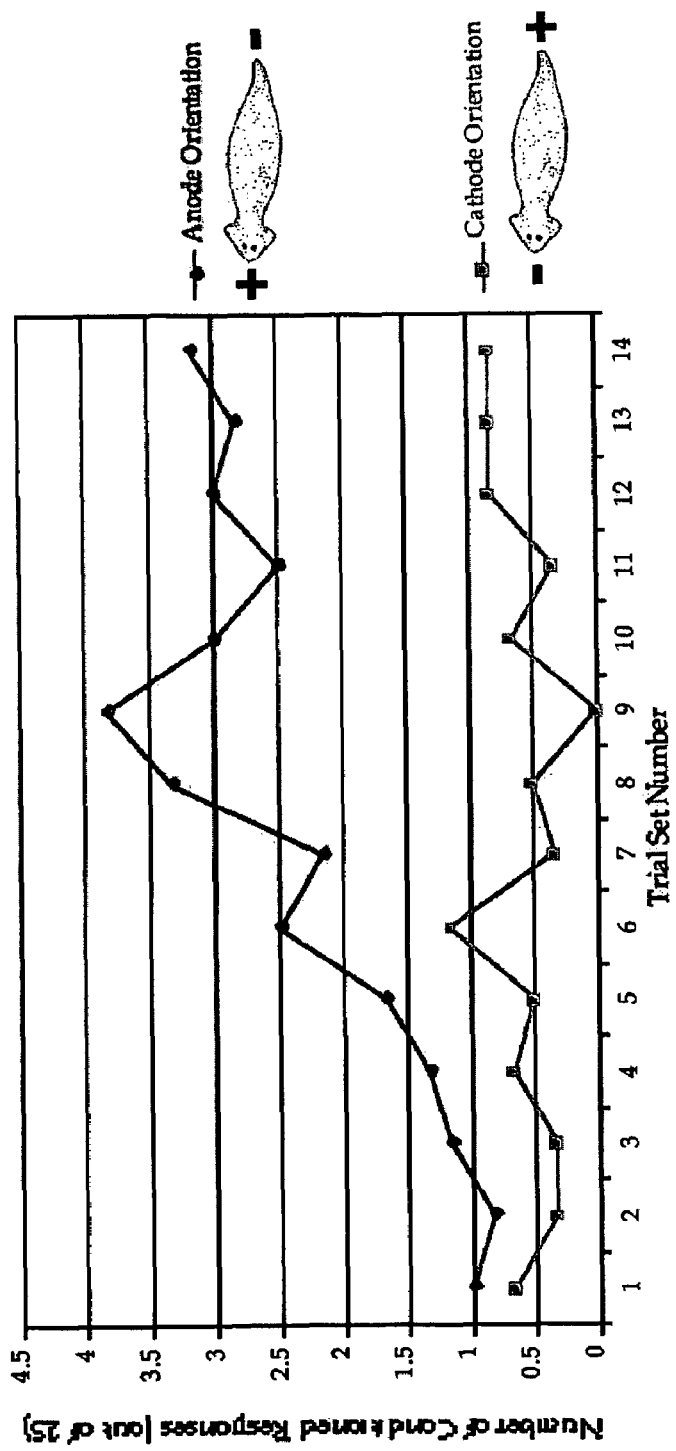
FIG. 8 shows sample learning curves for planaria specifically-oriented with respect to an electrical current.

In another embodiment, the aquatic animal is a flatworm. Exemplary flatworms are the free-living (e.g., non-parasitic)

flatworm planaria. Planaria are in the phylum *Platylhelmenthes* and the class Turbellaria. There are numerous species of planaria, any of which can be readily used. Planaria exhibit much of the complexity of vertebrate systems: a well-differentiated nervous system, intestine, eyes, brain, three tissue layers, and bilateral symmetry (FIG. 8). Planaria represent a critical breakthrough in the evolution of the animal body plan and are thought to very closely resemble the proto-bilaterian ancestor. It is the first organism to have both bilateral symmetry and encephalization, making it capable of detecting environmental stimuli quicker and more efficiently than the lower metazoans. Despite a simplistic appearance and evolutionary position, planaria possess a well-developed nervous system with true synaptic transmission and have what can be considered the first animal "brain" (Sarnat and Netsky (1985) Can J Neurol Sci. 12(4): 296-302). They have also developed sensory capabilities for the detection of light (Brown and Park (1975) Int J Chronobiol. 3(1):57-62; Brown et al., 1968), chemical gradients (Mason (1975) Anim Behav. May; 23(2): 460-9; Miyamoto and Shimozawa (1985) Zoological Science (Tokyo) 2: 389-396), vibration (Fulgheri and Messeri (1973) Boll Soc Ital Biol Sper. 49(20): 1141-5), electric fields (Brown and Ogden (1968) J Gen Physiol. 51(2)255-60), magnetic fields (Brown and Chow (1975) Physiological Zoology 48: 168-176; Brown (1966) Nature 209: 533-5), and weak y-radiation (Brown and Park (1964) Nature 202: 469-471). These reception mechanisms are integrated by the worm's nervous system into a rich and complex set of behaviors as they navigate their environment in the search for prey, mates, etc.

Planaria have been shown to exhibit learning and memory under classical conditioning paradigms as well as perform more complex tasks requiring a surprising degree of intelligence (such as operant or instrumental conditioning); they also possess many of the neurotransmitters, receptors, and behaviors associated with higher cognition (Block and McConnell, 1967; Creti et al., 1992; Eriksson and Panula, 1994; Jacobson, 1962; McConnell (1965a) A Manual of Psychological Experimentation on Planarians, pp. 111. The Worm Runner's Digest, Ann Arbor, Mich.; McConnell et al., 1960; Sheiman and Tiras, 1996; Smith, 1985; Villar and Schaeffer (1993) Biomed Environ Sci. 6(4): 327-47).

Like many of the other organisms described above, planaria are well suited for screening because of their small size. Furthermore, they are easy to raise and to subject to a multitude of reagents and manipulations. Their consistent, flat shape and active behaviors make it simple to observe the results of any behavioral or morphological perturbation. Moreover, evolutionarily, they are very similar to the ancestor of the bilateria clade, and have high relevance to human medicine and physiology both structurally and physiologically (Best and Morita (1982) Teratog Carcinog Mutagen. 2(3-4): 277-91; Sarnat and Netsky (1985) Can J Neurol Sci. 12(4): 296-302). Planaria offer an excellent combination of experimental tractability and sufficient complexity for asking a number of fascinating questions about basic functions of living systems (Eisenstein (1997) Behavioral Brain Research 82: 121-132). Crucially, as a model system, planaria are quickly acquiring a powerful set of molecular biological reagents and techniques, enabling genetic and cell-biological investigations into its structure and function (Agata et al., 2003; Alvarado et al., 2002; Cebria et al. (2002) Nature 419: 620-4).

Planaria are hermaphroditic and can reproduce sexually. Additionally, however, planaria can reproduce asexually by fission. This feature of planaria makes them an attractive choice for a model organism for screening assays because it is easy to readily and inexpensively produce a large population of genetically identical worms descended from a single individual (e.g., a clonal population of organisms for study).

As outlined above, planaria are a suitable organism for assays performed using the apparatuses, systems, and methods of the invention. Although the ability of planaria to learn makes them well suited for assays involving learning and/or memory (e.g., screens to identify and/or characterize compounds that alter learning and/or memory), they are equally well suited for morphological and/or anatomical assays (e.g., screens to identify and/or characterize compounds that alter morphology and/or anatomy). Additionally, planaria have exceptional regenerative capacity. A bisected flatworm readily regenerates. Thus planaria, either whole animals or fragments, serve as an excellent model system for assays to identify and/or characterize compounds that alter the rate or extent of regeneration.

The invention contemplates the use of any of the foregoing animals. Each of these has numerous characteristics that make them suitable for particular screening assays. The appropriate model organism can be readily selected based on the particular assays being conducted, as well as space and resource constraints. Furthermore, the appropriate developmental stage can be readily selected. Exemplary developmental stages include, but are not limited to, embryonic stages, tadpole stages, larval stages, juvenile stages, and adult stages. In certain embodiments, the animal is chosen due to its optical accessibility. Furthermore, the invention contemplates studying whole animals, as well as animal fragments. An exemplary animal fragment is a bisected or trisected organism. In one embodiment, the animal fragment is a bisected or trisected planarian. In another embodiment, the animal fragment is formed by fission of a whole animal. Additionally, the invention contemplates the use of wild type or mutant animals. In one embodiment, the animal is a wild type embryonic, tadpole, larval, fetal, juvenile, or adult stage animal. In another embodiment, the animal is a mutant embryonic, tadpole, larval, fetal, juvenile, or adult stage animal. Mutant animals include naturally occurring mutants, as well as mutants induced by chemical mutagenesis, irradiation, or modification via transgenesis or other exogenous genetic modification.

In certain embodiments, it may be desirable to conduct an assay, for example an assay to identify and/or characterize a compound that modulates a particular developmental process, in a relatively simple system. For example, initial screens to identify compounds involved in vertebrate cardiac development and morphogenesis can be conducted in a simpler system such as a protochordate or hemichordate. Such an approach may facilitate analysis of cardiac development without the complicating influence of genetic and functional redundancy often observed in vertebrate species. Identified compounds can later be analyzed in higher organisms including aquatic animals, as well as mice, rats, non-human primates, and humans. Such later analysis can be, where applicable, performed using the apparatuses and systems of the invention. Alternatively, such later analysis can be performed using other standard in vitro and in vivo assays.

As outlined above, the reaction wells and trays can be readily scaled to accommodate organisms of varying sizes and shapes. In certain embodiments, the invention contemplates that the animal may be of a size and shape not easily observable without the aid of a microscope or other magnifying device. By way of example, although Xenopus embryos are visible with the naked eye, distinct structures are more easily distinguished with the aid of a dissecting microscope. Accordingly, the invention contemplates the use of a microscope or magnifying element to increase the magnification of the image(s) captured by the camera. By way of example, the camera (or other photo-element) can be attached to the body of a dissecting microscope.

Exemplary animals that can be used in the apparatuses, methods, and systems of the invention are experimentally tractable model organisms. For example, cell biological, genetic, and/or molecular reagents exist for these model organisms. To illustrate, the availability of fluorescent reagents to label living or non-living animals and cells may facilitate further study and analysis, or may help improve the quality of images. For example, zebrafish or planaria carrying fluorescent protein-linked constructs which highlight a particular group of cells, organs, or neuronal paths (Haycraft et al. (2001) Development 128(9): 1493-505; Offield et al. (2000) Development 127(9): 1789-97) will make it easy for the software to identify mutants or compounds which alter the normal/wild type pattern. Finally, physiological screens can be carried out by devices that measure the fluorescence of vital or reporter dyes, such as pH- and voltage-sensitive dyes (Buckler and Vaughan-Jones, 1990; Epps et al., 1994; Seksek et al., 1991; van Erp et al., 1991) which can give specific information on in vivo processes in real time. For example, screens are easily envisioned for drugs which change the pH of key tissues, or mutants resistant to the membrane-depolarizing effects of common toxins (Naitoh et al., 2001; Yamashita et al., 2000). If desired, the individual cells can also be fitted with sensors for specific chemicals (dissolved oxygen, waste products, pH sensors, toxins, etc.) to monitor or screen for any desired physiological reaction.

Additional cell and molecular tools including reagents for RNA analysis (e.g., Northern blot hybridization, RT-PCR, RNase protection, in situ hybridization, GeneChip analysis) and/or protein analysis (e.g., immunohistochemistry, Western blot analysis) may be useful. Such reagents may be useful during the screening stage to help identify compounds that have a particular effect on an animal. For example, such reagents could be used to help identify compounds that increase/decrease the expression of a particular gene or protein in a particular cell type. Alternatively, such reagents can be used to further analyze the effects of identified compounds on the same or different animal species.

The apparatuses, systems, and methods of the invention involve culturing or otherwise housing an animal in a reaction well. In certain embodiments, the animal is maintained in the reaction well in the presence of fluid. When the animal is maintained during the experiment in fluid, the animal is referred to throughout the application as an aquatic animal. As used herein, an aquatic animal is any animal capable of living in a fluid environment. The term encompasses animals that naturally exist in a fluid environment for all or a portion of their lifecycle, as well as animals that can be maintained in a fluid in a laboratory setting but do not naturally exist in a fluid environment.

The particular fluid can be readily chosen based on the particular animal. Exemplary fluids are fluids suitable for maintaining the animal throughout the experiment. In one embodiment, the fluid is substantially inert. In other words, prior to the addition of a compound, the fluid is substantially free of additives that alter the behavior, anatomy, or morphology of the animal. Exemplary fluids include spring water, culture media, salt water, deionized water, and the like.

In certain embodiments, fluid can be introduced, removed, changed, or supplemented by removing the lid of an apparatus, thereby uncovering the reaction well. In certain other embodiments, fluid can be introduced or supplemented via an inlet that extends into the reaction well. In certain other embodiments, fluid can be removed or changed via an outlet that extends from the reaction well. In certain other embodiments, fluid can be added to the reaction well via the inlet and removed via the outlet. Adding and removing fluid during the course of an experiment may be useful, for example, to replace fluid that evaporates during the experiment or to remove (and then replenish) metabolic and other waste products that may accumulate over the course of the experiment.

The fluid may optionally be supplemented with food or other nutrients. However, depending on the animal and the duration of the experiment, feeding may not be necessary. For example, planaria can survive without feeding for several weeks. Accordingly and in other embodiments, the fluid is substantially free of food or similar nutrients. When food or other nutrients are supplied to the animal, the food or other nutrients may be supplied by removing the lid and adding the food directly to the reaction well. Alternatively, the food or other nutrients can be added via the inlet.

In certain other embodiments, the fluid may be supplemented with anti-bacterial, anti-viral, or anti-fungal agents designed to promote the health of the organism throughout the experiment. Alternatively or additionally, the fluid may be supplemented with agents designed to prevent degradation of test compounds. By way of example, such agents include protease inhibitors, RNase inhibitors, or DNase inhibitors.

In other embodiments, the test animal is not maintained in fluid. In such embodiments, the test animal may be maintained within the reaction well on a non-liquid surface. Exemplary surfaces include agar, wax, plastic, mesh, soil, grass, or other non-liquid surfaces appropriate for the particular test organism. As detailed above for aquatic animals, non-aquatic animals can optionally be fed and/or administered supplements.

EXEMPLIFICATION

The invention now being generally described, it will be more readily understood by reference to the following examples, which are included merely for purposes of illustration of certain aspects and embodiments of the present invention and are not intended to be limiting in any way.

Example 1

Planaria Memory in a Simple Reaction Well

We established a clonal (genetically-identical) flatworm colony which presently consists of over 7000 worms grown by asexual reproduction from a single individual. We designed and built a simple manual electrical apparatus for delivering an overhead light (conditional stimulus) followed by weak electric shock (to be used as a training stimulus), and a prototype learning station which allows easy delivery of the conditional and unconditional stimuli and observation of the flatworms' response under precisely-controlled time and light conditions. In particular, special attention was paid to ensuring that external variables known to affect behavior (such as vibration, changes in temperature and light, etc.) would be minimized. FIG. 1, which is described in detail above, depicts the simple apparatus. Note that in FIG. 1, the surrounding shielding used to exclude external stimuli is not shown.

We compared the effect of pre-slimed versus clean reaction wells on worm behavior. We also conducted a test of the naive response rate to light to ensure that light could be used as an appropriate conditional stimulus. We also tested the electrical current used as the unconditional stimulus. Specifically, we examined the use of direct current versus sinusoidal alternating current, and the effect of worm orientation toward anode versus cathode on behavioral response. Additionally, throughout all experiments and observations, we assessed the overall health of subject worms.

Worms were isolated and starved for the duration of the study. Starving the worm (e.g., not feeding them throughout the experiment) inhibits spontaneous fissioning. Additionally, it reduces maintenance by eliminating both the need to feed the worms and by reducing the accumulation of waste products in the fluid. Experimental subjects were placed in a small spring-water filled reaction well containing platinum-iridium surgical grade electrodes on either end of the reaction well. The electrodes were attached to either a DC (constant) or a sinusoidally oscillating electrical current (AC current ensures the avoidance of electrode bias or the introduction of a pH gradient into the medium). After pre-sliming the trough, test worms were given a brief acclimation period, followed by a series of training trials.

Worms were trained using the temporal contingency principle (Agranoff, 1999; Carew, 1986). Worms were exposed to the conditional stillulus (CS—in this case an 11 W fluorescent light source centered over the reaction well). The CS was immediately followed by the unconditional stimulus (US—in this case an electrical shock). The light was turned on for 2 s, followed by a 1 s shock. The presence or absence of a longitudinal bodily contraction, a behavioral response normally associated only with the US, was recorded for the 2 s in which the CS is used, but before the US. Between trials, worms were given a 30 s resting period. Based on previous data correlating number of training trials to optimal performance, we have chosen to limit the training to 1 block of 25 trials once per day (McConnell, 1964; Roe, 1963). The criterion of learning was set to 10 sequential successful training trials. A separate test for acquisition was not performed to avoid the possibility of premature extinction due to exposure to CS without shock. Worms that did not reach criterion after 250 trials were excluded from further experimentation.

We observed several important facts during our pilot study. Firstly, the worms do appear to learn under this paradigm—we observed a statistically significant gain in correct responses over the first set of trials. Secondly, we discovered (by analysis of individual data obtained from worms oriented randomly with respect to the polarity of the shock), that the worms learn better when oriented in a particular direction with respect to the electrical polarity of the shock. In the second set of trials, we oriented each shock with respect to the direction the worm happened to be facing at the time (by flipping the polarity on the shock device). The worms show better performance when the positive pole of the electric signal is located near their anterior end (FIG. 8). This finding led us to re-design the electric shock apparatus to include a double-pole/double-throw (DPDT) switch for easy reversal of polarity every time the worm turns around in a reaction vessel, allowing the user to maintain the same maximally-effective orientation throughout all trials irrespective of the worm's movements. Thus, in certain embodiments where apparatuses and/or systems of the invention include a electrical elements for providing an electrical current to an animal, such electrical elements may include a double-pole/double-throw switch for modulating the polarity of the current.

Example 2

Memory Experiments Using Planaria Fragments

During the latter stages of the experiments outlined in Example 1, a number of the worms spontaneously fissioned. This provided an opportunity to examine learning in worm fragments. We note that, although not examined in this experiment, fissioned fragments would also provide an opportunity to examine regeneration or proliferation.

We observed that both head fragments and tail fragments exhibited significant performance in the testing phase (average % performance for head-derived worms=40%; average % performance for tail-derived worms=24%, n=5, p<0.01 for the tail-derived performance relative to untrained worms). This confirms that memory and learning can be studied in both intact organisms and in fragments of organisms. We note that although this experiment was performed on fragments generated by fission; fragments may be generated by exogenously cutting the animals.

Example 3

Automated Planaria Memory Experiments

Figure 9:
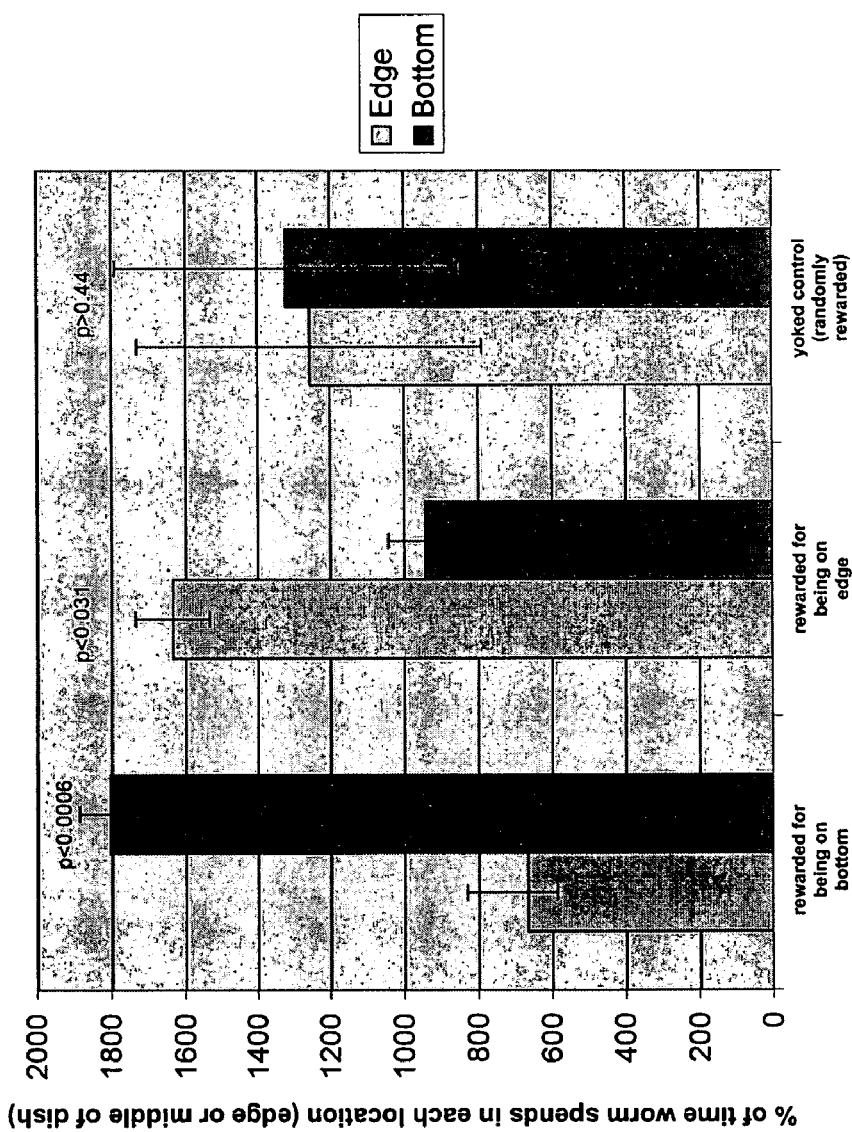
FIG. 9 summarizes the results of a planaria learning experiment.

A representative dataset from one instrumental learning test is shown in FIG. 9. The data was generated using planaria housed and analyzed using the system of the invention shown in FIG. 10. The system used in these experiments has 12 reaction wells running in parallel. The software tracked each worm and delivered rewards (e.g., reduction in light stimulus) and punishments (electrical current) based on the programmed training paradigm. Data was collected in real-time on each worm's performance. Using features described throughout we overcame a number of technical problems. For example, the USB camera and filter were selected to allow image capture without providing a bright light which may act as an additional stimulus to the animal.

One group of worms was rewarded for staying in the center of their reaction wells; another group was rewarded for being on the edge of their reaction wells; and the third group was rewarded/punished randomly, regardless of where in the reaction well they were. The light CS and electrical current US were controlled and administered in an automated fashion.

The data shown in FIG. 9 demonstrate that in less than 48 hours, each experimental group significantly learned to stay in the appropriate location, while the controls learned nothing. This demonstrated that our paradigm can train animals to high efficiency in an instrumental learning task in an automated fashion without experimenter interference. One substantial advantage to this automated methodology is that it allows data to be obtained and made publicly-available in real time. Furthermore, it avoids the limitations and biases inherent in tedious behavioral experiments which must be assayed by hand by the experimenter.

Figure 11:
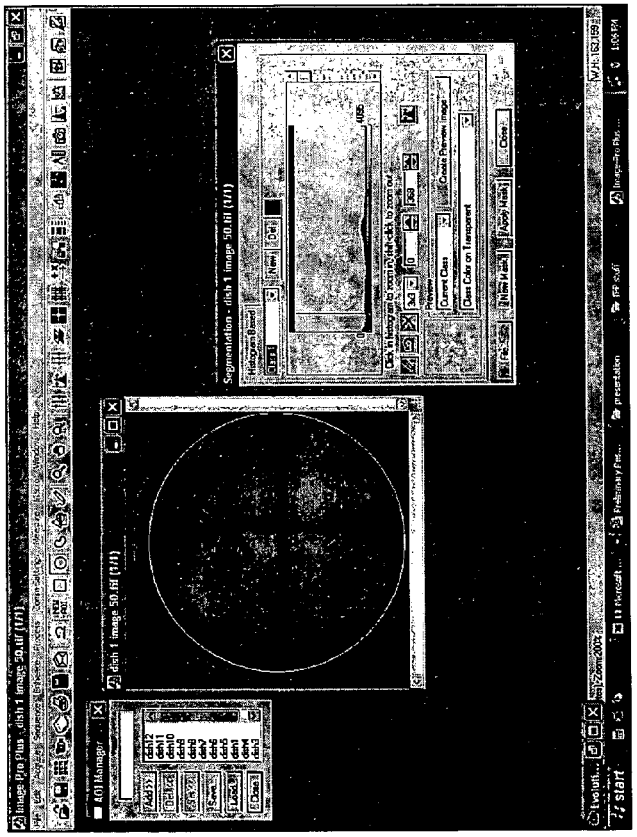
FIGS. 11A and 11B show sample screen shots tracking changes in planaria movement during the course of an experiment.
Figure 11:
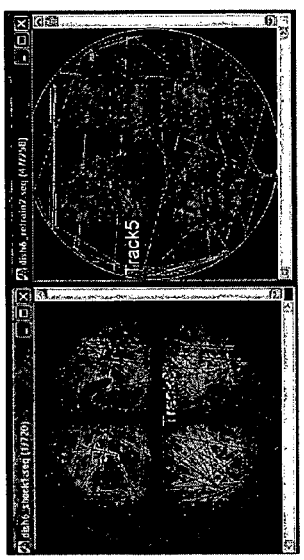

FIGS. 11A and 11B are screen shots provided to show how simple image analysis software can be used to track, record, and quantitate changes in one or more behavioral, morphological, or anatomical characteristics.

Example 4

Clonal Expansion of Good Learners and Poor Learners

These automated learning experiments can be used to identify "good" learners and "poor" learners in a population of animals. In the case of aquatic animals that produce asexually, good learners or poor learners can be selected and readily expanded to create a separate colony. Colonies of good performers or poor performers can be used in drug screening, or can be analyzed using microarray approaches. Microarray approaches can be used to help identify genes or proteins that are differentially expressed in good learners vs. poor learners.

Example 5

Learning for Spatial Orientation

The following methods were used for Examples 5-8. The species of planaria used in these studies was *Dugesia tigrinia*, obtained from Ward's Natural Science. The planaria colonies were stored in natural spring water at 22.5° C., and kept on a 9 hour light/15 hour dark cycle. The colonies were fed once per week with organic beef liver. Their water was changed several hours after feeding and 3 days following each feeding. Worms were not fed (e.g., they were starved) the week they were used in an experiment because starved worms were less likely to fission during the experiment.

Figure 10:
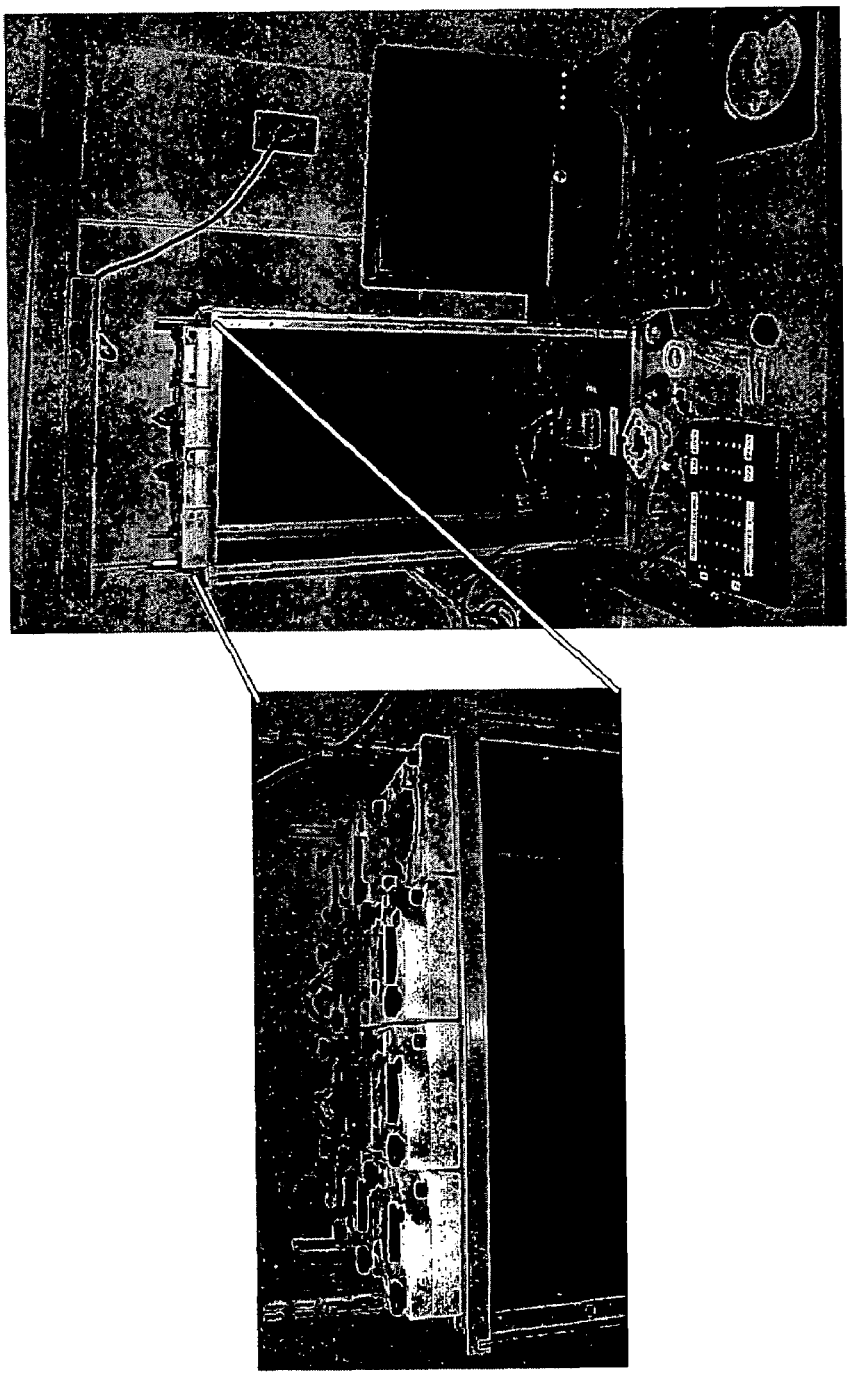
FIG. 10 depicts a system, according to another embodiment of the invention.

For the duration of an experiment, individual worms were placed in a reaction well and a plurality of reaction wells were arrayed, as shown in FIG. 10. The worms were not fed during the experiment. Each reaction well included electrodes made of a 90%/10% platinum/iridium alloy for delivering current.

The camera used in these experiments was a PixeLink PI-A661 (monochrome, 1.3 megapixel resolution), with a Kowa HR F1.4/12 mm flatfield lens. The PC controlling the prototype device was a Dell Dimension 4600 with Windows 2000 Pro and a FireWire PCI card. The software controlling the device was written and run within Matlab v7.1 with image acquisition toolbox.

The red LEDs ranged from 1-3.75 V. The white LEDs ranged from 0.5-3.75 V. The electrical stimuli ranged from 0-10.5 mA. Stimulation of the planaria within the reaction well and observation of the experimental animals was automated.

We demonstrated that worms can be trained to learn spatial orientation. As indicated above, the experiments were conducted and the worms were observed using the system and apparatus detailed in FIG. 10. Worms were trained to stay on the bottom of the reaction well. In a pre-screening stage, worms have a strong preference to remain on the vertical side of the reaction well (approximately 97% of the time). Following training, trained worms oriented to the bottom of the dish (e.g., made a correct choice) a statistically significant percentage of the time.

Briefly, in the training trial, the trained group of planarians was trained to move to the bottom of the reaction well using a combination of a shock (an electrical stimulus) and a light stimulus. The yoked controls received the same stimuli. However, for the yoked control animals, there was no causal relationship between the worm's responsiveness to the stimuli and the punishments they received. In other words, for yoked control worms, there is no specific behavior to associate with the reception or avoidance of punishment, and thus no training. Training was for 24 hours. Feedback stimuli (DC shock and a flash of white LED light) were applied for 1 second as punishment when the worm made the incorrect choice to remain on the edge (the vertical face) of the reaction well.

Figure 12:
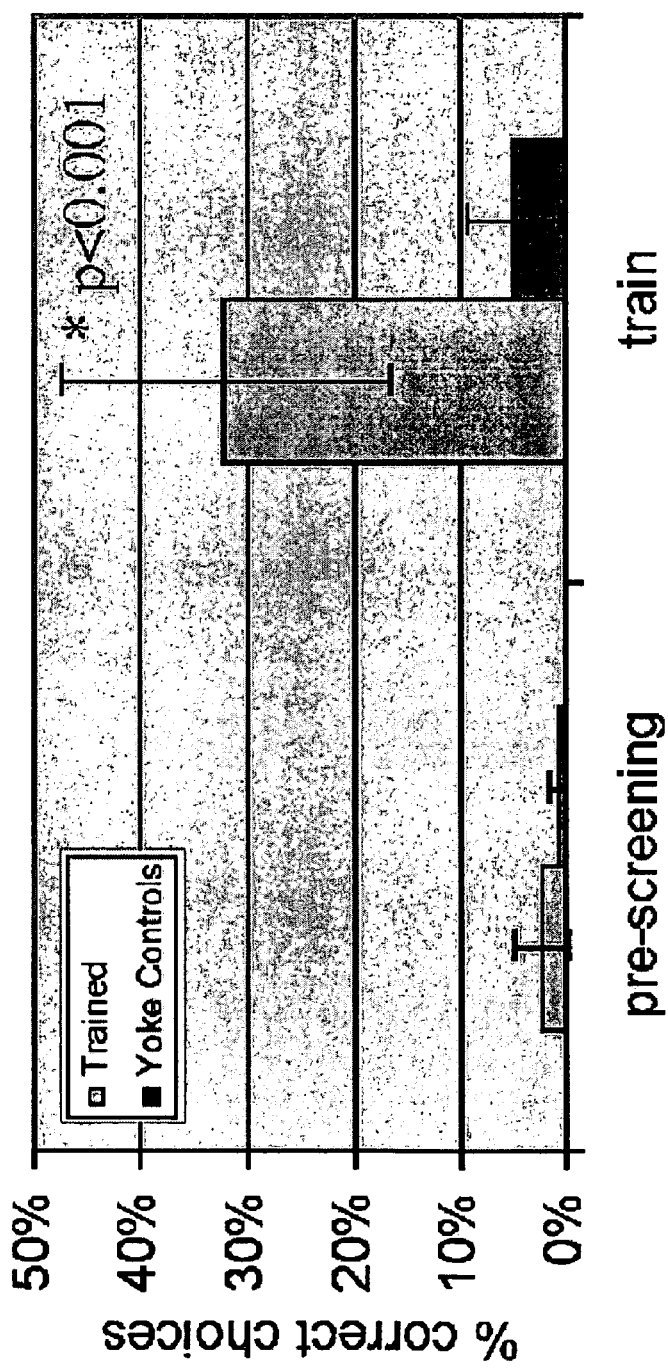
FIG. 12 summarizes results indicating that planaria can learn their spatial orientation and can be trained to orient to the bottom of a reaction well.

The results of these experiments are summarized in FIG. 12. After 24 hours of training, the worms were significantly more likely (p<0.001) to go to the bottom of the reaction well. These results indicated that the worms can sense their orientation (e.g., along the bottom versus the vertical edge of the reaction well), and that the worms can be trained to associate punishment (e.g., shock and bright light) with orientation in the reaction well.

Example 6

Learning for Light

We demonstrated that worms can be trained to learn preference for light. As indicated above, the experiments were conducted and the worms were observed using the system and apparatus detailed in FIG. 10. Worms were trained to move from a dark to a lit quadrant of the reaction well (e.g., to not be photo-avoidant). In a pre-screening stage, worms were observed in the absence of any stimulus to identify worms with a strong innate light preference. Only worms with an innate light preference of less than 25% were used in the remainder of this experiment.

Worms that met the experimental inclusion criteria (those with an innate light preference of less than 25%) were trained in either the training or yoked control group. The training entailed encouraging the worms to preferentially move into two quadrants of their reaction wells that were lit with white LEDs (lit quadrants). The training group of worms was trained to move to the lit quadrants using a combination of shock and light stimuli. The yoked control group received similar stimuli, but without the appropriate correlation between the correct behavior and the punishment.

Training consisted of three two-hour trials spread over three days. The feedback stimulus was applied once every 30 seconds for 1 second. The worms received the DC shock as a punishment for making the incorrect choice to stay in the dark or received a "reward" of a reprieve from all light to reinforce the correct choice of moving into the lit quadrants.

Figure 13:
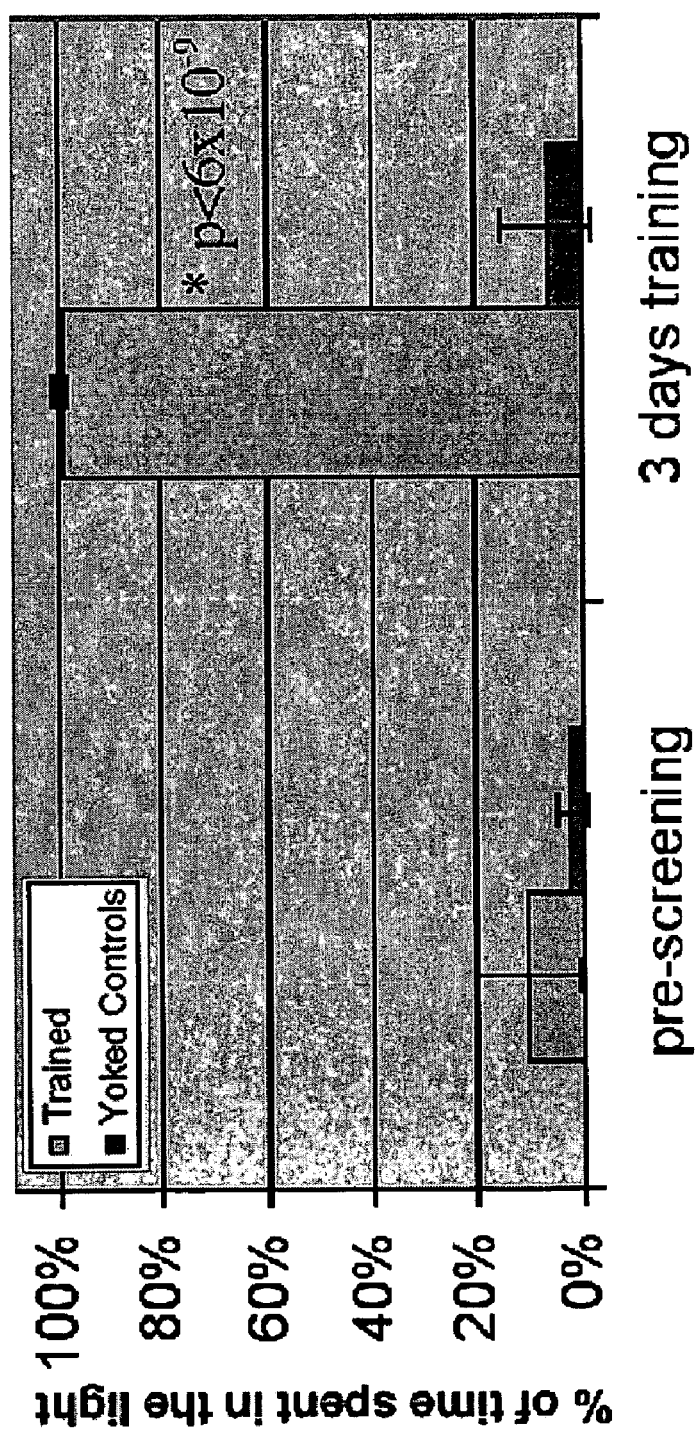
FIG. 13 summarizes results indicating that planaria can be trained to travel into the lit regions of the reaction well.

The results of these experiments are summarized in FIG. 13. After 3 days of training (3, two hour trials spread over 3 days), the worms were significantly more likely ($p<6\times10^{-9}$) to travel into the lit quadrants of their reaction wells. These results indicated that the worms can be trained to orient themselves based on light.

We note that this training paradigm based on light can also be evaluated in terms of latency. Latency is the a measure of how long it takes before a trained worm will move to and remain in lit quadrant for five minutes. The measure of latency used in these experiments was the number of images captured by the photoelement.

As outlined above, in these experiments, the training was performed with planaria that had already been preselected based on having an innate light preference of less than 25%. The worms were trained to move to two lit quadrants of the reaction well using as stimuli DC shock (as a punishment) and a reprieve from all light as a reward. Latency is measured as the number of images that it takes before a worm remains in the "correct" (lit) quadrant for at least 5 consecutive minutes. The minimum possible latency is 10 images and the maximum possible latency is 240 images (the number of images taken during the training trial). Once the planaria achieved this (remained in the light for 5 minutes), they were given a 5 minute rest period in darkness.

Figure 14:
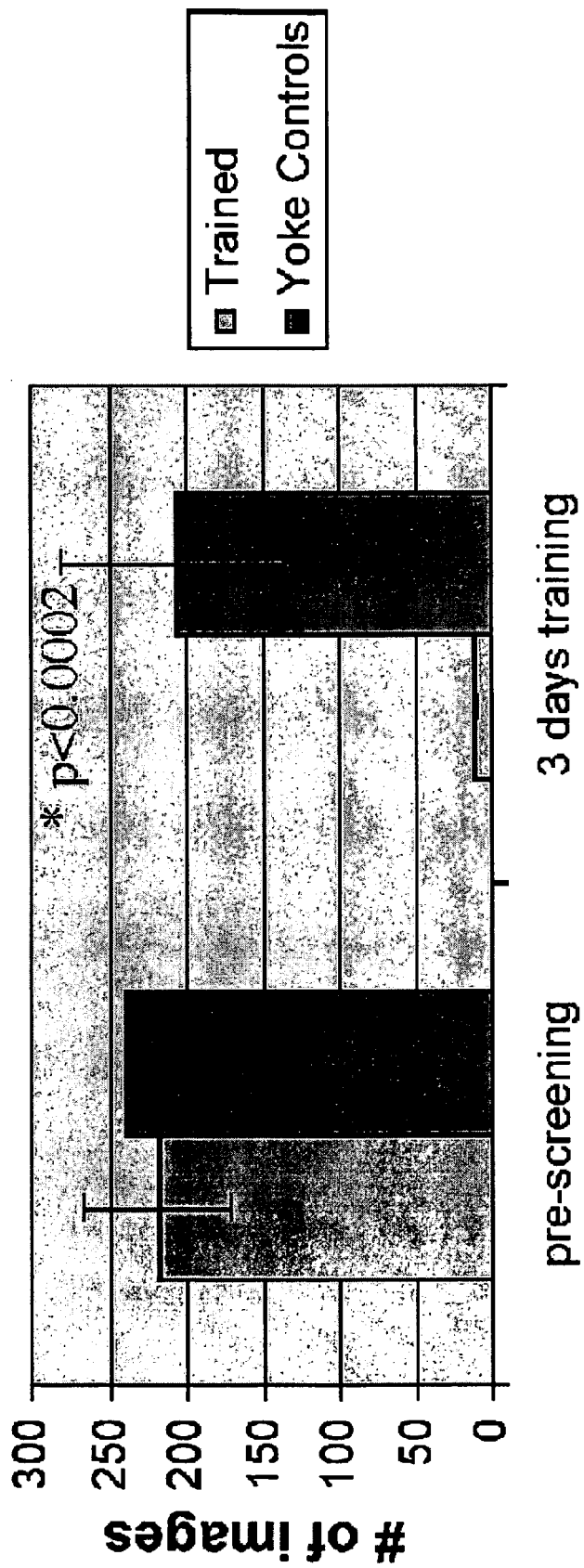
FIG. 14 summarizes results measuring latency in the light training paradigm.

During pre-screening, the trained and yoke control groups all had average latencies of greater than 210 images. After training, the trained group showed a significantly (p<0.0002) lower latency than the yoked control group. This result is summarized in FIG. 14. Measurements of latency can be used to assess the speed at which an experimental animal learns.

Example 7

Memory Retention

Figure 15:
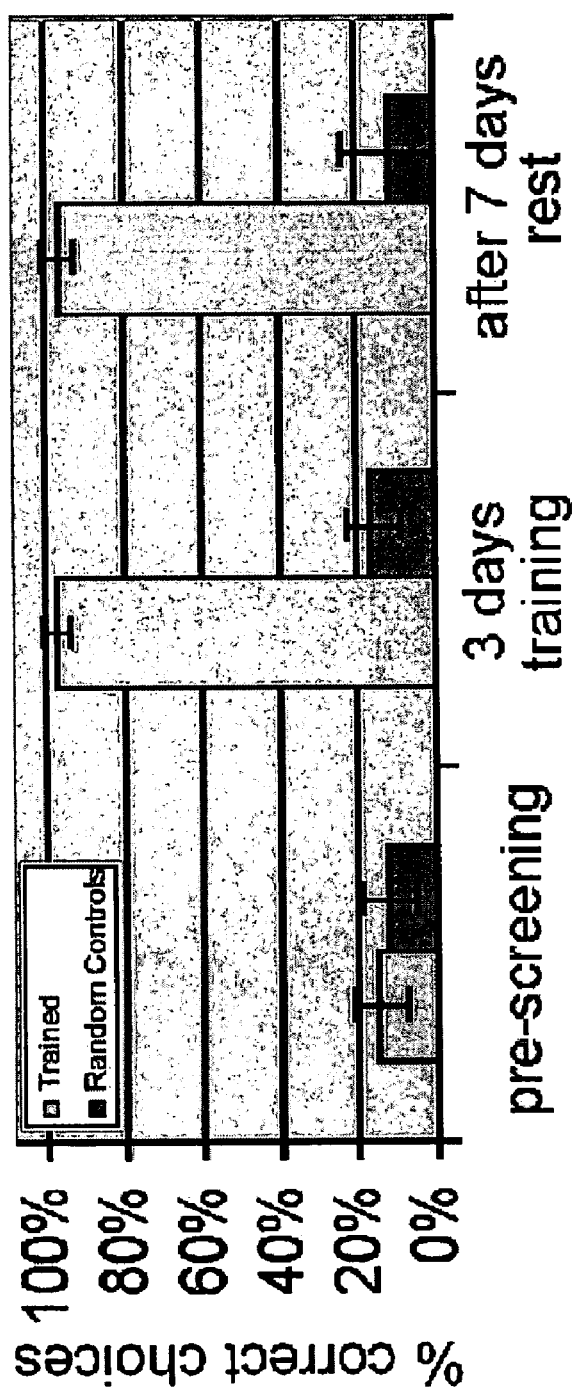
FIG. 15 summarizes experiments evaluating memory retention in planaria trained to travel into the lit regions of the reaction well.

As outlined above, these experiments demonstrate that planaria can be trained and can learn to respond in particular ways (e.g., to orient themselves in a particular direction, to travel toward light, etc). We asked how long the memory is retained by the trained worms. As summarized in FIG. 15, our experiments demonstrated that almost perfect performance was retained after a seven day rest period that followed a three day training period. In other words, the trained worms retained the learned behavior for at least seven days after the completion of the three day training period. The memory may be retained longer than seven days, but the outer limit of memory retention was not assessed. Note that the seven day period was a complete rest period, and the "proper" learned behavior was not reinforced during the rest period.

These results supported our contention that a consistent environment that automatically rewards and punishes various behavior can robustly train aquatic animals, that the animals are capable of learning using these automated training paradigms, and that trained animals can retain the learned behaviors following a period of rest during which the behaviors are not reinforced. In these experiments, the learned behavior was retained for at least seven days. In the case of experiments using planaria, memory retention of seven days is sufficient for conducting further study on, for example, regeneration.

Example 8

The Effects of Exogenous Agents

Figure 16:
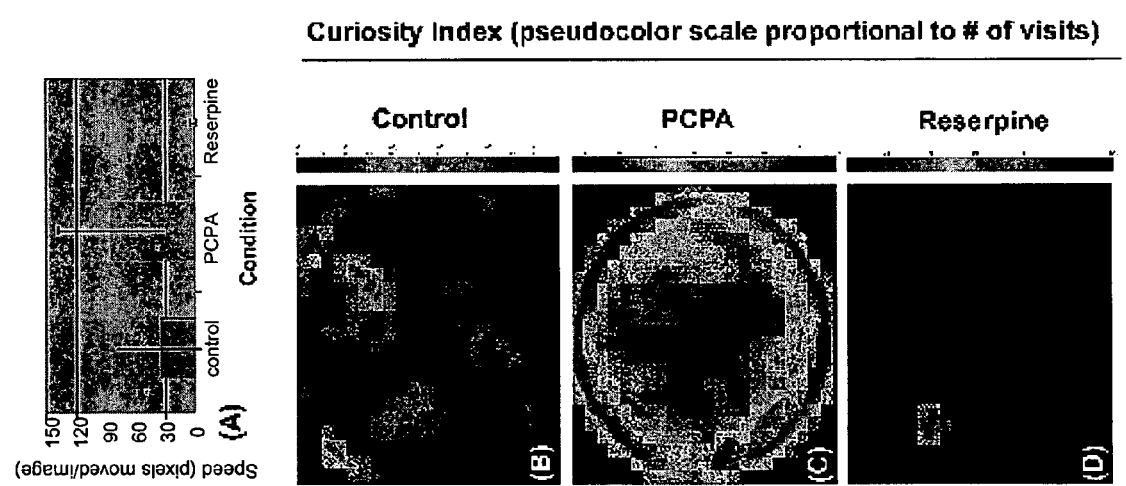
FIG. 16A summarizes the effects of various drug treatments (agents) on average speed of planaria movement.
FIGS. 16B-16D provide sample occupancy plots for single worms cultured under the indicated conditions.

We demonstrated that the automated devices and systems described above and depicted in FIGS. 3 and 10 can be used for drug (agent) screening assays and studies. FIG. 16 summarizes results depicting the effects of two agents on planaria behavior. Specifically, we assessed the effects of two psychiatric drugs that modulate serotonergic signaling, p-chlorophenylalanine (PCPA) and reserpine, on worm mobility.

Briefly, planaria were cultured in the presence of control carrier (water+DMSO), 625 micrograms/mL of PCPA, or 21 micrograms/mL of reserpine. After 24 hours of drug treatment, worm movement was observed for three hours. The speed, position, and distance traveled of individual worms were monitored following drug treatment and compared to controls. Treatment with either PCPA or reserpine had a statistically significant effect on worm movement. PCPA increased planaria movement and reserpine decreased planaria movement. FIG. 16A provides a histogram showing the average speed (pixels moved/image) following culture in media alone or in media containing either PCPA or reserpine. FIGS. 16B-D depict the effects of the agents in terms of a curiosity index. These plots provide spatial data revealing how the various treatments influenced exploration throughout the reaction well. Each curiosity plot provides data for a single worm. FIG. 16B is a curiosity plot for a worm cultured in control media. FIGS. 16C and 16D are curiosity plots for worms cultured in PCPA or reserpine, respectively.

These results indicated that the apparatuses and systems of the invention can be effectively used to analyze the effects of candidate agents/drugs/compounds. Furthermore, the devices and systems can be used for drug screening. Although in this example, animal movement (either speed or curiosity) was used to evaluate the effects of the compounds on animal behavior, virtually any behavior or phenotype can be automatically monitored and used to evaluate compounds.

Example 9

The System is Amenable for Use with a Range of Test Animals

The light/dark experiments detailed above were repeated using other experimental test organisms. Specifically, these experiments were conducted using the same systems, software, and reaction wells, but using either *Xenopus laevis* or zebrafish embryos. As above, one test organism was placed in each reaction well. Half of each reaction well was lit and the other half was un-lit (dark). The test animals were monitored for 24 hours. During this time, the software recorded the movement of the animals and made movies based on the movement in each dish. Furthermore, the system recorded the position of each animal within it's well during the monitoring period.

Statistical analysis of the data indicated that the system readily monitored, recorded, and stored data relevant to the movement of the Xenopus and zebrafish embryos. These experiments indicated that the apparatuses, systems, software, and methods of the present invention can be readily adopted for use in a range of experimental organism.

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A system for conducting assays in an aquatic test animal, comprising
   (a) a reaction well capable of housing both an aquatic test animal and appropriate fluid for maintaining said aquatic test animal, and having at least one substantially transparent viewing surface;
   (b) a removable lid that reversibly covers the reaction well and includes
      (i) an electrical element for delivering an electrical current to the reaction well,
      (ii) at least one light source for providing a light stimulus to the animal in the reaction well,
      (iii) at least one light source for providing background light to the reaction well, and
      (iv) a circuit board for interconnection to (i), (ii), and (iii);
   (c) at least one camera;
   (d) an interface box for interconnection between the camera, the circuit board, and a computer; and
   (e) image analysis software for installation on a computer which can be interconnected to the interface box.

2. The system of claim 1, wherein the electrical element includes a pair of electrodes.

3. The system of claim 1, wherein the lid further includes a shield for excluding external stimuli.

4. The system of claim 1, wherein the reaction well further includes an inlet for introducing fluid into the reaction well.

5. The system of claim 1, wherein the reaction well further includes an inlet for introducing fluid into the reaction well and an outlet for removing fluid from the reaction well.

6. The system of claim 1, wherein the system includes a plurality of reaction wells.

7. The system of claim 6, wherein the plurality of reaction wells are not in fluid communication with each other.

8. The system of claim 6, wherein each reaction well is scaled to accommodate a test animal of size and shape not easily observable without the aid of magnification.

9. The system of claim 6, wherein the plurality of reaction wells are aligned in a tray containing slots sized and shaped for the reaction wells.

10. The system of claim 1, wherein said reaction well is scaled to accommodate a test animal of size and shape not easily observable without the aid of magnification.

11. The system of claim 10, wherein said reaction well has a diameter of approximately 1-10 cm.

12. The system of claim 1, wherein said reaction well has a diameter of approximately 1-10 cm.

13. A method for screening for compounds that alter learning or memory in an aquatic test animal using said system according to claim 1, comprising
    (a) culturing a test animal in a reaction well;
    (b) training said test animal to react to a stimuli;
    (c) exposing said trained animal to a compound; and
    (d) observing changes in the reaction of the trained animal to the stimuli in the presence of the compound versus absence of the compound,
wherein a compound that alters the reaction of the trained animal to the stimuli is identified as a compound that alters learning or memory, and wherein the reactions and changes in the reactions of the test animal are measured using image analysis software installed on a computer.

14. The method of claim 1, wherein the test animal is a chordate, invertebrate, hemichordate or protochordate.

15. The method of claim 1, wherein the test animal is an aquatic animal, and wherein the reaction well houses the test animal and a fluid.

16. The method of claim 15, wherein the aquatic animal is a flatworm.

17. The method of claim 15, wherein the aquatic animal is a planarian of the class Turbellaria.

18. The method of claim 1, wherein the stimuli is light and/or an electrical current.

19. The method of claim 1, comprising a high-throughput method for screening a plurality of compounds in a plurality of reaction wells.

20. The method of claim 1, wherein the reactions and changes in the reactions of the test animal are observed using a camera.

21. A method for training a test animal using a system according to claim 1, comprising the steps of:
    providing said system for conducting assays in an aquatic test animal, wherein said system includes a stimulating element, wherein said stimulating element is one or both of said electrical element or said light source for providing a light stimulus;
    acquiring an image showing the test animal at a first instance in time;
    measuring based on the image at least one characteristic feature of the test animal;
    determining a stimulus characteristic of the stimulus based at least on the image and a similar image for another instance in time; and
    controlling the stimulating element to provide a stimulus having the stimulus characteristic to the test animal.

22. A method of claim 21, further comprising the step of initializing experimental parameters.

23. A method of claim 22, wherein the experimental parameters include at least one of duration of experiment, intensity of background lighting, behaviors of the animal to be studied.

24. A method of claim 21, wherein the stimulating element includes at least one of a light source, an electrical element, an acoustic element and chemical releasing element.

25. A method of claim 21, wherein the step of acquiring an image includes capturing an electronic image using a camera.

26. A method of claim 21, wherein the characteristic feature including at least one of a centroid, a size, a shape, a position, an axis, orientation, a velocity and an acceleration of the animal.

27. A method of claim 21, wherein the stimulus characteristic includes at least one of an intensity, a frequency and a duration of the stimulus.

28. A method of claim 21, wherein the step of determining a stimulus characteristic is based at least on the geometric characteristic of the test animal.

29. A system for conducting assays in a plurality of test animals, comprising
    (a) a plurality of reaction wells, each of which is capable of housing a test animal, wherein each reaction well has at least one substantially transparent viewing surface;
    (b) a removable lid that reversibly covers the reaction well and includes
        (i) an electrical element for delivering an electrical current to the reaction well,
        (ii) at least one light source for providing a light stimulus to the animal in the reaction well,
        (iii) at least one light source for providing background light to the reaction well, and
        (iv) a circuit board for interconnection to (i), (ii), and (iii);
    (c) at least one camera;
    (d) an interface box for interconnection between the camera, the circuit board, and a computer; and
    (e) image analysis software for installation on a computer which can be interconnected to the interface box,
wherein each reaction well is scaled to accommodate a test animal of size and shape not easily observable without the aid of magnification.

30. The system of claim 29, wherein the electrical element includes a pair of electrodes.

31. The system of claim 29, wherein the lid further includes a shield for excluding external stimuli.

32. The system of claim 29, wherein the reaction well further includes an inlet for introducing fluid into the reaction well.

33. The system of claim 29, wherein the reaction well further includes an inlet for introducing fluid into the reaction well and an outlet for removing fluid from the reaction well.

34. The system of claim 29, wherein the plurality of reaction wells are aligned in a tray containing slots sized and shaped for the reaction wells.

35. The system of claim 29, wherein the plurality of reaction wells comprises individual reaction wells, the interiors of which are not interconnected.

36. The system of claim 29, wherein the plurality of reaction wells comprises 4, 6, 12, 24, 48, 64, or 96 reaction wells.

37. The system of claim 29, wherein each reaction well has a diameter of approximately 1-10 cm.

38. The system of claim 29, wherein each reaction well has a diameter of less than 6 cm.

39. The system of claim 29, wherein each reaction well is capable of housing an aquatic test animal in less than 10 ml of fluid.

* * * * *